US012655228B2

(12) United States Patent
Chini

(10) Patent No.: US 12,655,228 B2
(45) Date of Patent: Jun. 16, 2026

(54) MATERIALS AND METHODS FOR TREATING POLYCYSTIC KIDNEY DISEASE

(71) Applicant: Mayo Foundation for Medical Education and Research, Rochester, MN (US)

(72) Inventor: Eduardo N. Chini, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 1033 days.

(21) Appl. No.: 17/441,656

(22) PCT Filed: Mar. 23, 2020

(86) PCT No.: PCT/US2020/024310

§ 371 (c)(1),
(2) Date: Sep. 21, 2021

(87) PCT Pub. No.: WO2020/198166

PCT Pub. Date: Oct. 1, 2020

(65) Prior Publication Data

US 2022/0372167 A1      Nov. 24, 2022

Related U.S. Application Data

(60) Provisional application No. 62/822,602, filed on Mar. 22, 2019.

(51) Int. Cl.
| | |
|---|---|
| *C07K 16/40* | (2006.01) |
| *A61K 39/00* | (2006.01) |
| *A61P 13/12* | (2006.01) |

(52) U.S. Cl.
CPC .............. *C07K 16/40* (2013.01); *A61P 13/12* (2018.01); *A61K 2039/505* (2013.01); *C07K 2317/622* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 6,172,198 | B1 | 1/2001 | Sinosich |
| 6,500,630 | B2 | 12/2002 | Conover et al. |
| 6,699,675 | B2 | 3/2004 | Holmes et al. |
| 7,115,382 | B1 | 10/2006 | Overgaard et al. |
| 7,220,892 | B2 | 5/2007 | Conover et al. |
| 7,402,724 | B2 | 7/2008 | Conover |
| 7,563,443 | B2 | 7/2009 | Grant et al. |
| 7,723,049 | B2 | 5/2010 | Conover et al. |
| 8,323,913 | B2 | 12/2012 | Conover et al. |
| 8,653,020 | B2 | 2/2014 | Oxvig et al. |
| 8,802,619 | B2 | 8/2014 | Birnie |
| 9,983,215 | B2 | 5/2018 | Speicher et al. |
| 12,157,776 | B2 | 12/2024 | Freund et al. |
| 2005/0009136 | A1 | 1/2005 | Nixon et al. |
| 2005/0232863 | A1 | 10/2005 | Conover |
| 2010/0310646 | A1 | 12/2010 | Oxvig et al. |
| 2015/0132770 | A1 | 5/2015 | Oxvig et al. |
| 2016/0024589 | A1 | 1/2016 | Johannessen et al. |
| 2016/0175462 | A1 | 6/2016 | Zhang et al. |
| 2016/0232293 | A1 | 8/2016 | Godzik et al. |
| 2017/0315130 | A1 | 11/2017 | Grobe et al. |
| 2024/0158534 | A1 | 5/2024 | Freund et al. |

FOREIGN PATENT DOCUMENTS

| | | |
|---|---|---|
| EP | 1169058 B1 | 5/2007 |
| EP | 1350109 B1 | 5/2009 |
| WO | WO-2009092806 A2 | 7/2009 |
| WO | WO-2014180485 A2 | 11/2014 |
| WO | WO-2018098363 A2 | 5/2018 |
| WO | WO-2018/217945 A1 | 11/2018 |
| WO | WO-2019084033 A1 | 5/2019 |
| WO | WO-2021207152 A1 | 10/2021 |

OTHER PUBLICATIONS

Edwards et al., The remarkable flexibility of the human antibody repertoire; isolation of over one thousand different antibodies to a single protein, BLyS. J Mol Biol. Nov. 14, 2003;334(1): 103-18. (Year: 2003).*

Lloyd et al., Modelling the human immune response: performance of a 1011 human antibody repertoire against a broad panel of therapeutically relevant antigens. Protein Eng Des Sel. Mar. 2009;22(3):159-68. (Year: 2009).*

Goel et al., Plasticity within the antigen-combining site may manifest as molecular mimicry in the humoral immune response. J Immunol. Dec. 15, 2004; 173(12):7358-67. (Year: 2004).*

Kanyavuz et al., Breaking the law: unconventional strategies for antibody diversification. Nat Rev Immunol. Jun. 2019; 19(6):355-368. (Year: 2019).*

EP 20777391.2 Extended European Search Report dated Nov. 25, 2022.

Kalousová, M., et al., Pregnancy-associated plasma protein A: spotlight on kidney diseases, Clin Chem Lab Med, 50(7): 1183-1190 (2012).

Kamenický, P., et al., Growth hormone, insulin-like growth factor-1, and the kidney: pathophysiological and clinical implications, Endocr Rev, 35(2): 234-281 (2014).

Kashyap, S., et al., Implications of the PAPP-A-IGFBP-IGF-1 pathway in the pathogenesis and treatment of polycystic kidney disease, Cell Signal, 73: 109698 (2020).

Kashyap, S., et al., Metalloproteinase PAPP-A regulation of IGF-1 contributes to polycystic kidney disease pathogenesis, JCI Insight, 5(4): e135700 (2020).

(Continued)

*Primary Examiner* — Maher M Haddad
(74) *Attorney, Agent, or Firm* — GOODWIN PROCTER LLP

(57)      ABSTRACT

Materials and methods for treating polycystic kidney disease (e.g., autosomal dominant polycystic kidney disease (ADPKD)) are provided herein that include using one or more inhibitors of pregnancy associated plasma protein A (PAPP-A) polypeptide expression or activity.

14 Claims, 26 Drawing Sheets

Specification includes a Sequence Listing.

(56)            References Cited

OTHER PUBLICATIONS

Mader, J.R., et al., Mice Deficient in PAPP-A Show Resistance to the Development of Diabetic Nephropathy, J Endocrinol, 219(1): 51-58 (2013).

PCT/US2020/024310 International Search Report and Written Opinion mailed Jul. 30, 2020.

Mohrin, M., et al., Inhibition of longevity regulator PAPP-A modulates tissue homeostasis via restraint of mesenchymal stromal cells, Aging Cell, 20(3): e13313 (2021).

PCT/US2023/079640 International Search Report and Written Opinion mailed Apr. 22, 2024.

Ulinski, T., et al., Serum insulin-like growth factor binding protien (IGFBP)-4 and IGFBP-5 in children with chronic renal failure: relationship to growth and glomerular filtration rate, Pediatr Nephrol, 14: 589-597 (2000).

Wang, S., et al., Insulin-Like Growth Factor Binding Proteins in Kidney Disease, Front Pharmacol, 12: 807119 (2021).

* cited by examiner

A
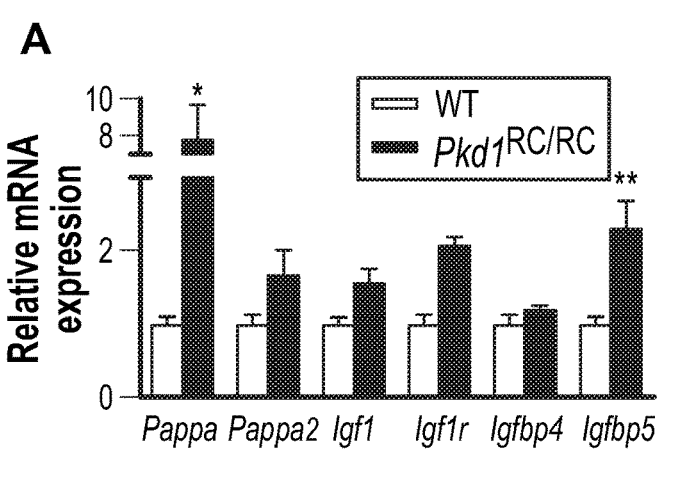
B
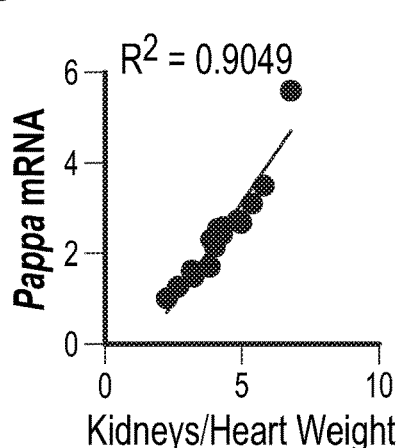
C
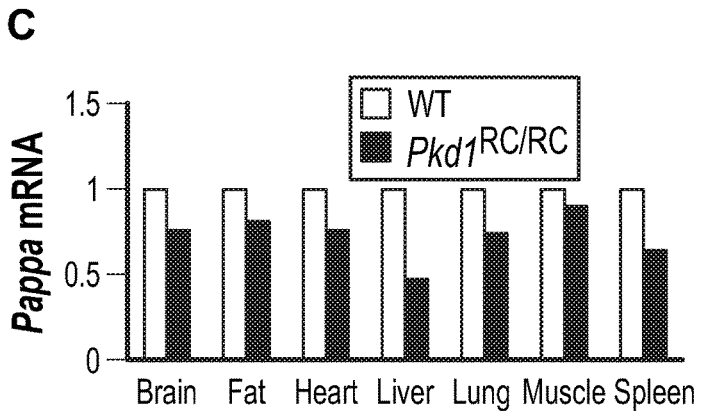
D
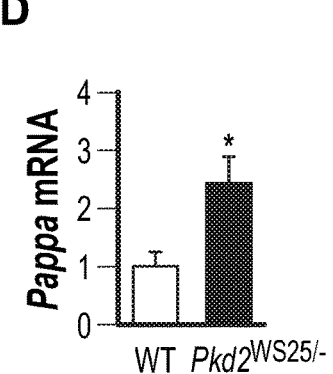
E
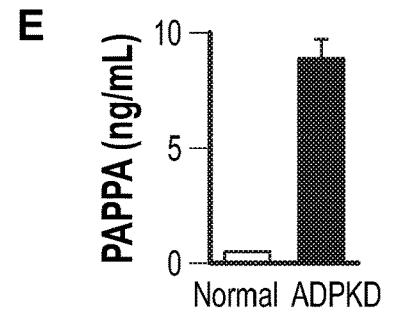
F
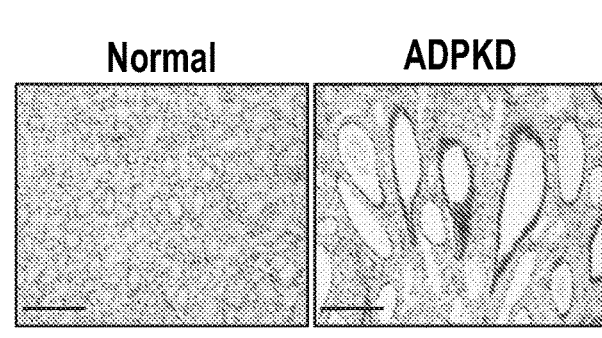
G
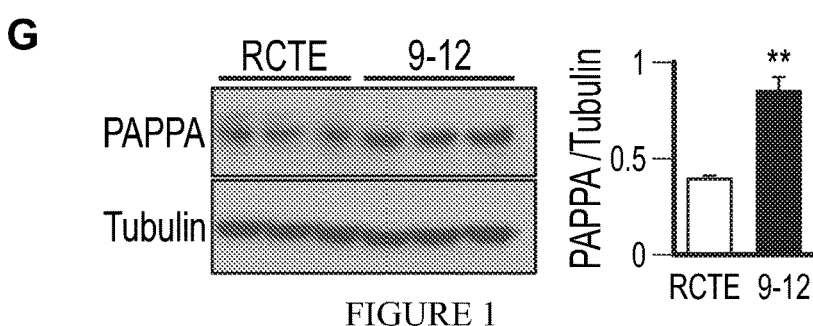
FIGURE 1

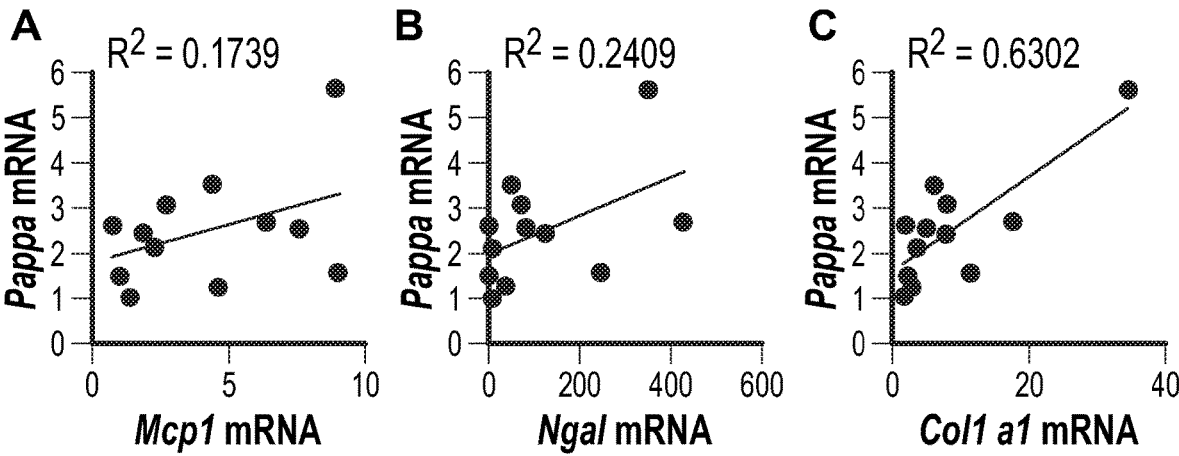
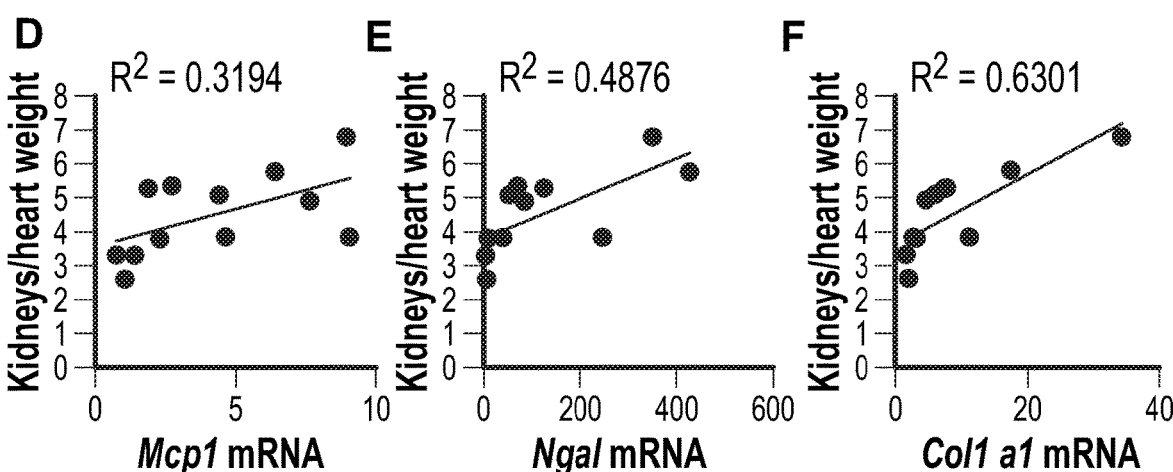
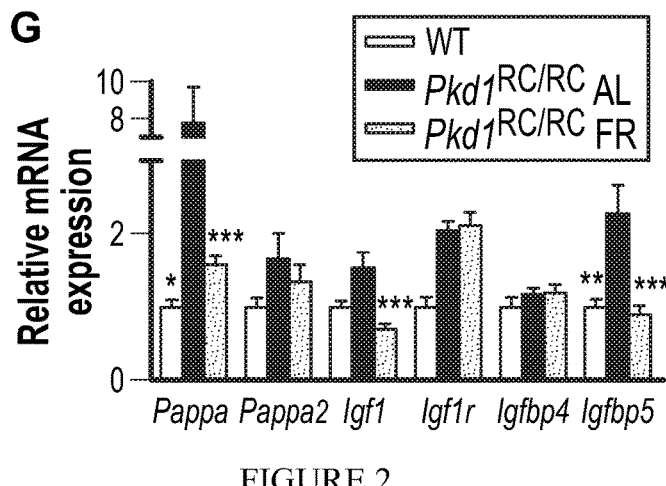
FIGURE 2

A
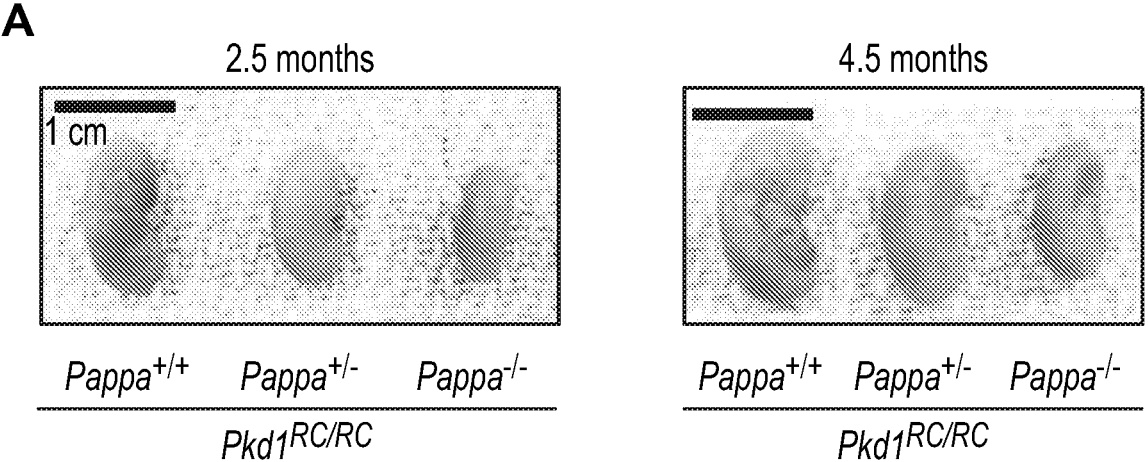
B
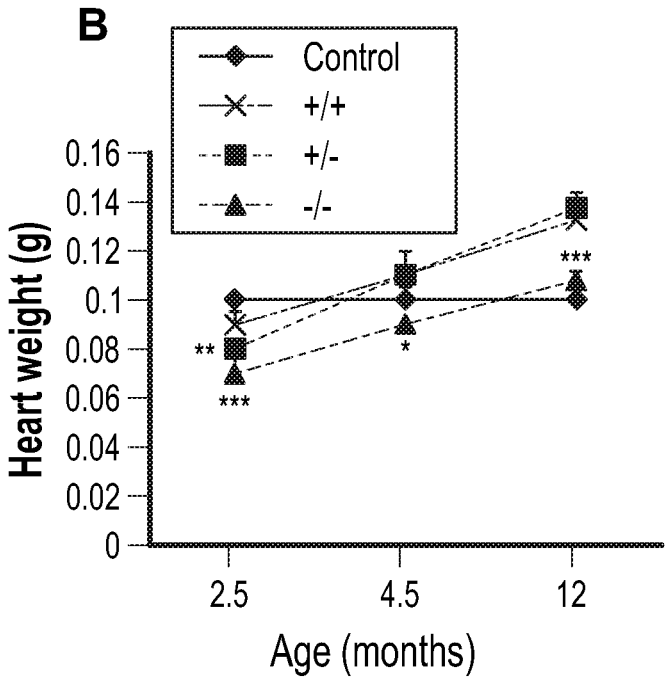
FIGURE 6

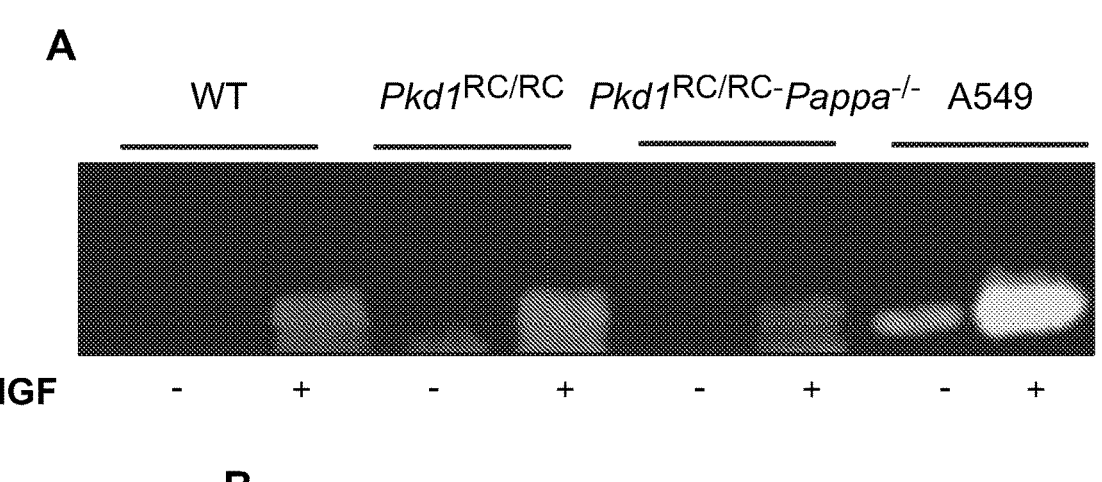
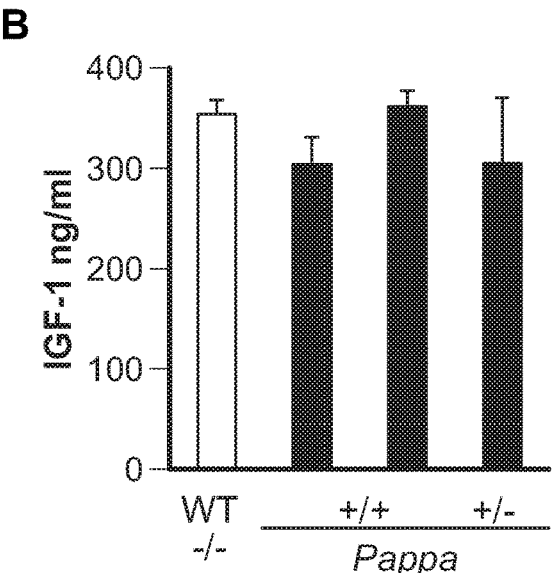
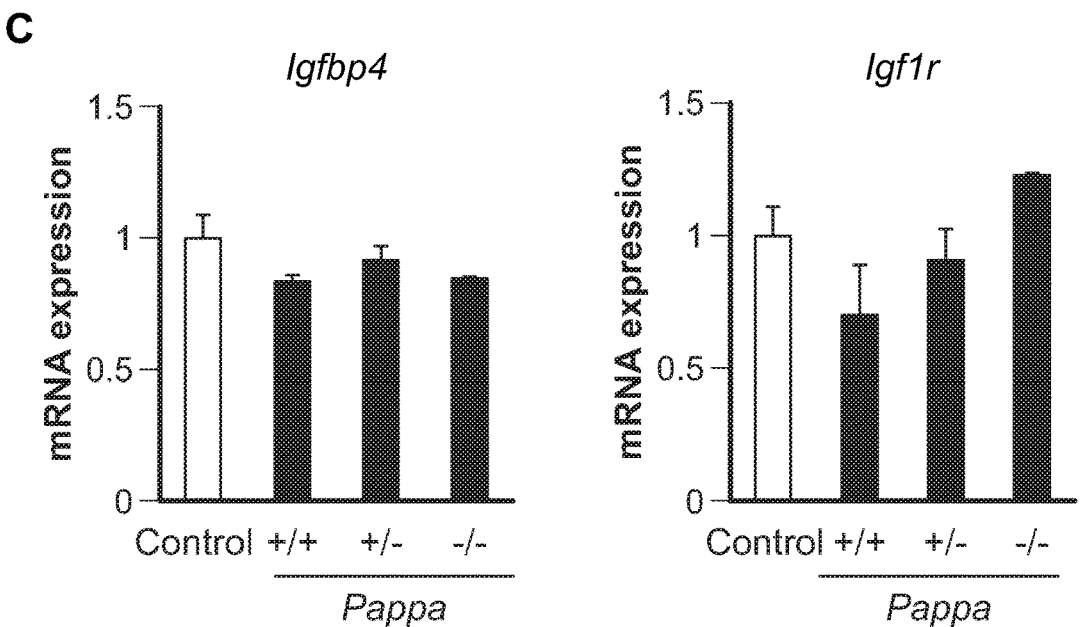
FIGURE 8

| Log-rank (Mantel-Cox) test | |
|---|---|
| Chi square | 7.806 |
| df | 1 |
| P value | 0.0052 |
| P value summary | ** |
| Are the survival curves sig different? | Yes |

EARGATEEPSPPSRALYFSGRGEQLRVLRADLELPRDAFTLQVWLRAEGGQRSPAVITG
LYDKCSYISRDRGWVVGIHTISDQDNKDPRYFFSLKTDRARQVTTINAHRSYLPGQWVY
LAATYDGQFMKLYVNGAQVATSGEQVGGIFSPLTQKCKVLMLGGSALNHNYRGYIEHF
SLWKVARTQREILSDMETHGAHTALPQLLLQENWDNVKHAWSPMKDGSSPKVEFSNA
HGFLLDTSLEPPLCGQTLCDNTEVIASYNQLSSFRQPKVVRYRVVNLYEDDHKNPTVTR
EQVDFQHHQLAEAFKQYNISWELDVLEVSNSSLRRRLILANCDISKIGDENCDPECNHTL
TGHDGGDCRHLRHPAFVKKQHNGVCDMDCNYERFNFDGGECCDPEITNVTQTCFDPDS
PHRAYLDVNELKNILKLDGSTHLNIFFAKSSEEELAGVATWPWDKEALMHLGGIVLNPS
FYGMPGHTHTMIHEIGHSLGLYHVFRGISEIQSCSDPCMETEPSFETGDLCNDTNPAPKH
KSCGDPGPGNDTCGFHSFFNTPYNNFMSYADDDCTDSFTPNQVARMHCYLDLVYQGW
QPSRKPAPVALAPQVLGHTTDSVTLEWFPPIDGHFFERELGSACHLCLEGRILVQYASNA
SSPMPCSPSGHWSPREAEGHPDVEQPCKSSVRTWSPNSAVNPHTVPPACPEPQGCYLEL
EFLYPLVPESLTIWVTFVSTDWDSSGAVNDIKLLAVSGKNISLGPQNVFCDVPLTIRLWD
VGEEVYGIQIYTLDEHLEIDAAMLTSTADTPLCLQCKPLKYKVVRDPPLQMDVASILHL
NRKFVDMDLNLGSVYQYWVITISGTEESEPSPAVTYIHGRGYCGDGIIQKDQGEQCDDM
NKINGDGCSLFCRQEVSFNCIDEPSRCYFHDGDGVCEEFEQKTSIKDCGVYTPQGFLDQ
WASNASVSHQDQQCPGWVIIGQPAASQVCRTKVIDLSEGISQHAWYPCTISYPYSQLAQ
TTFWLRAYFSQPMVAAAVIVHLVTDGTYYGDQKQETISVQLLDTKDQSHDLGLHVLSC
RNNPLIIPVVHDLSQPFYHSQAVRVSFSSPLVAISGVALRSFDNFDPVTLSSCQRGETYSP
AEQSCVHFACEK<u>TDCPELAVENASLNCSSSDRYHGAQCTVSCRTGYVLQIRRDDELIKS</u>
<u>QTGPSVTVTCTEGKWNKQVACEPVDCSIPDHHQVYAASFSCPEGTTFGSQCSFQCRHPA</u>
<u>QLKGNNSLLTCMEDGLWSFPEALCELMCLAPPPVPNADLQTARCRENKHKVGSFCKYK</u>
<u>CKPGYHVPGSSRKSKKRAFKTQCTQDGSWQEGACVPVTCDPPPPKFHGLYQCTNGFQF</u>
<u>NSECRIKCEDSDASQGLGSNVIHCRKDGTWNGSFHVCQEMQGQCSVPNELNSNLKLQC</u>
<u>PDGYAIGSECATSCLDHNSESIILPMNVTVRDIPHWLNPTRVERVVCTAGLKWYPHPALI</u>
<u>HCVKGCEPFMGDNYCDAINNRAFCNYDGGDCCTSTVKTKKVTPFPMSCDLQGDCACR</u>
<u>DPQAQEHSRKDLRGYSHG</u>

FIG. 15

Humanized mAb-PA 1/41 (humanized monoclonal Ab)

Heavy chain variable domain:

QVQLVQSGAEVKKPGASVKVSCKASGYTFTNYWLGWVRQAPGQGLEWIG**DLHPGSG
YTNYAQKLQGRVTMTTDTSTSTAYMELRSLRSDDTAVYYCVYYARNWLAY**WGQGT
LVTVSS (SEQ ID NO:8)

Framework Region 1 of heavy chain variable domain:

QVQLVQSGAEVKKPGASVKVSCKAS (SEQ ID NO:4)

CDR1 of heavy chain variable domain:

GYTFTNYWLG (SEQ ID NO:1)

Framework Region 2 of heavy chain variable domain:

WVRQAPGQGLEWIG (SEQ ID NO:5)

CDR2 of heavy chain variable domain:

DLHPGSGYTNYAQKLQG (SEQ ID NO:2)

Framework Region 3 of heavy chain variable domain:

RVTMTTDTSTSTAYMELRSLRSDDTAVYYCVYY (SEQ ID NO:6)

CDR3 of heavy chain variable domain:

ARNWLAY (SEQ ID NO:3)

Framework Region 4 of heavy chain variable domain:

WGQGTLVTVSS (SEQ ID NO:7)

FIG. 16A

Humanized mAb-PA 1/41 (humanized monoclonal Ab)

Light chain variable domain:

DIVMTQSPLSLPVTPGEPASISCRSSQSLLHSNGITYLYWYLQKPGQSPQVLIYQMSNLASGVPDRFSGSGSGTDFTLKISRVEAEDVGVYYCAQYLELPWTFGQGTKVEIKRTVA
(SEQ ID NO:16)

Framework Region 1 of light chain variable domain:

DIVMTQSPLSLPVTPGEPASISC (SEQ ID NO:12)

CDR1 of light chain variable domain:

RSSQSLLHSNGITYLY (SEQ ID NO:9)

Framework Region 2 of light chain variable domain:

WYLQKPGQSPQVLIY (SEQ ID NO:13)

CDR2 of light chain variable domain:

QMSNLAS (SEQ ID NO:10)

Framework Region 3 of light chain variable domain:

GVPDRFSGSGSGTDFTLKISRVEAEDVGVYYC (SEQ ID NO:14)

CDR3 of light chain variable domain:

AQYLELPWT (SEQ ID NO:11)

Framework Region 4 of light chain variable domain:

FGQGTKVEIKRTVA (SEQ ID NO:15)

FIG. 16B mAb-PA 1/41 (murine monoclonal Ab)

Heavy chain variable domain:

QVQLQQSGAELVRPGTSVKISCKASGYTFTNYWLGWVKQRPGHGLEWIGDLYPGSGY TNYNEKFKGKATLTADTSSSTAYMQLSSLTSEDSAVYFFVYYARNWFAYWGQGTLVT VSA (SEQ ID NO:17)

<div align="right">

FIG. 16C

</div> mAb-PA 1/41 (murine monoclonal Ab)

Light chain variable domain:

DIVMTQAAFSNPVTLGTSASISCRSSKSLLHSNGITYLYWYLQKPGQSPQVLIYQMSNL ASGVPDRFSSSGSGTDFALRISRVEAEDVGVYYCAQNLELPWTFGGGTKLEIRRADA (SEQ ID NO:18)

<div align="right">

FIG. 16D

</div>

PAC-1 scFv

Variable Heavy Region:

EVQLLESGGGLVQPGGSLRLSCAASGFTFSSYAMSWVRQAPGKGLEWVSVITDMGRT TRYADSVKGRFTISRDNSKNTLYLQMNSLRAEDTAVYYCAKGLRQFDYWGQGTLVTV SS (SEQ ID NO:19)

<div align="right">

FIG. 17A

</div>

PAC-1 scFv

Variable Light Region:

DIQMTQSPSSLSASVGDRVTITCRASQSISSYLNWYQQKPGKAPKLLIYHASQLQSGVPS RFSGSGSGTDFTLTISSLQPEDFATYYCQQYGGNPTTFGQGTKVEIKRAAA (SEQ ID NO:20)

<div align="right">

FIG. 17B

</div>

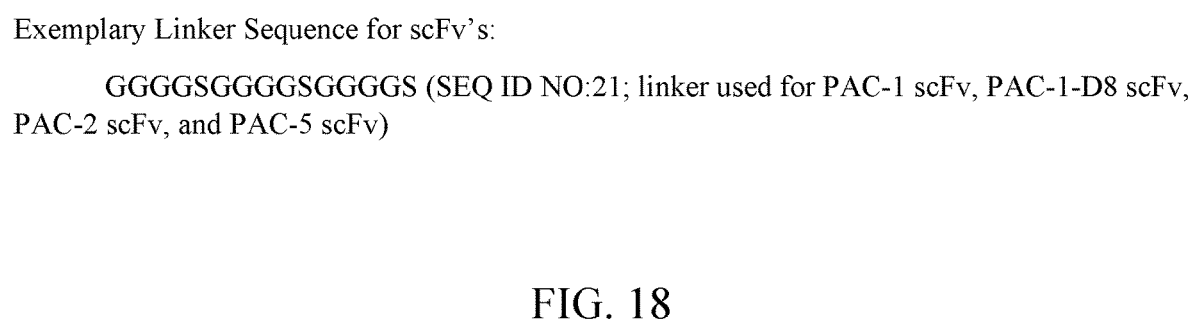

Exemplary Linker Sequence for scFv's:

GGGGSGGGGSGGGGS (SEQ ID NO:21; linker used for PAC-1 scFv, PAC-1-D8 scFv, PAC-2 scFv, and PAC-5 scFv)

FIG. 18

PAC-2 scFv

Variable Heavy Region:

EVQLLESGGGLVQPGGSLRLSCAASGFTFSSYAMSWVRQAPGKGLEWVSS
IQADGTRTGYADSVKGRFTISRDNSKNTLYLQMNSLRAEDTAVYYCAKQR
GIFDYWGQGTLVTVSS (SEQ ID NO:22)

<div align="right">

FIG. 19A

</div>

PAC-2 scFv

Variable Light Region:

TDIQMTQSPSSLSASVGDRVTITCRASQSISSYLNWYQQKPGKAPKLLIYRASGLQSGVP
SRFSGSGSG TDFTLTISSLQPEDFATYYCQQSHHYPSTFGQGTKVEIKRAAA (SEQ ID
NO:23)

<div align="right">

FIG. 19B

</div>

PAC-5 scFv

Variable Heavy Region:

EVQLLESGGGLVQPGGSLRLSCAASGFTFSSYAMSWVRQAPGKGLEWVSA
ISPAGVMTQYADSRFTISRDNSKNTLYLQMNSLRAEDTAVYYCAKQQGGF
DYWGQGTLVTVKGVSS (SEQ ID NO:24)

<div align="right">

FIG. 20A

</div>

PAC-5 scFv

Variable Light Region:

TDIQMTQSPSSLSASVGDRVTITCRASQSISSYLNWYQQKPGKAPKLLIYRASALQSGVP
SRFSGSGSG TDFTLTISSLQPEDFATYYCQQPIARPPTFGQGTKVEIKRAAA (SEQ ID
NO:25)

<div align="right">

FIG. 20B

</div>

PAC-1-D8 scFv

FIG. 21A

Variable Heavy Region:

EVQLLESGGGLVQPGGSLRLSCAASGFTFSSYAMSWVRQAPGKGLEWVSVVQGRTT
WYADSVKGRFTISRDNSKNTLYLQMNSLRAEDTAVYYCAKGLRQFDYWGQGTLVTV
SS (SEQ ID NO:26)

PAC-1-D8 scFv

FIG. 21B

Variable Light Region:

DIQMTQSPSSLSASVGDRVTITCRASQSISSYLNWYQQKPGKAPKLLIYHASQLQSGVPS
RFSGSGSGTDFTLTISSLQPEDFATYYCQQYGGNPTTFGQGTKVEIKRAAA (SEQ ID
NO:27)

C8 (murine recombinant IgG):

FIG. 21C

Variable Heavy Domain:

EVQLLESGGGLVQPGGSLRLSCAASGFTFSSYAMSWVRQAPGKGLEWVSFIHSSGQKT
LYADSVKGRFTISRDNSKNTLYLQMNSLRAEDTAVYYCAKGGHNFDYWGQGTLVTVS
S (SEQ ID NO:28)

C8 (murine recombinant IgG):

FIG. 21D

Variable Light Domain:

DIQMTQSPSSLSASVGDRVTITCRASQSISSYLNWYQQKPGKAPKLLIYAASRLQSGVPS
RFSGSGSGTDFTLTISSLQPEDFATYYCQQGTIYPPTFGQGTKVEIKRAAA (SEQ ID
NO:29)

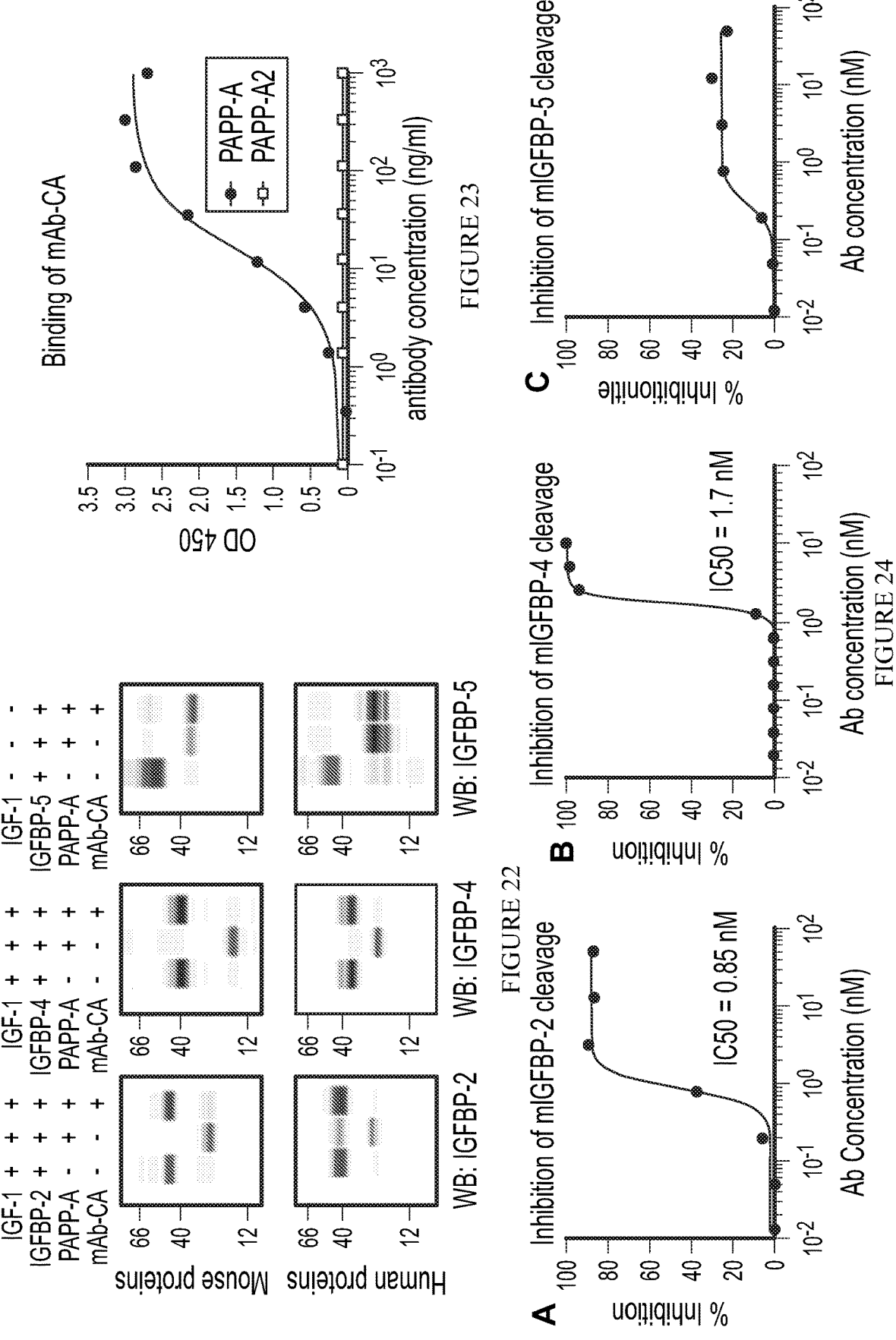

Binding affinities of additional neutralizing antibodies

| Captured Antibodies | Human PAPP-A | | | Mouse PAPP-A | | |
|---|---|---|---|---|---|---|
| | ka (1/Ms) | kd (1/s) | KD (M) | ka (1/Ms) | kd (1/s) | KD (M) |
| AC-218830 | 1.3E+05 | 2.7E-05 | 2.0E-10 | 1.4E+05 | 6.5E-05 | 4.5E-10 |
| AC-218835 | 4.8E+05 | 3.3E-04 | 6.9E-10 | 4.3E+05 | 3.3E-04 | 7.7E-10 |
| AC-218836 | 7.6E+04 | 1.2E-03 | 1.6E-08 | 7.1E+04 | 9.6E-04 | 1.4E-08 |
| AC-218842 | 7.4E+04 | 7.5E-04 | 1.0E-08 | 5.7E+04 | 5.9E-04 | 1.0E-08 |
| AC-218847 | 6.3E+04 | 5.5E-04 | 8.7E-09 | 4.5E+04 | 8.1E-05 | 1.8E-09 |

Inhibition of mouse PAPP-A cleavage of mouse IGFBP4 pAKT cellular assay

| | HillSlope | IC50 |
|---|---|---|
| AC-218830 | -1.310 | 0.3494 |
| AC-218835 | -0.6459 | 0.5241 |
| AC-218836 | -0.8554 | 2.938 |
| AC-218842 | -0.7495 | 1.777 |
| AC-218847 | -0.8133 | 1.491 |

Inhibition of human PAPP-A cleavage of human IGFBP4 Enzymatic assay

SEQUENCE LISTING

```
<160> NUMBER OF SEQ ID NOS: 32

<210> SEQ ID NO 1
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: CDR1 of heavy chain variable domain of
      humanized mAb-PA 1/41 antibody
```

```
<400> SEQUENCE: 1

Gly Tyr Thr Phe Thr Asn Tyr Trp Leu Gly
1               5                   10

<210> SEQ ID NO 2
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: CDR2 of heavy chain variable domain of
      humanized mAb-PA 1/41 antibody

<400> SEQUENCE: 2

Asp Leu His Pro Gly Ser Gly Tyr Thr Asn Tyr Ala Gln Lys Leu Gln
1               5                   10                  15

Gly

<210> SEQ ID NO 3
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: CDR3 of heavy chain variable domain of
      humanized mAb-PA 1/41 antibody

<400> SEQUENCE: 3

Ala Arg Asn Trp Leu Ala Tyr
1               5

<210> SEQ ID NO 4
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Framework Region 1 of heavy chain variable
      domain of humanized mAb-PA 1/41 antibody

<400> SEQUENCE: 4

Gln Val Gln Leu Val Gln Ser Gly Ala Glu Val Lys Lys Pro Gly Ala
1               5                   10                  15

Ser Val Lys Val Ser Cys Lys Ala Ser
            20                  25

<210> SEQ ID NO 5
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Framework Region 2 of heavy chain variable
      domain of humanized mAb-PA 1/41 antibody

<400> SEQUENCE: 5

Trp Val Arg Gln Ala Pro Gly Gln Gly Leu Glu Trp Ile Gly
1               5                   10
```

-continued

```
<210> SEQ ID NO 6
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Framework Region 3 of heavy chain variable
      domain of humanized mAb-PA 1/41 antibody

<400> SEQUENCE: 6

Arg Val Thr Met Thr Thr Asp Thr Ser Thr Ser Thr Ala Tyr Met Glu
1               5                   10                  15

Leu Arg Ser Leu Arg Ser Asp Asp Thr Ala Val Tyr Tyr Cys Val Tyr
            20                  25                  30

Tyr

<210> SEQ ID NO 7
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Framework Region 4 of heavy chain variable
      domain of humanized mAb-PA 1/41 antibody

<400> SEQUENCE: 7

Trp Gly Gln Gly Thr Leu Val Thr Val Ser Ser
1               5                   10

<210> SEQ ID NO 8
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Heavy chain variable domain of humanized mAb-PA
      1/41 antibody

<400> SEQUENCE: 8

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Leu Gly Trp Val Arg Gln Ala Pro Gly Gln Gly Leu Glu Trp Ile
        35                  40                  45

Gly Asp Leu His Pro Gly Ser Gly Tyr Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Val Tyr Tyr Ala Arg Asn Trp Leu Ala Tyr Trp Gly Gln Gly Thr Leu
            100                 105                 110

Val Thr Val Ser Ser
        115

<210> SEQ ID NO 9
```

```
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: CDR1 of light chain variable domain of
      humanized mAb-PA 1/41 antibody

<400> SEQUENCE: 9

Arg Ser Ser Gln Ser Leu Leu His Ser Asn Gly Ile Thr Tyr Leu Tyr
1               5                   10                  15

<210> SEQ ID NO 10
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: CDR2 of light chain variable domain of
      humanized mAb-PA 1/41 antibody

<400> SEQUENCE: 10

Gln Met Ser Asn Leu Ala Ser
1               5

<210> SEQ ID NO 11
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: CDR3 of light chain variable domain of
      humanized mAb-PA 1/41 antibody

<400> SEQUENCE: 11

Ala Gln Tyr Leu Glu Leu Pro Trp Thr
1               5

<210> SEQ ID NO 12
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Framework Region 1 of light chain variable
      domain of humanized mAb-PA 1/41 antibody

<400> SEQUENCE: 12

Asp Ile Val Met Thr Gln Ser Pro Leu Ser Leu Pro Val Thr Pro Gly
1               5                   10                  15

Glu Pro Ala Ser Ile Ser Cys
            20

<210> SEQ ID NO 13
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Framework Region 2 of light chain variable
``` domain of humanized mAb-PA 1/41 antibody

<400> SEQUENCE: 13

Trp Tyr Leu Gln Lys Pro Gly Gln Ser Pro Gln Val Leu Ile Tyr
1               5                   10                  15

<210> SEQ ID NO 14
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Framework Region 3 of light chain variable
      domain of humanized mAb-PA 1/41 antibody

<400> SEQUENCE: 14

Gly Val Pro Asp Arg Phe Ser Gly Ser Gly Ser Gly Thr Asp Phe Thr
1               5                   10                  15

Leu Lys Ile Ser Arg Val Glu Ala Glu Asp Val Gly Val Tyr Tyr Cys
                20                  25                  30

<210> SEQ ID NO 15
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Framework Region 4 of light chain variable
      domain of humanized mAb-PA 1/41 antibody

<400> SEQUENCE: 15

Phe Gly Gln Gly Thr Lys Val Glu Ile Lys Arg Thr Val Ala
1               5                   10

<210> SEQ ID NO 16
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Light chain variable domain of humanized mAb-PA
      1/41 antibody

<400> SEQUENCE: 16

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
                20                  25                  30

Asn Gly Ile Thr Tyr Leu Tyr Trp Tyr Leu Gln Lys Pro Gly Gln Ser
            35                  40                  45

Pro Gln Val Leu Ile Tyr Gln Met Ser Asn Leu Ala Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Tyr
                85                  90                  95

Leu Glu Leu Pro Trp Thr Phe Gly Gln Gly Thr Lys Val Glu Ile Lys
            100                 105                 110

Arg Thr Val Ala
     115

<210> SEQ ID NO 17
<211> LENGTH: 117
<212> TYPE: PRT
<213> ORGANISM: Artificial Sequence
<220> FEATURE:
<223> OTHER INFORMATION: Description of Artificial Sequence: Synthetic
    polypeptide
<220> FEATURE:
<223> OTHER INFORMATION: Heavy chain variable domain of murine mAb-PA
    1/41 antibody

<400> SEQUENCE: 17

Gln Val Gln Leu Gln Gln Ser Gly Ala Glu Leu Val Arg Pro Gly Thr
1               5                   10                  15

Ser Val Lys Ile Ser Cys Lys Ala Ser Gly Tyr Thr Phe Thr Asn Tyr
            20                  25                  30

Trp Leu Gly Trp Val Lys Gln Arg Pro Gly His Gly Leu Glu Trp Ile
        35                  40                  45

Gly Asp Leu Tyr Pro Gly Ser Gly Tyr Thr Asn Tyr Asn Glu Lys Phe
    50                  55                  60

Lys Gly Lys Ala Thr Leu Thr Ala Asp Thr Ser Ser Ser Thr Ala Tyr
65                  70                  75                  80

Met Gln Leu Ser Ser Leu Thr Ser Glu Asp Ser Ala Val Tyr Phe Phe
                85                  90                  95

Val Tyr Tyr Ala Arg Asn Trp Phe Ala Tyr Trp Gly Gln Gly Thr Leu
            100                 105                 110

Val Thr Val Ser Ala
        115

<210> SEQ ID NO 18
<211> LENGTH: 116
<212> TYPE: PRT
<213> ORGANISM: Artificial Sequence
<220> FEATURE:
<223> OTHER INFORMATION: Description of Artificial Sequence: Synthetic
    polypeptide
<220> FEATURE:
<223> OTHER INFORMATION: Light chain variable domain of murine mAb-PA
    1/41 antibody

<400> SEQUENCE: 18

Asp Ile Val Met Thr Gln Ala Ala Phe Ser Asn Pro Val Thr Leu Gly
1               5                   10                  15

Thr Ser Ala Ser Ile Ser Cys Arg Ser Ser Lys Ser Leu Leu His Ser
            20                  25                  30

Asn Gly Ile Thr Tyr Leu Tyr Trp Tyr Leu Gln Lys Pro Gly Gln Ser
        35                  40                  45

Pro Gln Val Leu Ile Tyr Gln Met Ser Asn Leu Ala Ser Gly Val Pro
    50                  55                  60

Asp Arg Phe Ser Ser Ser Gly Ser Gly Thr Asp Phe Ala Leu Arg Ile
65                  70                  75                  80

Ser Arg Val Glu Ala Glu Asp Val Gly Val Tyr Tyr Cys Ala Gln Asn
                85                  90                  95

Leu Glu Leu Pro Trp Thr Phe Gly Gly Gly Thr Lys Leu Glu Ile Arg
            100                 105                 110

Arg Ala Asp Ala
        115

-continued

```
<210> SEQ ID NO 19
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Variable heavy region of PAC-1 scFv

<400> SEQUENCE: 19

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Val Ile Thr Asp Met Gly Arg Thr Thr Arg Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Leu Arg Gln Phe Asp Tyr Trp Gly Gln Gly Thr Leu Val
            100                 105                 110

Thr Val Ser Ser
        115

<210> SEQ ID NO 20
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Variable light region of PAC-1 scFv

<400> SEQUENCE: 20

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr His Ala Ser Gln Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Gly Gly Asn Pro Thr
                85                  90                  95

Thr Phe Gly Gln Gly Thr Lys Val Glu Ile Lys Arg Ala Ala Ala
            100                 105                 110

<210> SEQ ID NO 21
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<223> OTHER INFORMATION: amino acid sequence of linker

<400> SEQUENCE: 21

Gly Gly Gly Gly Ser Gly Gly Gly Gly Ser Gly Gly Gly Gly Ser
1               5                   10                  15

<210> SEQ ID NO 22
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Variable heavy region of PAC-2 scFv

<400> SEQUENCE: 22

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Gln Ala Asp Gly Thr Arg Thr Gly Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gln Arg Gly Ile Phe Asp Tyr Trp Gly Gln Gly Thr Leu Val
            100                 105                 110

Thr Val Ser Ser
        115

<210> SEQ ID NO 23
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Variable light region of PAC-2 scFv

<400> SEQUENCE: 23

Thr Asp Ile Gln Met Thr Gln Ser Pro Ser Ser Leu Ser Ala Ser Val
1               5                   10                  15

Gly Asp Arg Val Thr Ile Thr Cys Arg Ala Ser Gln Ser Ile Ser Ser
            20                  25                  30

Tyr Leu Asn Trp Tyr Gln Gln Lys Pro Gly Lys Ala Pro Lys Leu Leu
        35                  40                  45

Ile Tyr Arg Ala Ser Gly Leu Gln Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gln Gln Ser His His Tyr Pro
                85                  90                  95

Ser Thr Phe Gly Gln Gly Thr Lys Val Glu Ile Lys Arg Ala Ala Ala
            100                 105                 110
```

-continued

<210> SEQ ID NO 24
<211> LENGTH: 116
<212> TYPE: PRT
<213> ORGANISM: Artificial Sequence
<220> FEATURE:
<223> OTHER INFORMATION: Description of Artificial Sequence: Synthetic
     polypeptide
<220> FEATURE:
<223> OTHER INFORMATION: Variable heavy region of PAC-5 scFv

<400> SEQUENCE: 24

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Pro Ala Gly Val Met Thr Gln Tyr Ala Asp Ser Arg
    50                  55                  60

Phe Thr Ile Ser Arg Asp Asn Ser Lys Asn Thr Leu Tyr Leu Gln Met
65                  70                  75                  80

Asn Ser Leu Arg Ala Glu Asp Thr Ala Val Tyr Tyr Cys Ala Lys Gln
                85                  90                  95

Gln Gly Gly Phe Asp Tyr Trp Gly Gln Gly Thr Leu Val Thr Val Lys
            100                 105                 110

Gly Val Ser Ser
        115

<210> SEQ ID NO 25
<211> LENGTH: 112
<212> TYPE: PRT
<213> ORGANISM: Artificial Sequence
<220> FEATURE:
<223> OTHER INFORMATION: Description of Artificial Sequence: Synthetic
     polypeptide
<220> FEATURE:
<223> OTHER INFORMATION: Variable light region of PAC-5 scFv

<400> SEQUENCE: 25

Thr Asp Ile Gln Met Thr Gln Ser Pro Ser Ser Leu Ser Ala Ser Val
1               5                   10                  15

Gly Asp Arg Val Thr Ile Thr Cys Arg Ala Ser Gln Ser Ile Ser Ser
            20                  25                  30

Tyr Leu Asn Trp Tyr Gln Gln Lys Pro Gly Lys Ala Pro Lys Leu Leu
        35                  40                  45

Ile Tyr Arg Ala Ser Ala Leu Gln Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gln Gln Pro Ile Ala Arg Pro
                85                  90                  95

Pro Thr Phe Gly Gln Gly Thr Lys Val Glu Ile Lys Arg Ala Ala Ala
            100                 105                 110

<210> SEQ ID NO 26
<211> LENGTH: 114
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 26

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Val Val Gln Gly Arg Thr Thr Trp Tyr Ala Asp Ser Val Lys Gly
    50                  55                  60

Arg Phe Thr Ile Ser Arg Asp Asn Ser Lys Asn Thr Leu Tyr Leu Gln
65                  70                  75                  80

Met Asn Ser Leu Arg Ala Glu Asp Thr Ala Val Tyr Tyr Cys Ala Lys
                85                  90                  95

Gly Leu Arg Gln Phe Asp Tyr Trp Gly Gln Gly Thr Leu Val Thr Val
                100                 105                 110

Ser Ser

<210> SEQ ID NO 27
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Variable light region of PAC-1-D8 scFv

<400> SEQUENCE: 27

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr His Ala Ser Gln Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Gly Gly Asn Pro Thr
                85                  90                  95

Thr Phe Gly Gln Gly Thr Lys Val Glu Ile Lys Arg Ala Ala Ala
                100                 105                 110

<210> SEQ ID NO 28
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Variable heavy domain of C8

<400> SEQUENCE: 28

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

-continued

```
Ala Met Ser Trp Val Arg Gln Ala Pro Gly Lys Gly Leu Glu Trp Val
        35                  40                  45

Ser Phe Ile His Ser Ser Gly Gln Lys Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Gly His Asn Phe Asp Tyr Trp Gly Gln Gly Thr Leu Val
            100                 105                 110

Thr Val Ser Ser
        115

<210> SEQ ID NO 29
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Variable light domain of C8

<400> SEQUENCE: 29

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Arg Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Thr Ile Tyr Pro Pro
                85                  90                  95

Thr Phe Gly Gln Gly Thr Lys Val Glu Ile Lys Arg Ala Ala Ala
            100                 105                 110

<210> SEQ ID NO 30
<211> LENGTH: 1547
<212> TYPE: PRT
<213> ORGANISM: Homo sapiens

<400> SEQUENCE: 30

Glu Ala Arg Gly Ala Thr Glu Glu Pro Ser Pro Pro Ser Arg Ala Leu
1               5                   10                  15

Tyr Phe Ser Gly Arg Gly Glu Gln Leu Arg Val Leu Arg Ala Asp Leu
            20                  25                  30

Glu Leu Pro Arg Asp Ala Phe Thr Leu Gln Val Trp Leu Arg Ala Glu
        35                  40                  45

Gly Gly Gln Arg Ser Pro Ala Val Ile Thr Gly Leu Tyr Asp Lys Cys
    50                  55                  60

Ser Tyr Ile Ser Arg Asp Arg Gly Trp Val Val Gly Ile His Thr Ile
65                  70                  75                  80

Ser Asp Gln Asp Asn Lys Asp Pro Arg Tyr Phe Phe Ser Leu Lys Thr
                85                  90                  95

Asp Arg Ala Arg Gln Val Thr Thr Ile Asn Ala His Arg Ser Tyr Leu
```

-continued

```
                100                 105                 110

Pro Gly Gln Trp Val Tyr Leu Ala Ala Thr Tyr Asp Gly Gln Phe Met
            115                 120                 125

Lys Leu Tyr Val Asn Gly Ala Gln Val Ala Thr Ser Gly Glu Gln Val
        130                 135                 140

Gly Gly Ile Phe Ser Pro Leu Thr Gln Lys Cys Lys Val Leu Met Leu
145                 150                 155                 160

Gly Gly Ser Ala Leu Asn His Asn Tyr Arg Gly Tyr Ile Glu His Phe
                165                 170                 175

Ser Leu Trp Lys Val Ala Arg Thr Gln Arg Glu Ile Leu Ser Asp Met
            180                 185                 190

Glu Thr His Gly Ala His Thr Ala Leu Pro Gln Leu Leu Leu Gln Glu
        195                 200                 205

Asn Trp Asp Asn Val Lys His Ala Trp Ser Pro Met Lys Asp Gly Ser
        210                 215                 220

Ser Pro Lys Val Glu Phe Ser Asn Ala His Gly Phe Leu Leu Asp Thr
225                 230                 235                 240

Ser Leu Glu Pro Pro Leu Cys Gly Gln Thr Leu Cys Asp Asn Thr Glu
                245                 250                 255

Val Ile Ala Ser Tyr Asn Gln Leu Ser Ser Phe Arg Gln Pro Lys Val
            260                 265                 270

Val Arg Tyr Arg Val Val Asn Leu Tyr Glu Asp Asp His Lys Asn Pro
        275                 280                 285

Thr Val Thr Arg Glu Gln Val Asp Phe Gln His His Gln Leu Ala Glu
        290                 295                 300

Ala Phe Lys Gln Tyr Asn Ile Ser Trp Glu Leu Asp Val Leu Glu Val
305                 310                 315                 320

Ser Asn Ser Ser Leu Arg Arg Arg Leu Ile Leu Ala Asn Cys Asp Ile
                325                 330                 335

Ser Lys Ile Gly Asp Glu Asn Cys Asp Pro Glu Cys Asn His Thr Leu
            340                 345                 350

Thr Gly His Asp Gly Gly Asp Cys Arg His Leu Arg His Pro Ala Phe
            355                 360                 365

Val Lys Lys Gln His Asn Gly Val Cys Asp Met Asp Cys Asn Tyr Glu
        370                 375                 380

Arg Phe Asn Phe Asp Gly Gly Glu Cys Cys Asp Pro Glu Ile Thr Asn
385                 390                 395                 400

Val Thr Gln Thr Cys Phe Asp Pro Asp Ser Pro His Arg Ala Tyr Leu
            405                 410                 415

Asp Val Asn Glu Leu Lys Asn Ile Leu Lys Leu Asp Gly Ser Thr His
            420                 425                 430

Leu Asn Ile Phe Phe Ala Lys Ser Ser Glu Glu Glu Leu Ala Gly Val
            435                 440                 445

Ala Thr Trp Pro Trp Asp Lys Glu Ala Leu Met His Leu Gly Gly Ile
        450                 455                 460

Val Leu Asn Pro Ser Phe Tyr Gly Met Pro Gly His Thr His Thr Met
465                 470                 475                 480

Ile His Glu Ile Gly His Ser Leu Gly Leu Tyr His Val Phe Arg Gly
                485                 490                 495

Ile Ser Glu Ile Gln Ser Cys Ser Asp Pro Cys Met Glu Thr Glu Pro
            500                 505                 510

Ser Phe Glu Thr Gly Asp Leu Cys Asn Asp Thr Asn Pro Ala Pro Lys
            515                 520                 525
```

-continued

```
His Lys Ser Cys Gly Asp Pro Gly Pro Gly Asn Asp Thr Cys Gly Phe
    530                 535                 540

His Ser Phe Phe Asn Thr Pro Tyr Asn Asn Phe Met Ser Tyr Ala Asp
545                 550                 555                 560

Asp Asp Cys Thr Asp Ser Phe Thr Pro Asn Gln Val Ala Arg Met His
                565                 570                 575

Cys Tyr Leu Asp Leu Val Tyr Gln Gly Trp Gln Pro Ser Arg Lys Pro
            580                 585                 590

Ala Pro Val Ala Leu Ala Pro Gln Val Leu Gly His Thr Thr Asp Ser
            595                 600                 605

Val Thr Leu Glu Trp Phe Pro Pro Ile Asp Gly His Phe Phe Glu Arg
    610                 615                 620

Glu Leu Gly Ser Ala Cys His Leu Cys Leu Glu Gly Arg Ile Leu Val
625                 630                 635                 640

Gln Tyr Ala Ser Asn Ala Ser Ser Pro Met Pro Cys Ser Pro Ser Gly
                645                 650                 655

His Trp Ser Pro Arg Glu Ala Glu Gly His Pro Asp Val Glu Gln Pro
            660                 665                 670

Cys Lys Ser Ser Val Arg Thr Trp Ser Pro Asn Ser Ala Val Asn Pro
            675                 680                 685

His Thr Val Pro Pro Ala Cys Pro Glu Pro Gln Gly Cys Tyr Leu Glu
    690                 695                 700

Leu Glu Phe Leu Tyr Pro Leu Val Pro Glu Ser Leu Thr Ile Trp Val
705                 710                 715                 720

Thr Phe Val Ser Thr Asp Trp Asp Ser Ser Gly Ala Val Asn Asp Ile
                725                 730                 735

Lys Leu Leu Ala Val Ser Gly Lys Asn Ile Ser Leu Gly Pro Gln Asn
            740                 745                 750

Val Phe Cys Asp Val Pro Leu Thr Ile Arg Leu Trp Asp Val Gly Glu
            755                 760                 765

Glu Val Tyr Gly Ile Gln Ile Tyr Thr Leu Asp Glu His Leu Glu Ile
    770                 775                 780

Asp Ala Ala Met Leu Thr Ser Thr Ala Asp Thr Pro Leu Cys Leu Gln
785                 790                 795                 800

Cys Lys Pro Leu Lys Tyr Lys Val Val Arg Asp Pro Pro Leu Gln Met
                805                 810                 815

Asp Val Ala Ser Ile Leu His Leu Asn Arg Lys Phe Val Asp Met Asp
                820                 825                 830

Leu Asn Leu Gly Ser Val Tyr Gln Tyr Trp Val Ile Thr Ile Ser Gly
            835                 840                 845

Thr Glu Glu Ser Glu Pro Ser Pro Ala Val Thr Tyr Ile His Gly Arg
    850                 855                 860

Gly Tyr Cys Gly Asp Gly Ile Ile Gln Lys Asp Gln Gly Glu Gln Cys
865                 870                 875                 880

Asp Asp Met Asn Lys Ile Asn Gly Asp Gly Cys Ser Leu Phe Cys Arg
                885                 890                 895

Gln Glu Val Ser Phe Asn Cys Ile Asp Glu Pro Ser Arg Cys Tyr Phe
            900                 905                 910

His Asp Gly Asp Gly Val Cys Glu Glu Phe Glu Gln Lys Thr Ser Ile
    915                 920                 925

Lys Asp Cys Gly Val Tyr Thr Pro Gln Gly Phe Leu Asp Gln Trp Ala
    930                 935                 940
```

-continued

```
Ser Asn Ala Ser Val Ser His Gln Asp Gln Gln Cys Pro Gly Trp Val
945             950             955             960

Ile Ile Gly Gln Pro Ala Ala Ser Gln Val Cys Arg Thr Lys Val Ile
        965             970             975

Asp Leu Ser Glu Gly Ile Ser Gln His Ala Trp Tyr Pro Cys Thr Ile
            980             985             990

Ser Tyr Pro Tyr Ser Gln Leu Ala  Gln Thr Thr Phe Trp  Leu Arg Ala
        995             1000            1005

Tyr Phe  Ser Gln Pro Met Val  Ala Ala Ala Val Ile  Val His Leu
    1010            1015            1020

Val Thr  Asp Gly Thr Tyr Tyr  Gly Asp Gln Lys Gln  Glu Thr Ile
    1025            1030            1035

Ser Val  Gln Leu Leu Asp Thr  Lys Asp Gln Ser His  Asp Leu Gly
    1040            1045            1050

Leu His  Val Leu Ser Cys Arg  Asn Asn Pro Leu Ile  Ile Pro Val
    1055            1060            1065

Val His  Asp Leu Ser Gln Pro  Phe Tyr His Ser Gln  Ala Val Arg
    1070            1075            1080

Val Ser  Phe Ser Ser Pro Leu  Val Ala Ile Ser Gly  Val Ala Leu
    1085            1090            1095

Arg Ser  Phe Asp Asn Phe Asp  Pro Val Thr Leu Ser  Ser Cys Gln
    1100            1105            1110

Arg Gly  Glu Thr Tyr Ser Pro  Ala Glu Gln Ser Cys  Val His Phe
    1115            1120            1125

Ala Cys  Glu Lys Thr Asp Cys  Pro Glu Leu Ala Val  Glu Asn Ala
    1130            1135            1140

Ser Leu  Asn Cys Ser Ser Ser  Asp Arg Tyr His Gly  Ala Gln Cys
    1145            1150            1155

Thr Val  Ser Cys Arg Thr Gly  Tyr Val Leu Gln Ile  Arg Arg Asp
    1160            1165            1170

Asp Glu  Leu Ile Lys Ser Gln  Thr Gly Pro Ser Val  Thr Val Thr
    1175            1180            1185

Cys Thr  Glu Gly Lys Trp Asn  Lys Gln Val Ala Cys  Glu Pro Val
    1190            1195            1200

Asp Cys  Ser Ile Pro Asp His  His Gln Val Tyr Ala  Ala Ser Phe
    1205            1210            1215

Ser Cys  Pro Glu Gly Thr Thr  Phe Gly Ser Gln Cys  Ser Phe Gln
    1220            1225            1230

Cys Arg  His Pro Ala Gln Leu  Lys Gly Asn Asn Ser  Leu Leu Thr
    1235            1240            1245

Cys Met  Glu Asp Gly Leu Trp  Ser Phe Pro Glu Ala  Leu Cys Glu
    1250            1255            1260

Leu Met  Cys Leu Ala Pro Pro  Pro Val Pro Asn Ala  Asp Leu Gln
    1265            1270            1275

Thr Ala  Arg Cys Arg Glu Asn  Lys His Lys Val Gly  Ser Phe Cys
    1280            1285            1290

Lys Tyr  Lys Cys Lys Pro Gly  Tyr His Val Pro Gly  Ser Ser Arg
    1295            1300            1305

Lys Ser  Lys Lys Arg Ala Phe  Lys Thr Gln Cys Thr  Gln Asp Gly
    1310            1315            1320

Ser Trp  Gln Glu Gly Ala Cys  Val Pro Val Thr Cys  Asp Pro Pro
    1325            1330            1335

Pro Pro  Lys Phe His Gly Leu  Tyr Gln Cys Thr Asn  Gly Phe Gln
```

-continued

```
              1340                1345                1350

Phe Asn Ser Glu Cys Arg Ile  Lys Cys Glu Asp Ser  Asp Ala Ser
    1355                1360                1365

Gln Gly Leu Gly Ser Asn Val  Ile His Cys Arg Lys  Asp Gly Thr
    1370                1375                1380

Trp Asn Gly Ser Phe His Val  Cys Gln Glu Met Gln  Gly Gln Cys
    1385                1390                1395

Ser Val Pro Asn Glu Leu Asn  Ser Asn Leu Lys Leu  Gln Cys Pro
    1400                1405                1410

Asp Gly Tyr Ala Ile Gly Ser  Glu Cys Ala Thr Ser  Cys Leu Asp
    1415                1420                1425

His Asn Ser Glu Ser Ile Ile  Leu Pro Met Asn Val  Thr Val Arg
    1430                1435                1440

Asp Ile Pro His Trp Leu Asn  Pro Thr Arg Val Glu  Arg Val Val
    1445                1450                1455

Cys Thr Ala Gly Leu Lys Trp  Tyr Pro His Pro Ala  Leu Ile His
    1460                1465                1470

Cys Val Lys Gly Cys Glu Pro  Phe Met Gly Asp Asn  Tyr Cys Asp
    1475                1480                1485

Ala Ile Asn Asn Arg Ala Phe  Cys Asn Tyr Asp Gly  Gly Asp Cys
    1490                1495                1500

Cys Thr Ser Thr Val Lys Thr  Lys Lys Val Thr Pro  Phe Pro Met
    1505                1510                1515

Ser Cys Asp Leu Gln Gly Asp  Cys Ala Cys Arg Asp  Pro Gln Ala
    1520                1525                1530

Gln Glu His Ser Arg Lys Asp  Leu Arg Gly Tyr Ser  His Gly
    1535                1540                1545

<210> SEQ ID NO 31
<211> LENGTH: 415
<212> TYPE: PRT
<213> ORGANISM: Homo sapiens

<400> SEQUENCE: 31

Thr Asp Cys Pro Glu Leu Ala Val Glu Asn Ala Ser Leu Asn Cys Ser
1               5                   10                  15

Ser Ser Asp Arg Tyr His Gly Ala Gln Cys Thr Val Ser Cys Arg Thr
            20                  25                  30

Gly Tyr Val Leu Gln Ile Arg Arg Asp Asp Glu Leu Ile Lys Ser Gln
        35                  40                  45

Thr Gly Pro Ser Val Thr Val Thr Cys Thr Glu Gly Lys Trp Asn Lys
    50                  55                  60

Gln Val Ala Cys Glu Pro Val Asp Cys Ser Ile Pro Asp His His Gln
65                  70                  75                  80

Val Tyr Ala Ala Ser Phe Ser Cys Pro Glu Gly Thr Thr Phe Gly Ser
                85                  90                  95

Gln Cys Ser Phe Gln Cys Arg His Pro Ala Gln Leu Lys Gly Asn Asn
            100                 105                 110

Ser Leu Leu Thr Cys Met Glu Asp Gly Leu Trp Ser Phe Pro Glu Ala
        115                 120                 125

Leu Cys Glu Leu Met Cys Leu Ala Pro Pro Pro Val Pro Asn Ala Asp
        130                 135                 140

Leu Gln Thr Ala Arg Cys Arg Glu Asn Lys His Lys Val Gly Ser Phe
145                 150                 155                 160
```

-continued

```
Cys Lys Tyr Lys Cys Lys Pro Gly Tyr His Val Pro Gly Ser Ser Arg
            165             170             175

Lys Ser Lys Lys Arg Ala Phe Lys Thr Gln Cys Thr Gln Asp Gly Ser
            180             185             190

Trp Gln Glu Gly Ala Cys Val Pro Val Thr Cys Asp Pro Pro Pro
            195             200             205

Lys Phe His Gly Leu Tyr Gln Cys Thr Asn Gly Phe Gln Phe Asn Ser
    210             215             220

Glu Cys Arg Ile Lys Cys Glu Asp Ser Asp Ala Ser Gln Gly Leu Gly
225             230             235             240

Ser Asn Val Ile His Cys Arg Lys Asp Gly Thr Trp Asn Gly Ser Phe
            245             250             255

His Val Cys Gln Glu Met Gln Gly Gln Cys Ser Val Pro Asn Glu Leu
            260             265             270

Asn Ser Asn Leu Lys Leu Gln Cys Pro Asp Gly Tyr Ala Ile Gly Ser
            275             280             285

Glu Cys Ala Thr Ser Cys Leu Asp His Asn Ser Glu Ser Ile Ile Leu
    290             295             300

Pro Met Asn Val Thr Val Arg Asp Ile Pro His Trp Leu Asn Pro Thr
305             310             315             320

Arg Val Glu Arg Val Val Cys Thr Ala Gly Leu Lys Trp Tyr Pro His
            325             330             335

Pro Ala Leu Ile His Cys Val Lys Gly Cys Glu Pro Phe Met Gly Asp
            340             345             350

Asn Tyr Cys Asp Ala Ile Asn Asn Arg Ala Phe Cys Asn Tyr Asp Gly
            355             360             365

Gly Asp Cys Cys Thr Ser Thr Val Lys Thr Lys Lys Val Thr Pro Phe
    370             375             380

Pro Met Ser Cys Asp Leu Gln Gly Asp Cys Ala Cys Arg Asp Pro Gln
385             390             395             400

Ala Gln Glu His Ser Arg Lys Asp Leu Arg Gly Tyr Ser His Gly
            405             410             415

<210> SEQ ID NO 32
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 32

His His His His His His
1               5
```

MATERIALS AND METHODS FOR TREATING POLYCYSTIC KIDNEY DISEASE

CROSS-REFERENCE TO RELATED APPLICATIONS

This application is a U.S. National Stage patent application under 35 U.S.C. § 371 of International Application No. PCT/US2020/024310, filed Mar. 23, 2020, which claims the benefit of and priority to U.S. Provisional Application No. 62/822,602, filed Mar. 22, 2019, each of which is incorporated by reference herein in its entirety.

BACKGROUND

Sequence Listing

The instant application contains a Sequence Listing which has been submitted electronically in ASCII format and is hereby incorporated by reference in its entirety. Said ASCII copy, created May 9, 2022, is named CLS_101WOUS_SL.txt and is 39,990 bytes in size.

TECHNICAL FIELD

This document relates to materials and methods for treating polycystic kidney disease (e.g., autosomal dominant polycystic kidney disease (ADPKD)). For example, this document provides materials and methods for using inhibitors of pregnancy associated plasma protein A (PAPP-A) polypeptide expression or activity to reduce one or more symptoms of polycystic kidney disease in the mammal.

BACKGROUND INFORMATION

ADPKD is the most common genetic cause of end stage kidney disease. It is caused mainly by mutations in PKD1 or PKD2, which encode for polycystin-1 (PC-1) and polycystin-2 (PC-2), respectively. Tan, et al., *Biochimica et Biophysica Acta (BBA)—Molecular Basis of Disease* 1812, 1202-1212 (2011). ADPKD is a systemic disorder that is characterized primarily by the bilateral formation of fluid-filled renal cysts, as well as extra-renal manifestations. Torres, et al., Lancet 369, 1287-1301 (2007). Progressive enlargement of renal cysts over time leads to chronic renal injury and often renal failure. ADPKD is responsible for 4-10% of patients with ESRD. See Torres et al., 2007, supra. Unfortunately, treatment options for ADPKD are very limited. Bolignano, et al., *Cochrane Database of Systematic Reviews* (2015). A better understanding of the pathophysiology of ADPKD is necessary for the development of more effective therapies for the management of this systemic disease.

SUMMARY

This document is based, at least in part, on the discovery that levels of PAPP-A, a zinc metalloproteinase that cleaves inhibitory insulin-like growth factor (IGF) binding proteins and increases the local bioactivity of IGF-1, are high in cystic fluid and kidneys of humans with ADPKD and highly induced in the kidney of ADPKD mice. As described herein, homozygous and heterozygous deletion of the Pappa gene effectively inhibited the development of cysts in a Pkd1$^{RC/RC}$ model of ADPKD. The role of PAPP-A in cystic disease appears to be mediated by the regulation of the IGF-1 pathway and cellular proliferation in the kidney. Furthermore, as described herein, treatment with an antibody (e.g., a monoclonal antibody) that blocks the proteolytic activity of PAPP-A against IGFBP4 ameliorated ADPKD cystic disease in vivo in Pkd1$^{RC/RC}$ mice and ex vivo in embryonic kidneys. These results demonstrate that the PAPP-A/IGF-1 pathway plays a role in the growth and expansion of cysts in ADPKD. As described herein, this document provides methods and materials for treating polycystic kidney disease by reducing PAPP-A polypeptide activity or expression.

In one aspect, this document features a method of treating polycystic kidney disease (e.g., ADPKD) in a mammal. The method can include administering an inhibitor of PAPP-A polypeptide expression or activity to a mammal (e.g., a human) identified as having polycystic kidney disease, wherein a symptom of the polycystic kidney disease is reduced in the mammal. The inhibitor can be a neutralizing antibody that blocks the proteolytic activity of PAPP-A. The antibody can be a monoclonal antibody or a single-chain variable fragment. The inhibitor can be a nucleic acid construct that encodes a target product that reduces expression of PAPP-A. The target product can be a small interfering RNA targeting a nucleic acid encoding PAPP-A. The target product can be a microRNA targeting a nucleic acid encoding PAPP-A. The target product can be a Cas9 nuclease and a guide RNA targeting a nucleic acid encoding PAPP-A. The symptom of the polycystic kidney disease can be cystic burden or kidney size. In some cases, the symptom of the polycystic kidney disease can be a marker of renal inflammation, injury, or fibrosis.

In some embodiments, the inhibitor of PAPP-A polypeptide expression or activity can be an antibody or antigen binding fragment comprising (a) a heavy chain variable domain or region comprising the amino acid sequences set forth in SEQ ID NO:1, SEQ ID NO:2, and SEQ ID NO:3, and (b) a light chain variable domain or region comprising the amino acid sequences set forth in SEQ ID NO:9, SEQ ID NO:10, and SEQ ID NO:11.

In some embodiments, the inhibitor of PAPP-A polypeptide expression or activity can be an antibody or antigen binding fragment comprising the CDRs of a PAC-1 scFv, a PAC-1-D8 scFv, a PAC-2 scFv, a PAC-5 scFv, a humanized mAb-PA 1/41, or a murine mAb-PA.

Unless otherwise defined, all technical and scientific terms used herein have the same meaning as commonly understood by one of ordinary skill in the art to which this disclosure pertains. Methods and materials are described herein for use in the present disclosure; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 1. Upregulation of PAPP-A is a common feature in experimental and human ADPKD. (A) Relative mRNA expression of IGF-1 pathway components in kidneys of 7.5 month old C57BL/6J (WT) and Pkd1$^{RC/RC}$ mice. PCR data are expressed relative to Gapdh, n=4 for WT and n=8 for Pkd1$^{RC/RC}$. (B) Correlation between kidney size (total kidney weight relative to heart weight) and renal Pappa mRNA expression in Pkd1$^{RC/RC}$ mice (n=15, 3-9 months old). (C) Pappa mRNA levels in different tissues of WT and Pkd1$^{RC/RC}$ mice (n=5-6). (D) Pappa mRNA levels in Pkd2$^{WS25/-}$ mouse kidneys (n=6/group). (E) ELISA analysis of PAPP-A protein levels in human ADPKD cystic fluid (n=6) compared to normal serum reference. (F) Immunolocalization of PAPP-A in normal (left) and ADPKD (right) human kidneys. (G) Western blot analysis of PAPP-A protein levels in normal human renal cortical tubular epithelial cells (RCTE) and ADPKD cystic epithelial cells (9-12); graph shows quantification relative to tubulin. Data are expressed as mean SEM. *P<0.05, P<0.01, *P<0.001 compared to WT or normal control.

FIG. 2. Food restriction ameliorated the IGF pathway components in ADPKD. (A-F) Graphs showing correlation from Pkd1$^{RC/RC}$ mice (n=12, age=3-9 months old between renal Pappa mRNA and Mcp1 (A), Ngal (B) and Col1a1 (C) mRNA expression levels and between kidneys/heart ratios and Mcp1 (D), Ngal (E) and Col1a1 (F) mRNA expression levels. (G) Relative mRNA expression of IGF-1 pathway components in kidneys of 7.5 month old WT and Pkd1$^{RC/RC}$ mice fed a standard diet ad libitum (AL) or 40% food restriction (FR) for 6 months. PCR data are expressed relative to Gapdh, n=4 for B6 AL and n=8 for Pkd1$^{RC/RC}$ AL and FR groups, *P<0.05, P<0.01, *P<0.001 compared to Pkd1$^{RC/RC}$ AL.

FIG. 6. PAPP-A deficient mice show reduced kidney size and heart weight. (A) Representative gross kidney images from 2.5 and 4.5 month old Pkd1$^{RC}$RC mice that are Pappa$^{+/+}$, Pappa$^{+/-}$, or Pappa$^{-/-}$; (B) Heart weight of WT and Pkd1$^{RC/RC}$-Pappa mutants at different ages. Data are mean±SEM. n=4-5 for WT and 5-12 for Pkd1$^{RC/RC}$; Pappa mutants. *P<0.05, P<0.01, *P<0.001 compared to Pkd1$^{RC/RC}$-Pappa$^{+/+}$ group.

FIG. 8. IGF-1 and its components in Pkd1$^{RC/RC}$-Pappa mutant mice. (A) Proteolytic assay of PAPPA mediated IGFBP4 using kidney membrane fractions from WT, Pkd1$^{RC/RC}$ and Pkd1$^{RC/RC}$-Pappa$^{-/-}$ mice at 6 months age. Membrane fractions were incubated for 72 h at 37° C. with IGFBP-4 without (−) or with (+) pre-complexing to IGF. N-terminal cleaved band is shown strongly in Pkd1$^{RC/RC}$ compared to WT mice when IGF is preincubated but nearly absent in Pkd1$^{RC/RC}$-Pappa$^{-/-}$ mice. A549 cell line is used as positive control. (B) Plasma IGF-1 levels of WT (n=5) and Pkd1$^{RC/RC}$-Pappa mutant mice (n=4-15). (C) mRNA expression levels of Igfbp4, Igfbp5 and Igf1R in WT (n=4-5) and Pkd1$^{RC/RC}$-Pappa mutants (n=5-7/group) mice.

ERK, and pAkt/Akt in kidneys of 2.5 month old Pkd1$^{RC/RC}$; Pappa$^{+/+}$ and Pkd1$^{RC/RC}$; Pappa$^{-/-}$ mice. Graphs show quantitative analysis of bands by densitometry. (C) Photomicrographs showing that IGF-1 supports cystic growth in a metanephric model of cystogenesis. Day 13.5 embryonic kidneys were stimulated with FSK (10 μM) alone, or FSK in the presence of IGF-1 (100 ng/ml). Scale bar, 1 mm. (D) Embryonic kidneys were treated with FSK (10 μM), IGF-1 (100 ng/ml), and IGFBP4 (26 nM) in the presence or absence of mAb-PA (320 μM). IGF-1 was pre-incubated with IGFBP4 prior to treatment. Data are mean±SEM. *P<0.01, **P<0.0005.

Figure 10:
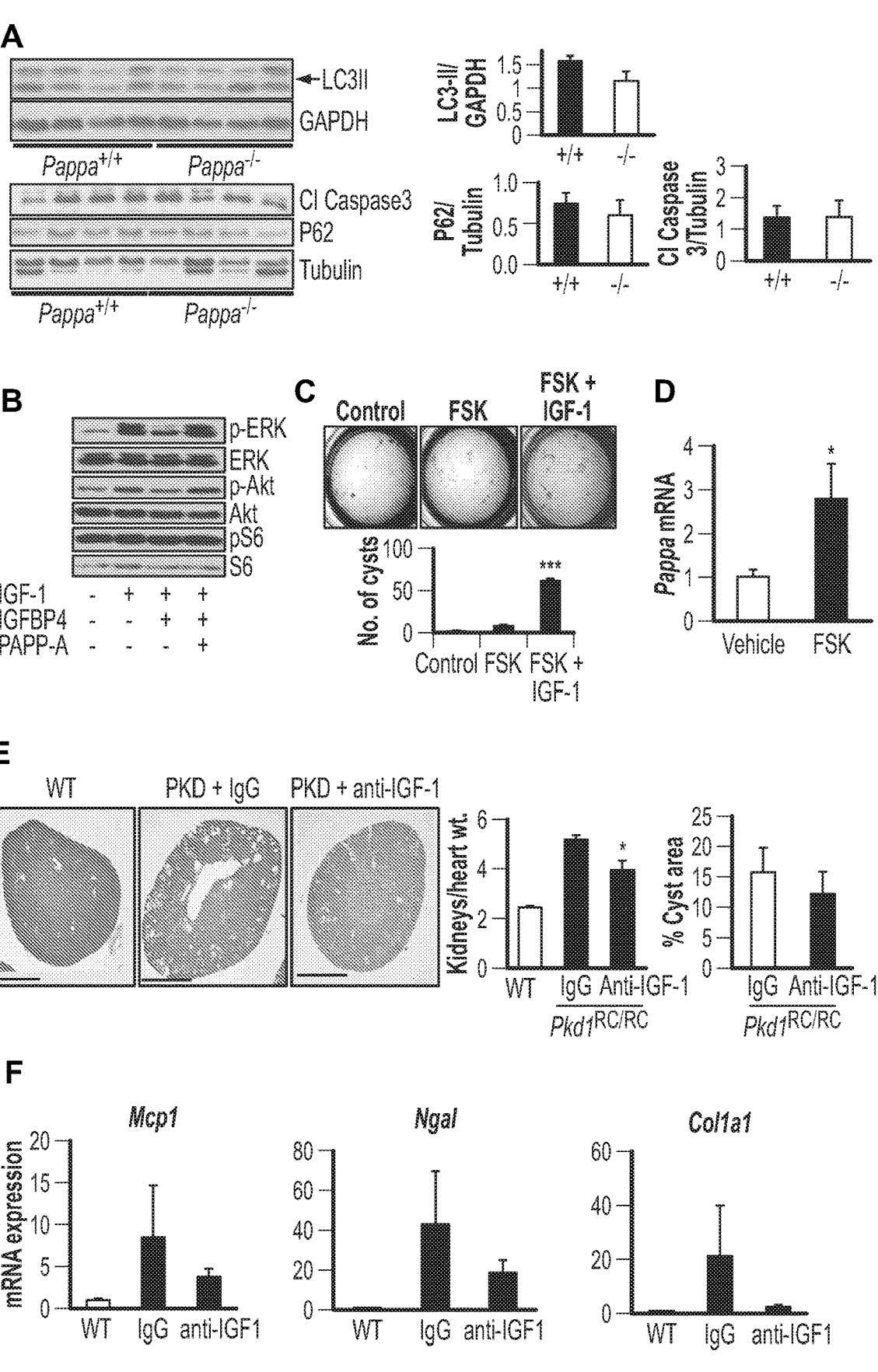

FIG. 10. Role of PAPP-A-IGF-1 pathway in pathogenesis of ADPKD in experimental models. (A) Western blot analysis of LC3, cleaved caspase 3 (Cl Caspase3) and p62 in kidneys of 2.5 month old Pkd1$^{RC/RC}$; -Pappa$^{+/+}$ and Pkd1$^{RC/RC}$-Pappa$^{-/-}$ mice. Graphs show quantitative analysis of the specific bands by densitometry. (B) Western blot analysis of IGF-1 and MAP kinase pathways in 9-12, human PKD cells in presence of IGF-1, IGFBP4 or IGFBP+PAPP-A. (C) three dimensional MDCK cystogenic assay in the presence of FSK alone or FSK+IGF1 (top) and quantification of MDCK cysts (bottom) IGF-1 (10 ng/mL). *P<0.001 compared to control. (D) Pappa mRNA expression in metanephros treated with FSK or vehicle. *P<0.05 compared to vehicle. (E) Pkd1$^{RC/RC}$ mice were treated with IGF-1 neutralizing antibody (0.2 mg/kg) or control IgG weekly by I.P. injection for 6 weeks starting at 4 months old age. Representative H&E sections of kidneys and graphs of kidneys/body weight and cystic area in IgG (n=5) and anti-IGF-1 (n=6) treated Pkd1$^{RC/RC}$ mice. (F) mRNA levels of Mcp1, Ngal and Col1a1 in IgG and anti-IGF1 (n=5 for each group) treated Pkd1$^{RC/RC}$ mice compared to WT mice (n=4).

Figure 11:
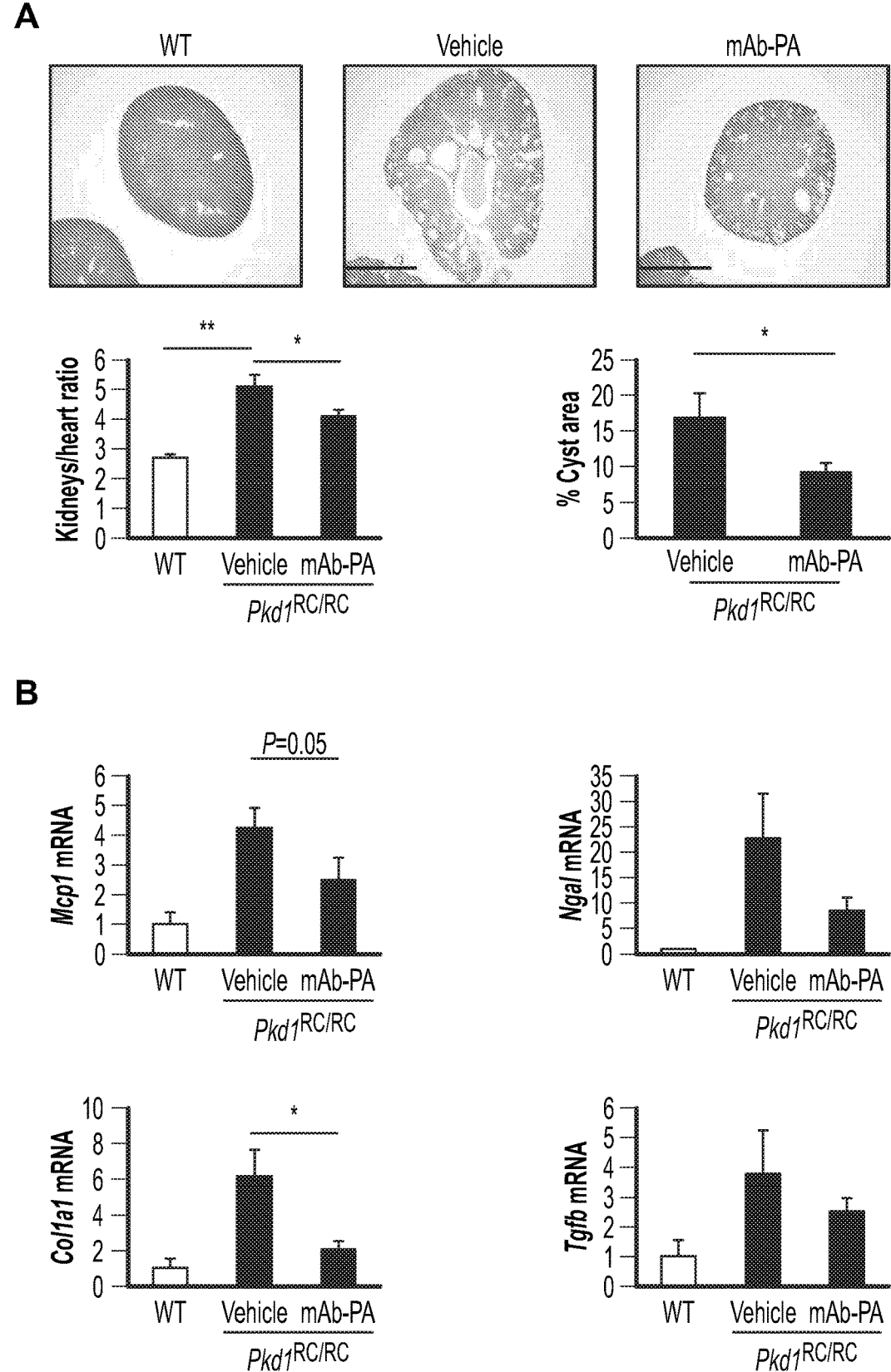

FIG. 11. Blockade of PAPP-A function with monoclonal antibody (mAb-PA) decreases cyst formation in ADPKD mice. Pkd1$^{RC/RC}$ mice were treated with mAb-PA (30 mg/kg) or vehicle once per week for 6 weeks. (A) Representative images of H&E-stained kidney sections and graphs showing kidney size and % cystic area; age=7.5 months old, n=7 for Pkd1$^{RC/RC}$ groups and n=5 for WT controls. (B) Mcp1, Ngal, Col1a1, and Tgfβ mRNA expression in mAb-PA-treated Pkd1$^{RC/RC}$ mice (n=7) and vehicle controls (n=5) at 7.5 months. Data are mean±SEM. *P<0.05, **P<0.01.

Figure 12:
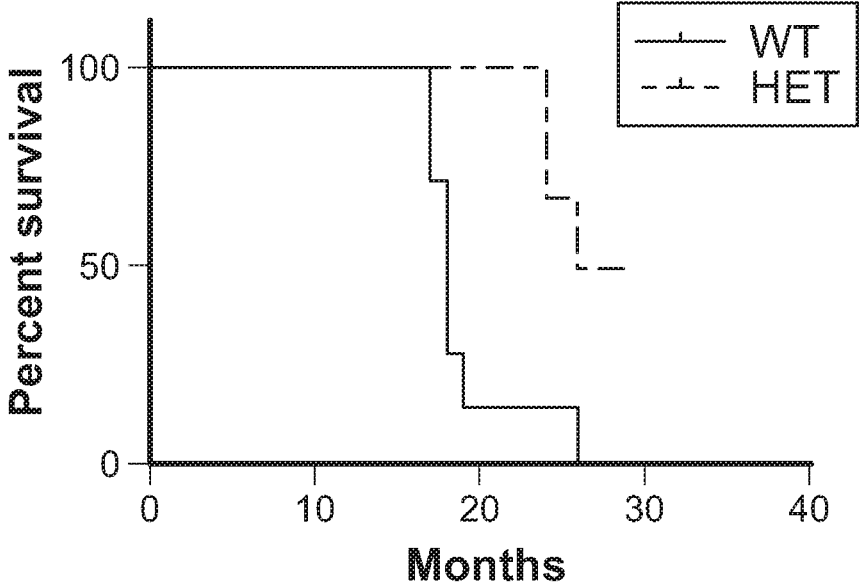

FIG. 12. Survival graph of ten Pkd1$^{RC/RC}$ wild type mice for PAPP-A (WT) and ten Pkd1$^{RC/RC}$ mice heterozygous for PAPP-A gene (HET) were followed for survival over time. The PAPP-A heterozygous mice had a significant improvement in survival over the wild type PAPP-A mice.

Figure 13:
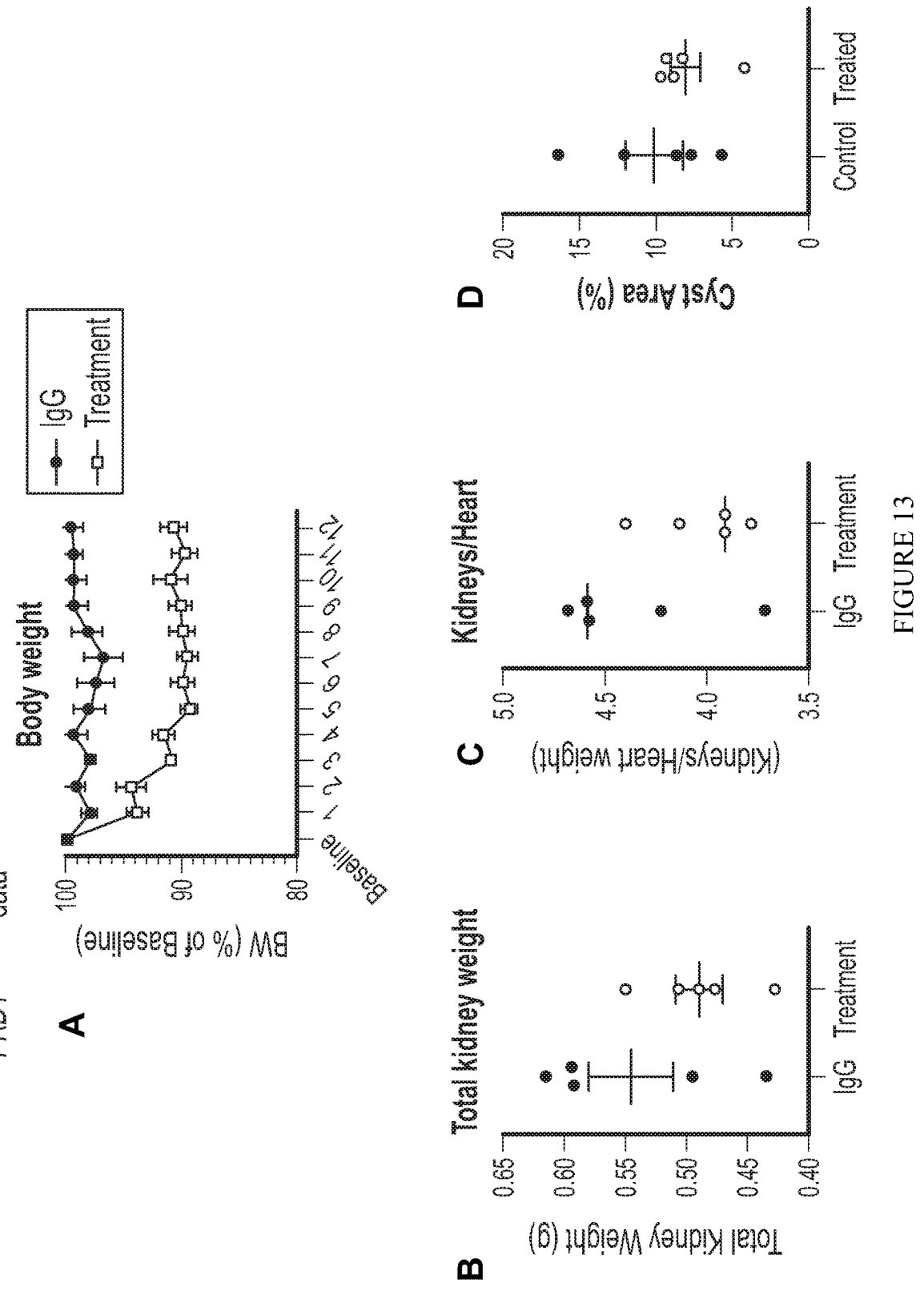

FIG. 13. PKD1$^{RC/RC}$ mice with a C57BL/6J background were treated with mAb-CA antibody (10 mg/kg) or a control (IgG) once per week for 12 weeks. (A) Body weight (% of baseline) in mAb-CA treated mice in comparison to control mice. (B) Total kidney weight (g) at harvest in mAb-CA treated mice and control mice. (C) Ratio of total kidney weight to heart weight in mAb-CA treated mice and control mice. (D) Cyst area (%) in mAb-CA treated mice and control mice.

Figure 14:
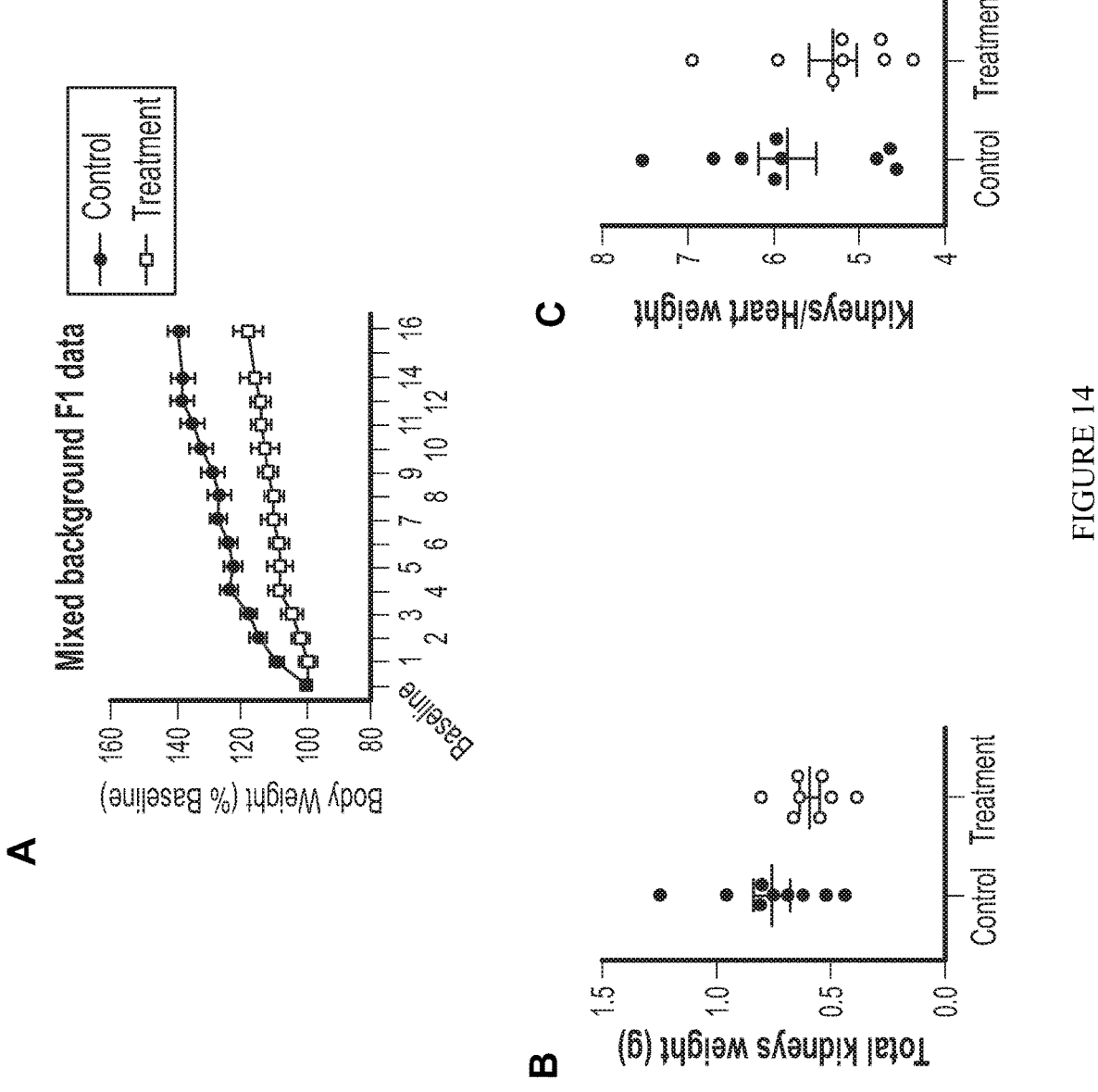

FIG. 14. PKD1$^{RC/RC}$ mice with a mixed background (C57BL6J and 129 S background) were treated with mAb-CA (10 mg/kg) or control (IgG) for 12 weeks. (A) Body weight (% of baseline) in mAb-CA treated mice in comparison to control mice. (B) Total kidney weight (g) at harvest in mAb-CA treated mice and control mice. (C) Ratio of total kidney weight to heart weight in mAb-CA treated mice and control mice.

FIG. 15 depicts the amino acid sequence of PAPP-A (SEQ ID NO:30). The substrate-binding exosite, present in the highly conserved C-terminal LNR module (LNR3) of PAPP-A, is underlined (SEQ ID NO:31).

FIGS. 16A and 16B depict the amino acid sequences of the heavy chain variable domain (FIG. 16A) and the light chain variable domain (FIG. 16B) of a monoclonal antibody designated humanized mAb-PA 1/41. The CDRs and framework sequences of each also are delineated. FIGS. 16C and 16D depict the amino acid sequences of the heavy chain variable domain (FIG. 16C) and the light chain variable domain (FIG. 16D) of a murine monoclonal antibody designated mAb-PA 1/41. The CDRs and framework sequences of each also are delineated.

FIGS. 17A and 17B depict the amino acid sequences of the heavy chain variable region (FIG. 17A) and the light chain variable region (FIG. 17B) of an scFv designated PAC-1 scFv. The CDRs and framework sequences of each also are delineated in that the CDRs are bold/underlined.

FIG. 18 depicts an exemplary linker amino acid sequence that can be used to link a heavy chain variable region and a light chain variable region together to form an scFv.

FIGS. 19A and 19B depict the amino acid sequences of the heavy chain variable region (FIG. 19A) and the light chain variable region (FIG. 19B) of an scFv designated PAC-2 scFv. The CDRs are delineated in U.S. Pat. No. 8,653,020 (see, e.g., column 33, lines 44-55).

FIGS. 20A and 20B depict the amino acid sequences of the heavy chain variable region (FIG. 20A) and the light chain variable region (FIG. 20B) of an scFv designated PAC-5 scFv. The CDRs are delineated in U.S. Pat. No. 8,653,020 (see, e.g., column 36, lines 1-11).

FIGS. 21A and 21B depict the amino acid sequences of the heavy chain variable region (FIG. 21A) and the light chain variable region (FIG. 21B) of an scFv designated PAC-1-D8 scFv. The CDRs and framework sequences of each also are delineated in that the CDRs are bold/underlined.

FIGS. 21C and 21D depict the amino acid sequences of the heavy chain variable domain (FIG. 21C) and the light chain variable domain (FIG. 21D) of a murine monoclonal IgG antibody designated C8. The CDRs and framework sequences of each also are delineated in that the CDRs are bold/underlined.

FIG. 22 shows that mAb-CA antibody blocks cleavage of human and murine IGFBP-2 and IGFBP-4, but not IGFBP-5.

FIG. 23 shows that mAb-CA antibody binds human PAPP-A, but not human PAPP-A2.

FIG. 24 shows the dose response of mAb-CA antibody inhibition of cleavage of murine (A) IGFBP-2, (B) IGFBP-4, and (C) IGFBP-5. Recombinant proteins were incubated and analyzed for IGFBP cleavage by western blot, then percent inhibition of cleavage was quantified by densitometry. IC$_{50}$s were calculated for IGFBP-2 and IGFBP-4, but did not reach 50% inhibition for IGFBP-5, and thus the IC$_{50}$ could not be determined.

Figures 25, 26, 27:
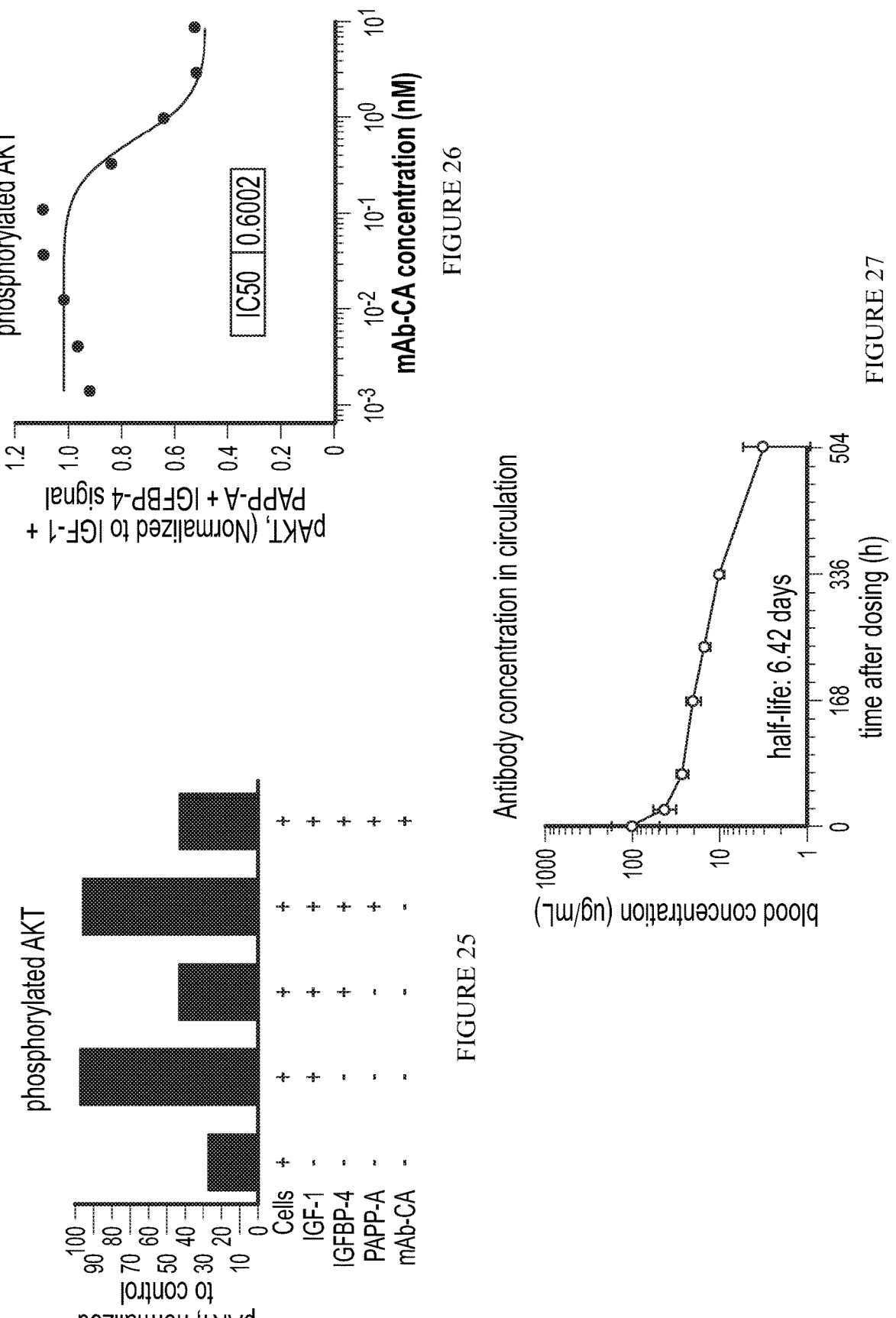

FIG. 25 shows that mAb-CA antibody suppresses IGF-1-driven AKT phosphorylation in HEK293 cells. Cells were incubated with recombinant proteins and assayed for pAKT 20 minutes later.

FIG. 26 shows a titration curve of the mAb-CA antibody suppression of IGF-1-driven AKT phosphorylation in HEK293 cells. Signal was normalized to pAKT in the presence of IGF-1, IGFBP-4, and PAPP-A.

FIG. 27 shows that the mAb-CA antibody pharmacokinetics indicate an ~6 day half-life. Antibody was IV injected into C57BL/6 mice, and blood concentration was monitored by ELISA over the course of 21 days.

Figures 28, 29, 30:
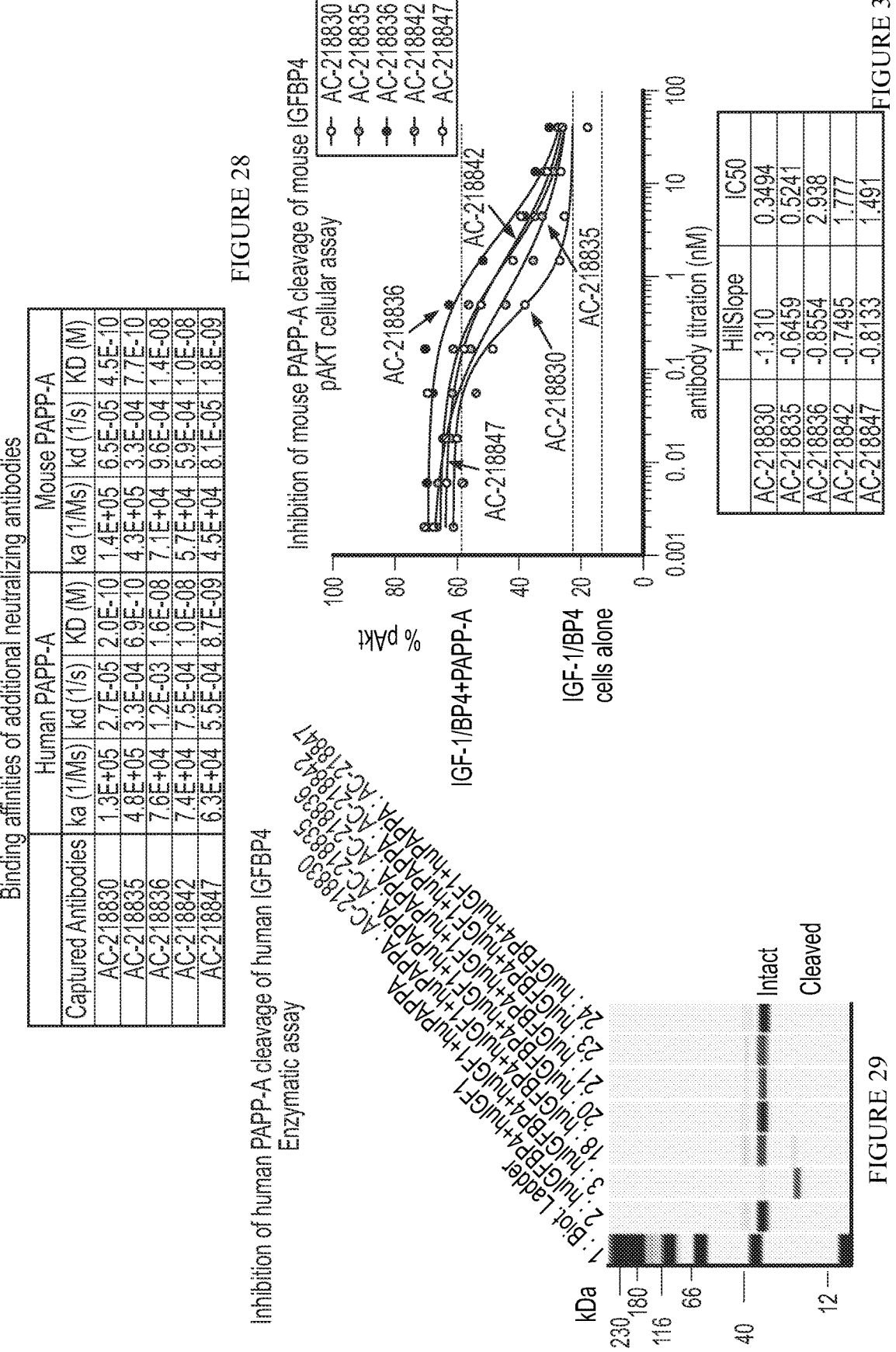

FIG. 28 shows the binding affinities of selected anti-PAPP-A antibodies generated by yeast display selection, to human and murine PAPP-A.

FIG. 29 shows that the additional anti-PAPP-A antibodies block cleavage of human IGFBP-4 at concentration 50 nM.

FIG. 30 shows a titration curve of anti-PAPP-A antibodies' suppression of IGF-1-driven AKT phosphorylation in HEK293 cells in an assay with murine IGF1, IGFBP4 and PAPP-A.

DETAILED DESCRIPTION

This document provides materials and methods for treating polycystic kidney disease in a mammal using one or more inhibitors of PAPP-A polypeptide expression or activity. PAPP-A is a secreted and cell-associated metalloproteinase that cleaves IGFBP4 in an IGF-dependent manner, freeing IGF-1 for receptor binding and activation. As such, PAPP-A is a regulator of IGF bioavailability and its physiological functions. As described herein, a direct role was identified for components of the IGF pathway including PAPP-A in the pathogenesis of ADPKD. Cystic fluid and kidneys from ADPKD patients exhibited significant increases in PAPP-A expression. Similarly, a significant increase in PAPP-A levels was observed in ADPKD cells in vitro and in murine models of ADPKD, the latter of which correlated positively with disease severity. Both genetic and pharmacological inhibition of PAPP-A conferred a remarkable protection against cystic disease. These findings demonstrate that the PAPP-A-IGF signaling pathway plays a role in ADPKD pathogenesis. As described herein, reducing PAPP-A expression or activity can be used as a therapeutic approach for treating polycystic kidney disease.

Inhibitors of PAPP-A polypeptide expression or activity can include an antibody (e.g., a neutralizing antibody that blocks the proteolytic activity of PAPP-A such as the antibodies of FIGS. 16A/16B, 16C/16D, 17A/17B, 19A/19B, 20A/20B, and 21A/21B, the mAb-CA antibody, and the antibodies of FIG. 28) or a nucleic acid construct that encodes a target product that reduces expression of PAPP-A. Any polycystic kidney disease condition can be treated as described herein, including autosomal dominant polycystic kidney disease (ADPKD) or autosomal recessive polycystic kidney disease (ARPKD). In addition, any appropriate mammal can be treated as described herein, including humans, monkeys, dogs, horses, sheep, pigs, goats, rabbits, rats or mice.

Treatments as described herein can be effective to reduce one or more symptoms of polycystic kidney disease in a mammal (e.g., a human). For example, the one or more inhibitors of PAPP-A polypeptide activity or expression can be used as described herein to reduce symptoms of polycystic kidney disease such as kidney size (e.g., reduce size of kidneys) or cystic burden (e.g., reduce size or number of cysts). Kidney size and cystic burden can be monitored using one or more imaging techniques such as ultrasound, computer-tomography (CT) scans, or magnetic resonance imaging (MRI).

In some cases, an inhibitor of PAPP-A polypeptide activity or expression for used as described herein can be a nucleic acid construct that encodes a target product that reduces expression of PAPP-A. The sequence of the nucleic acid encoding human PAPP-A is set forth in GenBank Accession No. X68280.1. Amino acid sequences of a human PAPP-A polypeptide are set forth in GenBank Accession No. CAA48341.1 and FIG. 15. The target product can be a small interfering RNA (siRNA) targeting a nucleic acid encoding PAPP-A, a short hairpin RNA (shRNA) targeting a nucleic acid encoding PAPP-A, a microRNA targeting a nucleic acid encoding PAPP-A, or the target product can include a Cas9 nuclease and a guide RNA targeting a nucleic acid encoding PAPP-A. Typically, a nucleic acid construct designed to reduce PAPP-A polypeptide activity or expression as described herein can be delivered to the mammal via a vector, such as a viral or non-viral vector. Suitable vectors include, without limitation, plasmids and viral vectors derived from, for example, bacteriophage, baculoviruses, tobacco mosaic virus, herpes viruses, cytomegalovirus, retroviruses, vaccinia viruses, adenoviruses, and adeno-associated viruses. In some cases, an expression vector such as pTAT-HA, pGEX4T2, or pSF-CMV-Neo can be used to deliver a target product described herein to a mammal to be treated. Numerous vectors and expression systems are commercially available from such corporations as Novagen (Madison, Wis.), Clonetech (Palo Alto, Calif.), Stratagene (La Jolla, Calif.), and Invitrogen/Life Technologies (Carlsbad, Calif.).

For example, a siRNA or shRNA that targets a nucleic acid encoding PAPP-A and that triggers RNA interference against PAPP-A nucleic acid expression can be used to reduce expression of PAPP-A. Software programs are available to design such siRNAs/shRNAs that can target the nucleic acid encoding human PAPP-A. See, for example, Naito et al., *Nucleic Acids Res.,* 32(Web Server issue): W124-W129 (2004)). Once designed, a particular siRNA or shRNA can be assessed in vitro or in vivo to confirm its ability to trigger RNA interference against expression of a nucleic acid encoding PAPP-A (e.g., expression of human PAPP-A). For example, a particular siRNA or shRNA can be administered to a mammal, and the level of PAPP-A polypeptide expression within the mammal (or particular tissues or cells of the mammal) can be assessed before and after administration to identify those siRNA or shRNA molecules having the ability to trigger RNA interference against expression of a nucleic acid encoding PAPP-A. In some cases, the methods and materials described elsewhere (e.g., Soulet et al., *Mol. Biol. Cell.,* 16(4):2058-2067 (2005), or Bendris et al., *Mol. Biol. Cell.,* 27(9):1409-1419 (2016)) can be used to confirm that a particular siRNA or shRNA has the ability to trigger RNA interference against expression of a PAPP-A nucleic acid.

Any appropriate method can be used to deliver one or more siRNA or shRNA molecules provided herein to cells or tissue within a mammal. See, for example, Kanasty et al., *Nature Materials,* 12(11):967-977 (2013) or Xu et al., *Asian Journal of Pharmaceutical Sciences,* 10(1):1-12 (2015)). For example, an siRNA or shRNA having the ability to trigger RNA interference against expression of a nucleic acid encoding PAPP-A can be configured into lipid nanoparticles such as those described in U.S. Patent Application Publication No. 2011/0224447 to deliver the siRNA or shRNA to cells within a mammal (e.g., a human). In some cases, one or more siRNA or shRNA molecules having the ability to trigger RNA interference against expression of PAPP-A provided herein can be delivered to kidney cells within a mammal to treat, for example, polycystic kidney disease. For example, delivery vehicles containing N-acetyl-d-galactosamine such as those described by Dhande et al., *Biomacromolecules,* 17(3):830-840 (2016)) can be used to deliver one or more siRNA or shRNA molecules having the ability to trigger RNA interference against PAPP-A expression to cells (e.g., kidney cells). In some cases, siRNA or shRNA conjugated with α-tochopherol using techniques such as those described by Murakami et al., *Scientific*

*Report,* 5:17035 (2015) can be used to deliver one or more siRNA or shRNA molecules having the ability to trigger RNA interference against PAPP-A expression to cells (e.g., kidney cells). In some cases, cyclodextrin compositions such as those described by Arima et al., *Curr. Top. Med. Chem.,* 14(4):465-77 (2014) can be used to deliver one or more siRNA or shRNA molecules having the ability to trigger RNA interference against expression of PAPP-A to cells. In some cases, a biodegradable polymeric matrix such as those described by Ramot et al., *Toxicol Pathol.,* (2016) or Golan et al., *Oncotarget,* 6(27):24560-70 (2015) can be used to deliver one or more siRNA or shRNA molecules to cells.

In some cases, clustered, regularly interspaced, short palindromic repeat (CRISPR) technology can be used to reduce expression of a nucleic acid encoding PAPP-A. A CRISPR/Cas system can include components of a prokaryotic adaptive immune system that is functionally analogous to eukaryotic RNA interference, using RNA base pairing to direct DNA or RNA cleavage. The Cas9 protein functions as an endonuclease, and CRISPR RNA (crRNA) and trans-activating RNA (tracrRNA) sequences complex with the Cas9 enzyme and direct it to a target DNA sequence (Makarova et al., *Nat Rev Microbiol* 9(6):467-477, 2011). The modification of a single targeting RNA can be sufficient to alter the nucleotide target of a Cas protein. In some cases, crRNA and tracrRNA can be engineered as a single cr/tracrRNA hybrid (also referred to as a "guide RNA" or "gRNA") to direct Cas9 cleavage activity (Jinek et al., *Science,* 337(6096):816-821, 2012). The CRISPR/Cas system can be used in a variety of prokaryotic and eukaryotic organisms (see, e.g., Jiang et al., *Nat Biotechnol,* 31(3):233-239, 2013; Dicarlo et al., *Nucleic Acids Res, doi:*10.1093/nar/gkt135, 2013; Cong et al., *Science,* 339(6121):819-823, 2013; Mali et al., *Science,* 339(6121):823-826, 2013; Cho et al., *Nat Biotechnol,* 31(3):230-232, 2013; and Hwang et al., *Nat Biotechnol,* 31(3):227-229, 2013). Each of these technologies are available commercially; see, for example, Caribou Biosciences or CRISPR Therapeutics or Editas Medicine; Cellectis Bioresearch or Life Technologies; and Sangamo BioSciences or Sigma Aldrich Chemical Co., respectively. Under the appropriate circumstances and in the presence of the proper nucleic acid-encoding polypeptides, expression of PAPP-A is reduced.

In some cases, the inhibitor of PAPP-A polypeptide expression or activity can be an antibody. This document also provides anti-PAPP-A antibody preparations, methods for making anti-PAPP-A antibody preparations, and methods for using anti-PAPP-A antibody preparations to treat polycystic kidney disease. An example of an anti-PAPP-A antibody provided herein includes, without limitation, an anti-PAPP-A antibody that targets the substrate-binding exosite, present in the highly conserved C-terminal LNR module (LNR3) of PAPP-A, referred to as mAb-PA 1/41. The mAb-PA 1/41 antibody binds PAPP-A with picomolar affinity (KD=97 μM), is specific for PAPP-A, and shows excellent inhibitory kinetics (Ki of=135 μM) towards the cleavage of IGFBP-4 for both human and murine PAPP-A. See, Mikkelsen, et al., *Oncotarget* 5, 1014-1025 (2014). In addition, monoclonal scFv antibodies such as PAC-1 (FIGS. 17A-17C), which can bind to LNR3 of PAPP-A and efficiently inhibit proteolysis of IGFBP-4, can be used as described herein. See, Mikkelsen, et al., *J. Biol. Chem.* 283, 16772-16780 (2008) and U.S. Pat. No. 8,653,020. Additional anti-PAPP-A antibodies that can be used as described herein include, without limitation, those set forth in FIGS. 16, 17, 19, and 20.

The term "antibody" as used herein includes monoclonal antibodies, polyclonal antibodies, recombinant antibodies, humanized antibodies, chimeric antibodies, multispecific antibodies (e.g., bispecific antibodies) formed from at least two antibodies, and antibody fragments. The term "antibody fragment" comprises any portion of the afore-mentioned antibodies, such as their antigen binding or variable regions. The term "epitope" refers to an antigenic determinant on an antigen to which the paratope of an antibody binds. Epitopic determinants usually consist of chemically active surface groupings of molecules (e.g., amino acid or sugar residues) and usually have specific three dimensional structural characteristics as well as specific charge characteristics.

Examples of antibody fragments include Fab fragments, Fab' fragments, $F(ab')_2$ fragments, Fv fragments, diabodies, single chain antibody molecules, and other fragments as long as they exhibit the desired capability of binding to PAPP-A. An "Fv fragment" is the minimum antibody fragment that contains a complete antigen-recognition and binding site. This region consists of a dimer of one heavy chain variable domain and one light chain variable domain in tight, non-covalent association. It is in this configuration that the three complementarity determining regions (CDRs) of each variable domain interact to define an antigen-binding site on the surface of the VH-VL dimer. Collectively, the six CDR's confer antigen-binding specificity to the antibody. However, even a single variable domain (or half of an Fv comprising only three CDR's specific for an antigen) has the ability to recognize and bind the antigen, although usually at a lower affinity than the entire binding site. The "Fab fragment" also contains the constant domain of the light chain and the first constant domain $(C_{H1})$ of the heavy chain. The "Fab fragment" differs from the "Fab' fragment" by the addition of a few residues at the carboxy terminus of the heavy chain $C_{H1}$ domain, including one or more cysteines from the antibody hinge region. The "$F(ab')_2$ fragment" originally is produced as a pair of "Fab' fragments" which have hinge cysteines between them. Methods of preparing such antibody fragments, such as papain or pepsin digestion, can be performed using any appropriate method.

In some cases, an anti-PAPP-A antibody preparation provided herein can be a preparation of whole antibodies or Fab fragments of humanized or fully-human anti-PAPP-A antibodies.

An anti-PAPP-A antibody can be of the IgA-, IgD-, IgE-, IgG- or IgM-type, including IgG- or IgM-types such as, without limitation, IgG1-, IgG2-, IgG3-, IgG4-, IgM1- and IgM2-types. For example, in some cases, the antibody is of the IgG1-, IgG2- or IgG4-type. The mAb-PA 1/41 antibody is an IgG2a antibody.

Antibodies provided herein can be prepared using any appropriate method. For example, a sample containing full-length human PAPP-A (GenBank Id. CAA48341.1) or a portion thereof (e.g., LNR3 region of PAPP-A, residues 1133-1547) can be used as an immunogen to elicit an immune response in an animal (e.g., a PAPP-A knockout mouse) such that specific antibodies are produced. The immunogen used to immunize an animal can be chemically synthesized. In some cases, the immunogen can be conjugated to a carrier polypeptide, if desired. Commonly used carriers that are chemically coupled to an immunizing polypeptide include, without limitation, keyhole limpet hemocyanin (KLH), thyroglobulin, bovine serum albumin (BSA), and tetanus toxoid.

A preparation of polyclonal antibodies can be prepared using any appropriate method. See, e.g., Green et al., Production of Polyclonal Antisera, in IMMUNOCHEMICAL PROTOCOLS (Manson, ed.), (Humana Press 1992) and Coligan et al., Production of Polyclonal Antisera in Rabbits, Rats, Mice and Hamsters, in CURRENT PROTOCOLS IN IMMUNOLOGY, section 2.4.1 (1992), or other appropriate methods for purifying and concentrating polyclonal antibodies, as well as monoclonal antibodies (Coligan et al., Unit 9, Current Protocols in Immunology, Wiley Interscience, 1994).

A preparation of monoclonal antibodies also can be prepared using any appropriate method. See, e.g., Kohler & Milstein, Nature 256:495 (1975); Coligan et al., sections 2.5.1 2.6.7; and Harlow et al., ANTIBODIES: A LABORATORY MANUAL, page 726 (Cold Spring Harbor Pub. 1988). Briefly, monoclonal antibodies can be obtained by injecting mice with a composition comprising an antigen, verifying the presence of antibody production by analyzing a serum sample, removing the spleen to obtain B lymphocytes, fusing the B lymphocytes with myeloma cells to produce hybridomas, cloning the hybridomas, selecting positive clones that produce antibodies to the antigen, and isolating the antibodies from the hybridoma cultures. Monoclonal antibodies can be isolated and purified from hybridoma cultures by a variety of well-established techniques. Such isolation techniques include affinity chromatography with Protein A Sepharose, size exclusion chromatography, and ion exchange chromatography. See, e.g., Coligan et al., sections 2.7.1 2.7.12 and sections 2.9.1 2.9.3; Barnes et al., Purification of Immunoglobulin G (IgG), in METHODS IN MOLECULAR BIOLOGY, VOL. 10, pages 79 104 (Humana Press 1992).

In addition, any methods of in vitro and in vivo multiplication of monoclonal antibodies can be used. For example, multiplication in vitro can be carried out in suitable culture media such as Dulbecco's Modified Eagle Medium or RPMI 1640 medium, optionally replenished by mammalian serum such as fetal calf serum, or trace elements and growth sustaining supplements such as normal mouse peritoneal exudate cells, spleen cells, and bone marrow macrophages. Production in vitro provides relatively pure antibody preparations and allows scale up to yield large amounts of the desired antibodies. Large scale hybridoma cultivation can be carried out by homogenous suspension culture in an airlift reactor, in a continuous stirrer reactor, or in immobilized or entrapped cell culture. Multiplication in vivo can be carried out by injecting cell clones into mammals histocompatible with the parent cells (e.g., osyngeneic mice) to cause growth of antibody producing tumors Optionally, the animals are primed with a hydrocarbon, especially oils such as pristane (tetramethylpentadecane) prior to injection. After one to three weeks, the desired monoclonal antibody is recovered from the body fluid of the animal.

In some cases, the antibodies provided herein can be made using non-human primates. General techniques for raising therapeutically useful antibodies in baboons can be found, for example, in Goldenberg et al., International Patent Publication WO 91/11465 (1991) and Losman et al., Int. J. Cancer, 46:310 (1990).

In some cases, the antibodies can be humanized monoclonal antibodies. Humanized monoclonal antibodies can be produced by transferring mouse complementarity determining regions (CDRs) from heavy and light variable chains of the mouse immunoglobulin into a human variable domain, and then substituting human residues in the framework regions of the murine counterparts. The use of antibody components derived from humanized monoclonal antibodies obviates potential problems associated with the immunogenicity of murine constant regions when treating humans. General techniques for cloning murine immunoglobulin variable domains are described, for example, by Orlandi et al., Proc. Nat'l. Acad. Sci. USA 86:3833 (1989). Techniques for producing humanized monoclonal antibodies are described, for example, by Jones et al., Nature 321:522 (1986); Riechmann et al., Nature 332:323 (1988); Verhoeyen et al., Science 239:1534 (1988); Carter et al., Proc. Nat'l. Acad. Sci. USA 89:4285 (1992); and Sandhu, Crit. Rev. Biotech. 12:437 (1992); Singer et al., J. Immunol. 150:2844 (1993). In some cases, humanization such as super humanization can be used as described by Hwang et al., Methods, 36:35-42 (2005). In some cases, SDR grafting (Kashmiri et al., Methods, 36:25-34 (2005)), human string content optimization (Lazar et al., Mol. Immunol., 44:1986-1998 (2007)), framework shuffling (Dall'Acqua et al., Methods, 36:43-60 (2005); and Damschroder et al., Mol. Immunol., 44:3049-3060 (2007)), and phage display approaches (Rosok et al., J. Biol. Chem., 271:22611-22618 (1996); Radar et al., Proc. Natl Acad. Sci. USA, 95:8910-8915 (1998); and Huse et al., Science, 246:1275-1281 (1989)) can be used to obtain anti-PAPP-A antibody preparations. In some cases, fully human antibodies can be generated from recombinant human antibody library screening techniques as described, for example, by Griffiths et al., EMBO J, 13:3245-3260 (1994); and Knappik et al., J. Mol. Biol., 296:57-86 (2000).

Antibodies provided herein can be derived from human antibody fragments isolated from a combinatorial immunoglobulin library. See, for example, Barbas et al., METHODS: A COMPANION TO METHODS IN ENZYMOLOGY, VOL. 2, page 119 (1991) and Winter et al., Ann. Rev. Immunol. 12: 433 (1994). Cloning and expression vectors that are useful for producing a human immunoglobulin phage library can be obtained, for example, from STRATAGENE Cloning Systems (La Jolla, Calif.).

In addition, antibodies provided herein can be derived from a human monoclonal antibody. Such antibodies can be obtained from transgenic mice that have been "engineered" to produce specific human antibodies in response to antigenic challenge. In this technique, elements of the human heavy and light chain loci are introduced into strains of mice derived from embryonic stem cell lines that contain targeted disruptions of the endogenous heavy and light chain loci. The transgenic mice can synthesize human antibodies specific for human antigens and can be used to produce human antibody secreting hybridomas. Methods for obtaining human antibodies from transgenic mice are described by Green et al. (Nature Genet., 7:13 (1994)), Lonberg et al. (Nature, 368:856 (1994)), and Taylor et al. (Int. Immunol., 6:579 (1994)).

Antibody fragments can be prepared by proteolytic hydrolysis of an intact antibody or by the expression of a nucleic acid encoding the fragment. Antibody fragments can be obtained by pepsin or papain digestion of intact antibodies by conventional methods. For example, Fab fragments can be produced by enzymatic cleavage of antibodies with papain. In some cases, antibody fragments can be produced by enzymatic cleavage of antibodies with pepsin to provide a 5S fragment denoted F(ab')$_2$. This fragment can be further cleaved using a thiol reducing agent, and optionally a blocking group for the sulfhydryl groups resulting from cleavage of disulfide linkages, to produce 3.5S Fab' monovalent fragments. In some cases, an enzymatic cleavage using pepsin can be used to produce two monovalent Fab' fragments and an Fc fragment directly. These methods are described, for example, by Goldenberg (U.S. Pat. Nos. 4,036,945 and 4,331,647). See also Nisonhoff et al., Arch.

*Biochem. Biophys.* 89:230 (1960); Porter, *Biochem. J.* 73:119 (1959); Edelman et al., METHODS IN ENZYMOLOGY, VOL. 1, page 422 (Academic Press 1967); and Coligan et al. at sections 2.8.1 2.8.10 and 2.10.1 2.10.4.

Other methods of cleaving antibodies, such as separation of heavy chains to form monovalent light heavy chain fragments, further cleavage of fragments, or other enzymatic, chemical, or genetic techniques may also be used provided the fragments retain some ability to bind (e.g., selectively bind) its epitope.

The antibodies provided herein can be substantially pure. The term "substantially pure" as used herein with reference to an antibody means the antibody is substantially free of other polypeptides, lipids, carbohydrates, and nucleic acid with which it is naturally associated. Thus, a substantially pure antibody is any antibody that is removed from its natural environment and is at least 60 percent pure. A substantially pure antibody can be at least about 65, 70, 75, 80, 85, 90, 95, or 99 percent pure.

In one embodiment, an anti-PAPP-A antibody (or antigen binding fragment) provided herein having the ability to bind to PAPP-A can include (i) a heavy chain variable domain having a CDR1 having the amino acid sequence set forth in SEQ ID NO:1 (or a variant of SEQ ID NO:1 with one or two amino acid modifications), a CDR2 having the amino acid sequence set forth in SEQ ID NO:2 (or a variant of SEQ ID NO:2 with one or two amino acid modifications), and a CDR3 having the amino acid sequence set forth in SEQ ID NO:3 (or a variant of SEQ ID NO:3 with one or two amino acid modifications); and/or (ii) a light chain variable domain having a CDR1 having the amino acid sequence set forth in SEQ ID NO:9 (or a variant of SEQ ID NO:9 with one or two amino acid modifications), a CDR2 having the amino acid sequence set forth in SEQ ID NO:10 (or a variant of SEQ ID NO:10 with one or two amino acid modifications), and a CDR3 having the amino acid sequence set forth SEQ ID NO:11 (or a variant of SEQ ID NO: 11 with one or two amino acid modifications). An example of such an antibody (or antigen binding fragment) having these CDRs and the ability to bind to PAPP-A includes, without limitation, the humanized monoclonal antibody set forth in FIGS. 16A and 16B.

In some cases, an anti-PAPP-A antibody (or antigen binding fragment) provided herein having the ability to bind to PAPP-A and having (a) a heavy chain variable domain having a CDR1 having the amino acid sequence set forth in SEQ ID NO:1 (or a variant of SEQ ID NO:1 with one or two amino acid modifications), a CDR2 having the amino acid sequence set forth in SEQ ID NO:2 (or a variant of SEQ ID NO:2 with one or two amino acid modifications), and a CDR3 having the amino acid sequence set forth in SEQ ID NO:3 (or a variant of SEQ ID NO:3 with one or two amino acid modifications) and/or (b) a light chain variable domain having a CDR1 having the amino acid sequence set forth in SEQ ID NO:9 (or a variant of SEQ ID NO:9 with one or two amino acid modifications), a CDR2 having the amino acid sequence set forth in SEQ ID NO:10 (or a variant of SEQ ID NO:10 with one or two amino acid modifications), and a CDR3 having the amino acid sequence set forth SEQ ID NO:11 (or a variant of SEQ ID NO: 11 with one or two amino acid modifications) can include any appropriate framework regions. For example, such an anti-PAPP-A antibody (or antigen binding fragment) can include (a) a heavy chain variable domain that includes a framework region 1 having the amino acid sequence set forth in SEQ ID NO:4 (or a variant of SEQ ID NO:4 with one, two, three, four, five, six, seven, eight, nine, ten, or more amino acid modifications), a framework region 2 having the amino acid sequence set forth in SEQ ID NO:5 (or a variant of SEQ ID NO:5 with one, two, three, four, five, six, seven, eight, nine, ten, or more amino acid modifications), a framework region 3 having the amino acid sequence set forth in SEQ ID NO:6 (or a variant of SEQ ID NO:6 with one, two, three, four, five, six, seven, eight, nine, ten, or more amino acid modifications), and a framework region 4 having the amino acid sequence set forth in SEQ ID NO:7 (or a variant of SEQ ID NO:7 with one, two, three, four, five, six, seven, eight, nine, ten, or more amino acid modifications) and/or (b) a light chain variable domain that includes a framework region 1 having the amino acid sequence set forth in SEQ ID NO:12 (or a variant of SEQ ID NO:12 with one, two, three, four, five, six, seven, eight, nine, ten, or more amino acid modifications), a framework region 2 having the amino acid sequence set forth in SEQ ID NO:13 (or a variant of SEQ ID NO:13 with one, two, three, four, five, six, seven, eight, nine, ten, or more amino acid modifications), a framework region 3 having the amino acid sequence set forth in SEQ ID NO:14 (or a variant of SEQ ID NO:14 with one, two, three, four, five, six, seven, eight, nine, ten, or more amino acid modifications), and a framework region 4 having the amino acid sequence set forth in SEQ ID NO:15 (or a variant of SEQ ID NO:15 with one, two, three, four, five, six, seven, eight, nine, ten, or more amino acid modifications).

In some cases, an anti-PAPP-A antibody (or antigen binding fragment) having any of the CDRs set forth in FIG. 16A or 16B can be designed to include framework regions as set forth in FIGS. 16A and 16B or can be designed to include one or more framework regions from another antibody or antibody fragment. For example, a monoclonal antibody can be designed to include the six CDRs set forth in FIGS. 16A and 16B and the framework regions set forth in FIGS. 16A and 16B except that framework region 1 having the amino acid set forth in SEQ ID NO:4 is replaced with a framework region 1 of another antibody. In another example, a monoclonal antibody can be designed to include the six CDRs set forth in FIGS. 16A and 16B and the framework regions set forth in FIGS. 16A and 16B except that framework region 1 having the amino acid set forth in SEQ ID NO: 12 is replaced with a framework region 1 of another antibody. In another example, a scFv can be designed to include the six CDRs set forth in FIGS. 16A and 16B and the framework regions of a scFv such as PAC1 scFv, PAC2 scFv, or PAC3 scFv.

In some cases, an anti-PAPP-A antibody (or antigen binding fragment) provided herein having the ability to bind to PAPP-A can include (a) a heavy chain variable domain that includes an amino acid sequence having at least 90 percent identity to the amino acid sequence set forth in SEQ ID NO:8 and/or (b) a light chain variable domain that includes an amino acid sequence having at least 90 percent identity to the amino acid sequence set forth in SEQ ID NO:16. For example, an anti-PAPP-A antibody (or antigen binding fragment) provided herein can include (a) a heavy chain variable domain that includes an amino acid sequence having at least 90, 91, 92, 93, 94, 95, 96, 97, 98, or 99 percent identity to the amino acid sequence set forth in SEQ ID NO:8 and/or (b) a light chain variable domain that includes an amino acid sequence having at least 90, 91, 92, 93, 94, 95, 96, 97, 98, or 99 percent identity to the amino acid sequence set forth in SEQ ID NO:16. In some cases, an anti-PAPP-A antibody (or antigen binding fragment) provided herein can include (a) a heavy chain variable domain that includes an amino acid sequence having 100 percent identity to the amino acid sequence set forth in SEQ ID NO:8 and/or (b) a light chain variable domain that includes an amino acid sequence having 100 percent identity to the amino acid sequence set forth in SEQ ID NO:16.

In some cases, an anti-PAPP-A antibody (or antigen binding fragment) provided herein having the ability to bind to PAPP-A can include (a) a heavy chain variable domain that includes an amino acid sequence having at least 90 percent identity to the amino acid sequence set forth in SEQ ID NO:8, provided that the heavy chain variable domain includes the amino acid sequences set forth in SEQ ID NOs:1, 2, and 3, and/or (b) a light chain variable domain that includes an amino acid sequence having at least 90 percent identity to the amino acid sequence set forth in SEQ ID NO:16, provided that the light chain variable domain includes the amino acid sequences set forth in SEQ ID NOs:9, 10, and 11. For example, an anti-PAPP-A antibody (or antigen binding fragment) provided herein can include (a) a heavy chain variable domain that includes an amino acid sequence having at least 90, 91, 92, 93, 94, 95, 96, 97, 98, or 99 percent identity to the amino acid sequence set forth in SEQ ID NO:8, provided that the heavy chain variable domain includes the amino acid sequences set forth in SEQ ID NOs:1, 2, and 3, and/or (b) a light chain variable domain that includes an amino acid sequence having at least 90, 91, 92, 93, 94, 95, 96, 97, 98, or 99 percent identity to the amino acid sequence set forth in SEQ ID NO:16, provided that the light chain variable domain includes the amino acid sequences set forth in SEQ ID NOs:9, 10, and 11.

In some cases, an anti-PAPP-A antibody (or antigen binding fragment) provided herein can include (a) a heavy chain variable domain having the amino acid sequence set forth in SEQ ID NO:8 or the amino acid set forth in SEQ ID NO:8 with one, two, three, four, five, six, seven, eight, nine, or 10 amino acid modifications (e.g., amino acid substitutions, amino acid deletions, and/or amino acid additions) and/or (b) a light chain variable domain that includes the amino acid sequence set forth in SEQ ID NO:16 or the amino acid set forth in SEQ ID NO:16 with one, two, three, four, five, six, seven, eight, nine, or 10 amino acid modifications (e.g., amino acid substitutions, amino acid deletions, and/or amino acid additions). For example, an antibody or antigen binding fragment provided herein can include a heavy chain variable domain having the amino acid sequence set forth in SEQ ID NO:8 with one, two, three, four, five, six, seven, eight, nine, or 10 amino acid modifications (e.g., amino acid substitutions, amino acid deletions, and/or amino acid additions), provided that the heavy chain variable domain includes the amino acid sequences set forth in SEQ ID NOs:1, 2, and 3, and can include a light chain variable domain having the amino acid sequence set forth in SEQ ID NO:16 with one, two, three, four, five, six, seven, eight, nine, or 10 amino acid modifications (e.g., amino acid substitutions, amino acid deletions, and/or amino acid additions), provided that the light chain variable domain includes the amino acid sequences set forth in SEQ ID NOs:9, 10, and 11.

In some cases, an anti-PAPP-A antibody (or antigen binding fragment) provided herein can include (a) a heavy chain variable domain comprising (i) a CDR1 that comprises, consists essentially of, or consists of the amino acid sequence set forth in SEQ ID NO:1, (ii) a CDR2 that comprises, consists essentially of, or consists of the amino acid sequence set forth in SEQ ID NO:2, and (iii) a CDR3 that comprises, consists essentially of, or consists of the amino acid sequence set forth in SEQ ID NO:3, and/or (b) a light chain variable domain comprising (i) a CDR1 that comprises, consists essentially of, or consists of the amino acid sequence set forth in SEQ ID NO:9, (ii) a CDR2 that comprises, consists essentially of, or consists of the amino acid sequence set forth in SEQ ID NO:10, and (iii) a CDR3 that comprises, consists essentially of, or consists of the amino acid sequence set forth in SEQ ID NO: 11. As used herein, a "CDR1 that consists essentially of the amino acid sequence set forth in SEQ ID NO:1" is a CDR1 that has zero, one, or two amino acid substitutions within SEQ ID NO:1, that has zero, one, two, three, four, or five amino acid residues directly preceding SEQ ID NO:1, and/or that has zero, one, two, three, four, or five amino acid residues directly following SEQ ID NO:1, provided that the anti-PAPP-A antibody (or antigen binding fragment) maintains its basic ability to bind to PAPP-A.

As used herein, a "CDR2 that consists essentially of the amino acid sequence set forth in SEQ ID NO:2" is a CDR2 that has zero, one, or two amino acid substitutions within SEQ ID NO:2, that has zero, one, two, three, four, or five amino acid residues directly preceding SEQ ID NO:2, and/or that has zero, one, two, three, four, or five amino acid residues directly following SEQ ID NO:2, provided that the anti-PAPP-A antibody (or antigen binding fragment) maintains its basic ability to bind to PAPP-A.

As used herein, a "CDR3 that consists essentially of the amino acid sequence set forth in SEQ ID NO:3" is a CDR3 that has zero, one, or two amino acid substitutions within SEQ ID NO:3, that has zero, one, two, three, four, or five amino acid residues directly preceding SEQ ID NO:3, and/or that has zero, one, two, three, four, or five amino acid residues directly following SEQ ID NO:3, provided that the anti-PAPP-A antibody (or antigen binding fragment) maintains its basic ability to bind to PAPP-A.

As used herein, a "CDR1 that consists essentially of the amino acid sequence set forth in SEQ ID NO:9" is a CDR1 that has zero, one, or two amino acid substitutions within SEQ ID NO:9, that has zero, one, two, three, four, or five amino acid residues directly preceding SEQ ID NO:9, and/or that has zero, one, two, three, four, or five amino acid residues directly following SEQ ID NO:9, provided that the anti-PAPP-A antibody (or antigen binding fragment) maintains its basic ability to bind to PAPP-A.

As used herein, a "CDR2 that consists essentially of the amino acid sequence set forth in SEQ ID NO:10" is a CDR2 that has zero, one, or two amino acid substitutions within SEQ ID NO:10, that has zero, one, two, three, four, or five amino acid residues directly preceding SEQ ID NO:10, and/or that has zero, one, two, three, four, or five amino acid residues directly following SEQ ID NO:10, provided that the anti-PAPP-A antibody (or antigen binding fragment) maintains its basic ability to bind to PAPP-A.

As used herein, a "CDR3 that consists essentially of the amino acid sequence set forth in SEQ ID NO:11" is a CDR3 that has zero, one, or two amino acid substitutions within SEQ ID NO:11, that has zero, one, two, three, four, or five amino acid residues directly preceding SEQ ID NO:11, and/or that has zero, one, two, three, four, or five amino acid residues directly following SEQ ID NO:11, provided that the anti-PAPP-A antibody (or antigen binding fragment) maintains its basic ability to bind to PAPP-A.

When designing a single chain antibody (e.g., a scFv) having a heavy chain variable domain (or region) and a light chain variable domain (or region), the two regions can be directly connected or can be connected using any appropriate linker sequence. For example, the heavy chain variable region of FIG. 17A can be directly connected to the light chain variable region of FIG. 17B, or the heavy chain variable region of FIG. 17A can be connected to the light chain variable region of FIG. 17B via a linker sequence. In another example, the heavy chain variable domain of FIG. 19A can be directly connected to the light chain variable domain of FIG. 19B, or the heavy chain variable domain of FIG. 19A can be connected to the light chain variable domain of FIG. 19B via a linker sequence. An example of a linker sequence that can be used to connect a heavy chain variable domain (or region) and a light chain variable domain (or region) to create a scFv includes, without limitation, the linker set forth in FIG. 18. See, also, Chen et al., *Adv. Drug Deliv Rev.,* 65(10):1357-1369 (2013).

As indicated herein, the amino acid sequences described herein can include amino acid modifications (e.g., the articulated number of amino acid modifications). Such amino acid modifications can include, without limitation, amino acid substitutions, amino acid deletions, amino acid additions, and combinations. In some cases, an amino acid modification can be made to improve the binding and/or contact with an antigen and/or to improve a functional activity of an anti-PAPP-A antibody (or antigen binding fragment) provided herein. In some cases, an amino acid substitution side chain. Examples of non-conservative substitutions include, without limitation, substituting (a) a hydrophilic residue (e.g., serine or threonine) for a hydrophobic residue (e.g., leucine, isoleucine, phenylalanine, valine, or alanine); (b) a cysteine or proline for any other residue; (c) a residue having a basic side chain (e.g., lysine, arginine, or histidine) for a residue having an acidic side chain (e.g., aspartic acid or glutamic acid); and (d) a residue having a bulky side chain (e.g., phenylalanine) for glycine or other residue having a small side chain.

Methods for generating an amino acid sequence variant (e.g., an amino acid sequence that includes one or more modifications with respect to an articulated sequence identifier) can include site-specific mutagenesis or random mutagenesis (e.g., by PCR) of a nucleic acid encoding the antibody or fragment thereof. See, for example, Zoller, *Curr. Opin. Biotechnol.* 3: 348-354 (1992). Both naturally occurring and non-naturally occurring amino acids (e.g., artificially-derivatized amino acids) can be used to generate an amino acid sequence variant provided herein.

A representative number of anti-PAPP-A antibodies (or antigen binding fragments) are further described in Table 1.

TABLE 1

| | | | | | | |
|---|---|---|---|---|---|---|
| Representative number of anti-PAPP-A antibodies (or antigen binding fragments). | | | | | | |
| Name (Antibody type) | SEQ ID NOs of Heavy Chain Variable Domain/Region CDRs | SEQ ID NOs of Heavy Chain Variable Domain/Region Framework Regions | SEQ ID NO of Heavy Chain Variable Domain/Region | SEQ ID NOs of Light Chain Variable Domain/Region n CDRs | SEQ ID NOs of Light Chain Variable Domain/Region Framework Regions | SEQ ID NO of Light Chain Variable Domain/Region |
| Humanized mAb-PA 1/41 (mAb) | 1, 2, 3 | 4, 5, 6, 7 | 8 | 9, 10, 11 | 12, 13, 14, 15 | 16 |
| Murine mAb-PA 1/41 (mAb) | | | 17 | | | 18 |
| PAC-1 (scFv) | | | 19 | | | 20 |
| PAC-2 (scFv) | | | 22 | | | 23 |
| PAC-5 (scFv) | | | 24 | | | 25 |
| PAC-1-D8 (scFv) | | | 26 | | | 27 | within an articulated sequence identifier can be a conservative amino acid substitution. For example, conservative amino acid substitutions can be made by substituting one amino acid residue for another amino acid residue having a similar side chain. Families of amino acid residues having similar side chains can include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), non-polar side chains (e.g., alanine, valine, leucine, isoleucine, proline, phenylalanine, methionine, tryptophan), beta-branched side chains (e.g., threonine, valine, isoleucine), and aromatic side chains (e.g., tyrosine, phenylalanine, tryptophan, histidine).

In some cases, an amino acid substitution within an articulated sequence identifier can be a non-conservative amino acid substitution. Non-conservative amino acid substitutions can be made by substituting one amino acid residue for another amino acid residue having a dissimilar In some cases, one or more inhibitors of PAPP-A polypeptide expression or activity can be administered to a mammal once or multiple times over a period of time ranging from days to months. In some cases, one or more inhibitors of PAPP-A polypeptide expression or activity can be formulated into a pharmaceutically acceptable composition for administration to a mammal identified as having polycystic kidney disease to reduce one or more symptoms of polycystic kidney disease within that mammal. For example, a therapeutically effective amount of an inhibitor of PAPP-A polypeptide expression or activity can be formulated together with one or more pharmaceutically acceptable carriers (additives) and/or diluents. A pharmaceutical composition can be formulated for administration in solid or liquid form including, without limitation, sterile solutions, suspensions, sustained-release formulations, tablets, capsules, pills, powders, and granules.

Pharmaceutically acceptable carriers, fillers, and vehicles that may be used in a pharmaceutical composition described herein include, without limitation, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

A pharmaceutical composition containing one or more inhibitors of PAPP-A polypeptide expression or activity can be designed for oral or parenteral (including subcutaneous, intramuscular, intravenous, and intradermal) administration. When being administered orally, a pharmaceutical composition can be in the form of a pill, tablet, or capsule. Compositions suitable for parenteral administration include aqueous and non-aqueous sterile injection solutions that can contain anti-oxidants, buffers, bacteriostats, and solutes that render the formulation isotonic with the blood of the intended recipient. The formulations can be presented in unit-dose or multi-dose containers, for example, sealed ampules and vials, and may be stored in a freeze dried (lyophilized) condition requiring only the addition of the sterile liquid carrier, for example, water for injections, immediately prior to use. Extemporaneous injection solutions and suspensions may be prepared from sterile powders, granules, and tablets.

In some cases, a pharmaceutically acceptable composition including one or more inhibitors of PAPP-A polypeptide expression or activity can be administered locally or systemically. For example, a composition provided herein can be administered locally by intravenous injection or blood infusion. In some cases, a composition provided herein can be administered systemically, orally, or by injection to a mammal (e.g., a human).

Effective doses can vary depending on the severity of the polycystic kidney disease, the route of administration, the age and general health condition of the subject, excipient usage, the possibility of co-usage with other therapeutic treatments, and the judgment of the treating physician.

An effective amount of a composition containing one or more inhibitors of PAPP-A polypeptide expression or activity can be any amount that reduces one or more symptoms of polycystic kidney disease within a mammal having polycystic kidney disease without producing significant toxicity to the mammal. For example, an effective amount of an inhibitor of PAPP-A polypeptide expression or activity (e.g., an anti-PAPP-A antibody) can be from about 0.25 mg/kg to about 100 mg/kg (e.g., from about 0.3 mg/kg to about 11 mg/kg, from about 1 mg/kg to about 10 mg/kg, from about 2 mg/kg to about 10 mg/kg, from about 5 mg/kg to about 10 mg/kg, from about 6 mg/kg to about 10 mg/kg, from about 6 mg/kg to about 8 mg/kg, or from about 7 mg/kg to about 9 mg/kg). In some cases, from about 100 mg to about 1000 mg (e.g., from about 100 mg to about 250 mg, from about 125 mg to about 275 mg, from about 250 mg to about 1000 mg, from about 300 mg to about 1000 mg, from about 400 mg to about 1000 mg, from about 100 mg to about 900 mg, from about 100 mg to about 800 mg, from about 400 mg to about 800 mg, or from about 500 mg to about 700 mg) of an inhibitor of PAPP-A polypeptide expression or activity can be administered to an average sized human (e.g., about 75-85 kg human) per administration (e.g., per daily or weekly administration) for about two to about twelve weeks.

In some cases, an inhibitor can be administered daily within one of these dose ranges for a period of time (e.g., 14 or 21 days) followed by a seven-day rest period.

If a particular mammal fails to respond to a particular amount, then the amount of an inhibitor of PAPP-A polypeptide expression or activity (e.g., an anti-PAPP-A antibody) can be increased by, for example, two fold. After receiving this higher amount, the mammal can be monitored for both responsiveness to the treatment and toxicity symptoms, and adjustments made accordingly. The effective amount can remain constant or can be adjusted as a sliding scale or variable dose depending on the mammal's response to treatment. Various factors can influence the actual effective amount used for a particular application. For example, the frequency of administration, duration of treatment, use of multiple treatment agents, route of administration, and severity of the condition (e.g., polycystic kidney disease) may require an increase or decrease in the actual effective amount administered.

The frequency of administration of an inhibitor of PAPP-A polypeptide expression or activity (e.g., an anti-PAPP-A antibody) can be any amount that reduces the symptoms of polycystic kidney disease without producing significant toxicity to the mammal. For example, the frequency of administration of an inhibitor of PAPP-A polypeptide expression or activity can be from about once a day to about once a month (e.g., from about once a week to about once every other week). The frequency of administration of an inhibitor of PAPP-A polypeptide expression or activity can remain constant or can be variable during the duration of treatment. A course of treatment with a composition containing an inhibitor of PAPP-A polypeptide expression or activity can include rest periods. For example, a composition containing one or more inhibitors of PAPP-A polypeptide expression or activity can be administered daily over a two-week period followed by a two-week rest period, and such a regimen can be repeated multiple times. As with the effective amount, various factors can influence the actual frequency of administration used for a particular application. For example, the effective amount, duration of treatment, use of multiple treatment agents, route of administration, and severity of the condition (e.g., polycystic kidney disease) may require an increase or decrease in administration frequency.

An effective duration for administering a composition containing one or more inhibitors of PAPP-A polypeptide expression or activity (e.g., an anti-PAPP-A antibody) can be any duration that reduces the symptoms of polycystic kidney disease within a mammal identified as having polycystic kidney disease without producing significant toxicity to the mammal. In some cases, the effective duration can vary from several days to several months. In general, the effective duration for reducing the symptoms of polycystic kidney disease within a mammal identified as having polycystic kidney disease can range in duration from about six weeks to about six months. Multiple factors can influence the actual effective duration used for a particular treatment. For example, an effective duration can vary with the frequency of administration, effective amount, use of multiple treatment agents, route of administration, and severity of the condition being treated.

In some cases, an inhibitor of PAPP-A polypeptide expression or activity (e.g., an anti-PAPP-A antibody) can be used in combination with one or more other treatments of polycystic kidney disease such as JYNARQUE® (tolvaptan), or in combination with adjunct therapies such as medications to control pain or manage blood pressure. The inhibitor of PAPP-A polypeptide expression or activity and other treatments can be administered together (e.g., formulated together), or the inhibitor of PAPP-A polypeptide expression or activity (e.g., an anti-PAPP-A antibody) can be administered concurrently with, prior to, or subsequent to, one or more other treatments. The particular combination of therapies to employ in a combination regimen will take into account compatibility of the desired therapeutics and the desired therapeutic effect to be achieved. It also will be appreciated that the therapies employed may achieve a desired effect for the same disorder or they may achieve different effects (e.g., control of any adverse effects).

In some cases, an inhibitor of PAPP-A polypeptide expression or activity (e.g., an anti-PAPP-A antibody) can be used to treat polycystic kidney disease as the sole active ingredient.

The invention will be further described in the following examples, which do not limit the scope of the invention described in the claims.

EXAMPLES

Example 1—Treating Kidney Diseases

Animal Studies

The Pkd1$^{RC/RC}$ (PKD1 p.R3277C) and Pkd2$^{WS25/-}$ murine models of ADPKD (Hopp, et al., *J. Clin. Invest.* 122, 4257-4273 (2012)) were used. PAPP-A deficient ADPKD mice were generated by crossing PAPP-A deficient Pappa$^{/m1Cac}$ mice (Conover, et al., Development 131, 1187-1194 (2004)) with the Pkd1$^{RC/RC}$ mice. Pkd1$^{RC/RC}$ mice were crossed with Prkar1a$^{f/f}$; Pkhd1-Cre mice to generate ADPKD mice with kidney-specific over-activation of PKA (Ye, et al., *American Journal of Physiology—Renal Physiology* 313, F677-F686 (2017)). C57BL/6J mice were purchased from the Jackson Laboratory. Animals were housed in standard cages (5 mice per cage) in animal housing room maintained at constant temperature and humidity with 12 h light/dark cycles. All animal experimental protocols were approved by the Institutional Animal Care and Use Committee at Mayo Clinic (Protocol no. A47715), and studies were conducted in accordance with the NIH Guide for the Care and Use of Laboratory Animals. Both male and female mice were used for the studies.

For PAPP-A antibody experiments, C57BL/6J and Pkd1$^{RC/RC}$ mice were given weekly intraperitoneal (i.p.) injections of 30 mg/kg mAb-PA (Ansh Labs) (Becker, et al., *Molecular Cancer Therapeutics* 14, 973-981 (2015)) or control IgG (R&D Systems) for 6 weeks. For forskolin (FSK) studies, a single dose of FSK (5 mg/kg) or vehicle control (5% DMSO) was administered by i.p. injection. For IGF-1 antibody experiment, the animals were injected intraperitoneally with 0.2 mg/kg IGF-1 antibody or IgG control (R&D Systems) per week for 6 weeks.

Blood was collected for biochemical analysis, and organs were weighed. Portions of tissue were placed in formalin and processed for histological studies or snap frozen in liquid nitrogen and stored at −80° C. for protein or gene expression analysis.

Reagents and Antibodies

All reagents and chemicals were purchased from Sigma-Aldrich, unless specified. Recombinant human IGF-I and IGFBP4 were from R&D systems (R&D systems, Inc.). Antibodies to pERK (#4370), ERK (#4695), pAkt (#4060), Akt(#4691) were purchased from Cell Signaling. PCNA (#sc-7907) antibody was from Santa Cruz Biotechnology.

PAPP-A antibodies for Western (polyclonal) and immunostaining (monoclonal, C8) were provided by Dr. Claus Oxvig.

Histological and Immunohistochemical Analysis

Formalin-fixed paraffin-embedded tissues were cut into 5 µm thick cross-sections and stained with hematoxylin-eosin (H&E) by the Mayo Histology Core Laboratory for cystic index analysis. Cystic index (cyst area proportional to cross-sectional kidney area) was measured as described earlier. Warner, et al., *J. Am. Soc. Nephrol.* 27, 1437-1447 (2016). Immunostaining for CD3 was performed using anti-CD3 antibody (1:100, Agilent Technologies). Fibrosis was assessed by Sirius Red staining. Percent positive fibrosis and anti-CD3 areas were calculated using ImageJ.

Human ADPKD kidney tissue slides were received from Dr. Torres under Institutional approved IRB protocol and normal human kidney tissue slides were purchased from Novus Biologicals.

Western Blot

Western blot analysis on kidney tissues and cultured cells was performed as described by Warner et al., 2016, supra. Antibodies against LC3 (4108), p62 (#5114) cleaved caspase 3, pERK (#4370), ERK (#4695), pAkt (#4060), Akt (#4691) were used and purchased from Cell signaling. Membranes were stripped and probed with tubulin or GAPDH antibody to control for equal gel loading and transfer. Films were scanned and densitometry was performed using ImageJ.

Real Time Polymerase Chain Reaction

Total RNA was isolated using the RNeasy Plus Mini Kit (Qiagen) and cDNA was prepared using the QuantiTect Reverse Transcription Kit (Qiagen) or High Capacity cDNA Reverse Transcription Kit (Applied Biosystems). Commercially available TaqMan gene expression probes were obtained from Applied Biosystems and quantitative real-time PCR was performed in duplicates as described by Warner et al., 2016, supra. The relative mRNA expression of target genes was calculated using the $2^{-ddCq}$ method with Gapdh as internal reference gene.

PAPPA Mediated IGFBP4 Proteolysis Assay

The PAPP-A mediated IGFBP4 proteolysis assay in RCTE and 9-12 cells was performed as described by Bale, et al. Growth Hormone & IGF Research 42-43, 1-7 (2018). Briefly, human IGFBP4 pre-complexed with IGF-II was incubated in cell-free conditioned medium with or without inhibitory PAPP-A monoclonal antibody (mAb-PA 1/41) for 72 hours at 37° C. For in vivo determination of PAPP-A activity, human IGFBP4 pre-complexed with or without IGF-II was incubated with kidney membrane fractions for 72 hrs at 37° C. Western blot and quantitative analysis was done as described by Bale, et al., 2018, supra.

Serum IGF-1 Levels

Serum was collected from C57BL6 WT and Pkd1$^{RC/RC}$ mice and stored at −80° C. The amounts of IGF-1 in the serum were measured using the Ultra-Sensitive Mouse IGF-1 ELISA kit from Crystal Chem. Inc., according to the manufacturer instructions.

Cystatin C Measurements

Blood was collected from the posterior Vena Cava into heparinized tubes at the time of sacrifice and plasma was separated out by centrifugation. Plasma cystatin C levels were assessed using a Mouse/Rat Cystatin C Quantikine ELISA Kit (R&D Systems) according to the manufacturer's instructions.

Metanephroi Culture

Metanephros organ culture was performed as described by Barak and Boyle, Organ Culture and Immunostaining of Mouse Embryonic Kidneys. Cold Spring Harbor Protocols 2011, pdb.prot5558 (2011). The metanephroi were isolated from C57BL6/J mice at embryonic day 13.5 and placed on transparent Falcon 0.4 µm cell culture inserts in 12-well plates (Fisher Scientific) at 37° C. in a humidifier incubator (5% CO2) in serum free media. Metanephroi were grown in DMEM/F12 media supplemented with 5 µg/ml transferrin, 2.8 nM selenium, 25 ng/ml prostaglandin E1, 6 ng/ml T3, 1% penicillin/streptomycin, and 5-10 µg/ml insulin for 10 days and media was changed every 2 days. Cysts were generated by treating with FSK (10 µM) and development of cysts was observed every day. IGF-1 (100 6.5 nM), IGFBP4 (26 nM) and PAPP-A (320 µM) were added to the culture after 4 hours treatment with FSK.

Cell Culture

RCTE and 9-12 cells were cultured in DMEM:F12 with 10% FBS and 1% penicillin/streptomycin. Cells were treated with 10 µM FSK, 200 µM 6-MB-cAMP, or 30 µM 8CPT2OMe for 16 hours and RNA was isolated. Cells were also treated with 10 µM FSK in the presence or absence of 100 µM Rp cAMPS for 16 hours or different dosage of KG-501 and RNA was isolated. RCTE and 9-12 cells were also treated with 10 µM CBP30 for 24 hours followed by RNA isolation. PAPP-A protein levels in cell free conditioned medium and also in human cystic fluid (received from Dr. Torres) was measured with picoPAPP-A ELISA kit, from AnshLabs (AnshLabs, Webster, Tex.).

In some experiments, RCTE and 9-12 cells were cultured in DMEM:F12 with 10% FBS and 1% penicillin/streptomycin. Cells were treated with 10 µM FSK, IL1β (5 ng/ml), IL-2 (2 ng/ml), EGF (10 ng/ml) or TGFβ (1 ng/ml) for 16 hour and RNA was isolated. RCTE and 9-12 cells were also treated with vasopressin (10 nM) or vasopressin analogue DD-AVO (10 nM) for 16 hours followed by RNA isolation.

Madin-Darby canine kidney (MDCK) cells were maintained in DMEM/F12 (Life Technologies) supplemented with 10% fetal bovine serum (FBS) and penicillin and streptomycin (Invitrogen). Cystogenesis studies with MDCK cells were performed essentially as described by Mangoo-Karim, et al., *Proc. Natl. Acad. Sci.* 86, 6007-6011 (1989). Briefly, cells were suspended in collagen I solution, seeded in 24-well plates at 4,000 cells per well, and incubated at 37° C. for 30-45 min. for collagen to polymerize. Cells were then given medium (DMEM/F12, 1% FBS) containing the cAMP agonist forskolin (FSK, 10 µM) and IGF-1 (10 ng/ml). Cells were cultured for 14 days, with media change every other day. At the end of the study, the number of cysts in each well was counted.

Statistical Analysis

Data are expressed as means±SEM. Comparisons were made by unpaired Student's t-test and analysis of variance (ANOVA). Nonparametric tests were used wherever required by data distribution. Significance was set at $P<0.05$.

Results

PAPP-A Levels Increase with the Progression of Cystic Disease

The IGF pathway is complex and has several components including IGF itself, IGFBPs, the IGF receptor and the IGFBP-cleaving enzymes such as the pappalysins (PAPP-A and PAPP-A2). See, for example, Zhou, et al., *J. Endocrinol.* 178, 177-193 (2003); Oxvig, *J. Cell Commun. Signal.* 9, 177-187 (2015); and Conover, *Trends Endocrinology & Metabolism* 23, 242-249 (2012).

As a first step to directly investigate if the IGF-1 pathway is involved in the pathogenesis of ADPKD, the renal expression of components of the IGF-1 pathway were evaluated in the Pkd1$^{RC/RC}$ murine model of ADPKD. Using real time polymerase chain reaction analysis (RT-PCR), an upregulation in several IGF-1 pathway genes was observed in the kidney of the Pkd1$^{RC/RC}$ mice, including Igf1, Igf1r, and Igfbp5. The greatest induction, approximately 8-fold, was observed with Pappa, the enzyme responsible for increasing IGF-1 bioavailability through cleavage of ligand-bound IGFBP4 (FIG. 1A). IGFBP5 expression has been shown to be regulated by IGF-1 availability and as an in vivo marker of IGF-1 signaling. See, Swindell, et al., *Experimental Gerontology* 45, 366-374 (2010); Adamo, et al., *Endocrinology* 147, 2944-2955 (2006); and Resch, et al., *Endocrinology* 147, 5634-5640 (2006).

To determine if increased PAPP-A expression may play an active role in the pathogenesis and progression of ADPKD, it was assessed whether Pappa mRNA expression correlated with pathological parameters such as kidney size and cystic index. A strong positive correlation between Pappa and kidney weight with an $R^2=0.9$ was observed (FIG. 1B). In addition, an apparent positive correlation existed between PAPP-A expression or kidneys/heart weight ratio with markers of inflammation, renal injury and fibrosis (FIG. 2A-G). These data suggest that Pappa expression is concomitant with the progression of cystic disease, and may be directly associated with the growth and expansion of the cysts in ADPKD at a threshold that correlates with tissues injury, inflammation and fibrosis.

PAPP-A is ubiquitously expressed in several organs in humans and is highly expressed in human placenta during pregnancy. See, for example, Bonno, et al., *Lab Invest.* 71, 560-566 (1994). To examine whether the increase in Pappa expression is specific to the kidney in ADPKD, the Pappa mRNA levels were compared in several tissues of 6 month-old WT and Pkd1$^{RC/RC}$ mice, including brain, lung, heart, liver, spleen, muscle, and fat. Interestingly, Pappa mRNA levels were elevated only in the kidneys, but not in other organs of Pkd1$^{RC/RC}$ mice (FIGS. 1A and C), suggesting that the increase in PAPP-A production is indeed specific to ADPKD kidneys. This observation further supports the idea that, in ADPKD, the increase in expression of PAPP-A could cleave IGFBPs and thus increase the availability of free IGF-1 to bind to its receptor specifically in the kidney, promoting cellular proliferation and tissue growth. Interestingly it was found that FR, which slowed cyst progression in Pkd1$^{RC/RC}$ mice, also decreased renal Pappa expression to normal levels (FIG. 2D), further strengthening the hypothesis that PAPP-A may play a key role in pathogenesis of ADPKD, Next, to determine whether the increase in PAPP-A levels is a common feature of ADPKD, Pappa mRNA expression levels were measured in a second murine model of ADPKD, the Pkd2$^{WS25/-}$. It was found that, akin to the Pkd1$^{RC/RC}$ Pappa expression was also increased in the kidney of the Pkd2$^{WS25/-}$ mice, suggesting that PAPP-A could be a component of the pathogenesis of ADPKD in both murine models (FIG. 1D).

To summarize, the ADPKD mouse model deficient in PAPP-A showed a significant reduction in kidney size and cystic burden, with a remarkable reduction in renal inflammation, injury and fibrosis compared to ADPKD mice. Furthermore, there was a significant reduction in kidney injury in ADPKD-PAPP-A KO mice, clearly demonstrating a role for PAPP-A in the pathogenesis of experimental ADPKD. The reduction in the cystic burden appeared to be mediated by reduction in proliferation, not apoptosis or autophagy.

It was further investigated whether PAPP-A is increased in human ADPKD. Renal cystic fluid from ADPKD patients was assessed for secreted PAPP-A using an enzyme-linked immunosorbent assay (ELISA), and found to contain significantly more PAPP-A than reference levels for normal serum (FIG. 1E). Next, paraffin-embedded kidney sections from ADPKD patients and normal controls were probed with a polyclonal antibody against PAPP-A to determine the anatomical localization of expression. PAPP-A was found to be highly expressed on the cystic epithelia and renal tubules of ADPKD patients (FIG. 1F). In contrast, normal kidney sections showed a diffused low level expression of PAPP-A (FIG. 1F). In vitro experiments with human ADPKD cystic epithelial cells derived from ADPKD patients also demonstrated higher PAPP-A protein expression compared to normal human renal cortical tubular epithelial cells (RCTE) (FIG. 1G). These findings indicate that PAPP-A is produced in the kidney in human ADPKD as well, is present in cystic epithelia, and secreted into the cystic fluid.

cAMP Pathway Induces PAPP-A Expression in ADPKD

While the above findings of increased PAPP-A expression in ADPKD suggest its potential role in the pathogenesis of this cystic disease, little is known about the mechanisms that regulate PAPP-A expression in the kidney. To understand these mechanisms, potential pathways were explored that could regulate the PAPP-A expression in ADPKD.

Reduction of polycystin 1/polycystin 2 in ADPKD disrupt intracellular calcium homeostasis, resulting in a subsequent increase of intracellular cAMP levels in the kidney. cAMP has been shown to mediate cyst formation and promote fluid secretion, thus playing a central role in various signaling pathways leading to the pathogenesis of ADPKD. See, for example, Magenheimer, et al., J. Am. Soc. Nephrol. 17, 3424-3437 (2006); Torres, et al., *Nature Medicine* 10, 363 (2004); Sutters, et al., *Kidney International* 60, 484-494 (2001); and Torres, et al., *J. Am. Soc. Nephrol.* 25, 18-32 (2014). Interestingly, in non-kidney cells (choriocarcinoma cell line, it has been shown that the cAMP pathway stimulates PAPP-A mRNA expression (Haaning, et al., *Eur. J. Biochem.* 237, 159-163 (1996). However, the precise mechanism by which cAMP stimulates PAPP-A expression has not been determined thus far.

Figure 3:
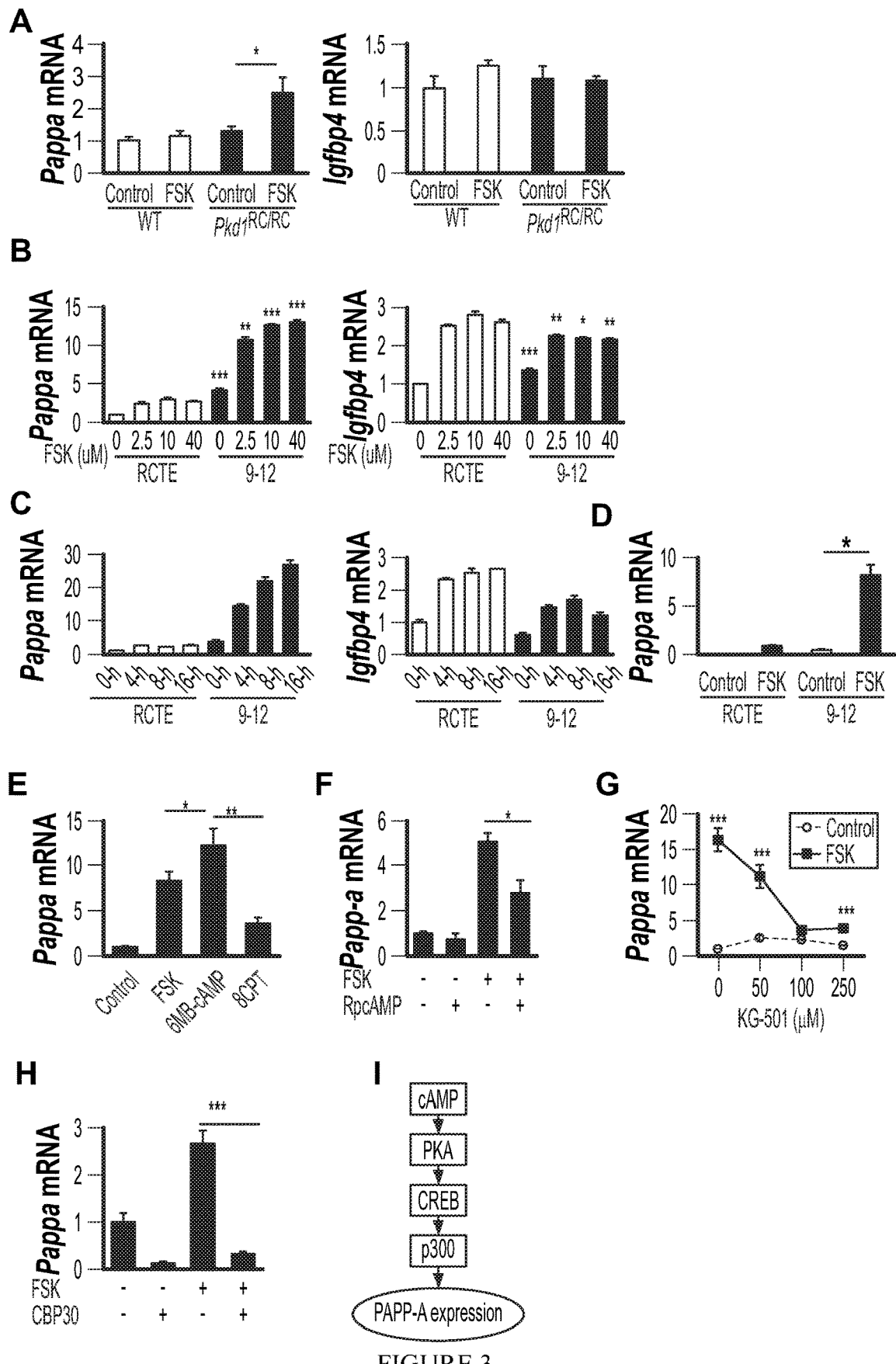
FIG. 3. Molecular pathways involved in regulation of PAPP-A expression. (A) Pappa mRNA levels in kidneys of Pkd1$^{RC/RC}$ (n=5) and WT (n=4) mice treated with vehicle (5% DMSO) or 5 mg/kg FSK for 24 hours at 4 weeks of age. (B-C) Pappa and Igfbp4 mRNA levels in RCTE and PKD cystic epithelial cells (9-12) treated with (B) increasing doses of FSK for 4 hours and (C) 10 μM FSK for various time intervals. (D) ELISA analysis of PAPPA levels in cell-free conditioned media of RCTE and 9-12 cells treated with 10 μM FSK or vehicle for 72 hours. (E-H) Pappa mRNA expression in 9-12 cells treated with: (E) vehicle control (0.1% DMSO), 10 μM FSK, a selective activator of protein kinase A (6-MB-cAMP, 200 μM) or Epac (8CPT2OMe, 30 μM) for 16 hours, (F) 10 μM FSK in the presence or absence of a competitive antagonist of cAMP (Rp cAMP, 100 μM) for 16 hours, (G) 10 uM FSK in the presence or absence of the indicated doses of KG-501 which blocks cAMP-induction of CREB for 16 hours, (H) a selective CBP/p300 bromodomain inhibitor (CBP30, 10 μM) for 24 hours followed by 10 μM FSK for 16 hours. (I) Schematic representation of cAMP-induced PAPP-A expression. Data are mean±SEM. *P<0.05, P<0.01, *P<0.001 compared to control.

To investigate whether cAMP plays a role in the regulation of PAPP-A expression in ADPKD, the effect of the cAMP-stimulating agent forskolin (FSK) was examined on renal Pappa expression in vivo in Pkd1$^{RC/RC}$ and WT control mice at 4 weeks of age, when the Pappa mRNA expression levels are not elevated. Twenty-four hours after injection with FSK (5 mg/kg) or DMSO, kidneys were isolated and gene expression was measured using RT-PCR. FSK induced a significant increase in renal Pappa mRNA in the Pkd1$^{RC/RC}$, but not in WT mice, while expression levels of Igfbp4, Igfbp5, and Igf1r were similar in both groups (FIG. 3A, 4A). This indicates that cAMP could be a potent stimulator of the renal PAPP-A expression in ADPKD.

Figure 4:
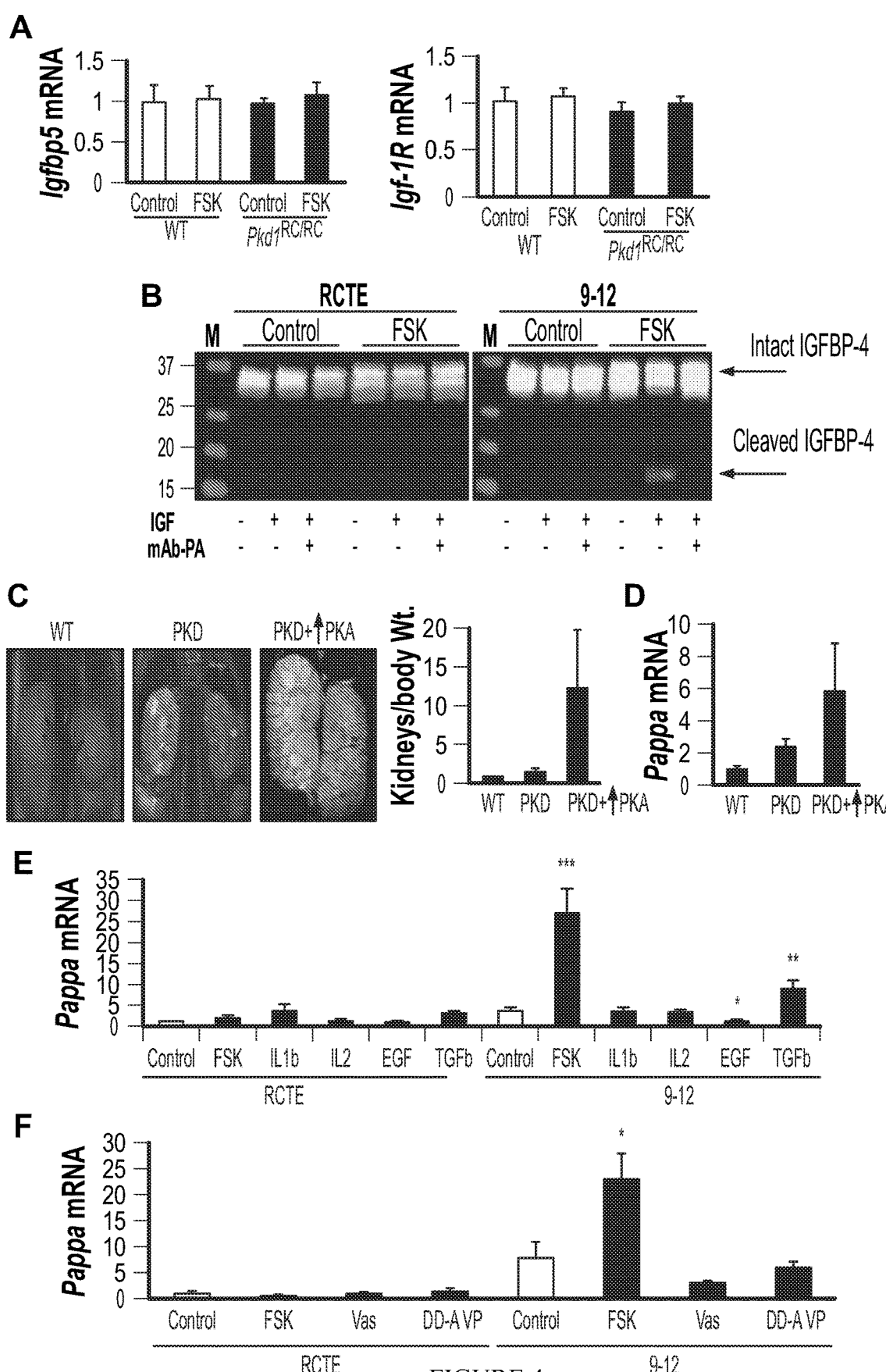
FIG. 4. cAMP pathway induces PAPP-A expression in ADPKD. (A) mRNA expression levels of Igfbp5 and Igf-1R after 24 hours of treatment with vehicle (5% DMSO in PBS) or forskolin (5 mg/kg in 5% DMSO in PBS) in WT (n=4) and Pkd1$^{RC/RC}$ (n=5) mice. (B) Proteolytic assay of PAPP-A mediated IGFBP4 using cell free conditioned media of RCTE and 9-12 cells treated with FSK or vehicle for 72 hours. Conditioned medium was incubated for 72 hours at 37° C. with IGFBP4 without (−) or with (+) pre-complexing to IGF, and without (−) or with (+) the addition of inhibitory mAb-PA 1/41 antibody (also designated mAb-PA for short). Arrows indicate intact and cleaved IGFBP4 bands. (C) Overactivation of PKA exacerbates cystic disease in ADPKD mice. Pkd1$^{RC/RC}$ mice were crossed with Prkar1a$^{f/f}$; Pkhd1-Cre mice to generate ADPKD mice with kidney-specific overactivation of PKA (PKD+↑PKA). Representative MR Images of WT and PKD kidneys at 3 months old compared to PKD+↑PKA at 5 weeks old and graph of Kidneys/body weight comparison at 3 weeks old. (D) Pappa mRNA expression in WT, PKD and PKD+↑PKA kidneys at 5 weeks old. (E) mRNA expression levels of Pappa in RCTE and 9-12 cells treated with FSK (10 μM), IL1β (5 ng/ml), IL-2 (2 ng/ml), EGF (10 ng/ml) or TGFβ (1 ng/ml) for 16 hours. (F) mRNA expression levels of Pappa in RCTE and 9-12 cells treated with FSK (10 μM), vasopressin (10 nM) or vasopressin analogue DD-AVO (10 nM) for 16 hours. Graphs are mean±SEM of n=4 mice/group and for cell experiments, graphs are mean±SEM of two experiments done in triplicates. *P<0.05, P<0.01, *P<0.001 compared to 9-12 control cells.

The mechanism by which cAMP may induce PAPP-A expression in PKD was examined using the 9-12 human ADPKD cells. Upon FSK treatment, PAPP-A mRNA and protein levels were highly induced in 9-12 cells, but not in the RCTE cells derived from normal kidney (FIG. 3B). Furthermore, it was found that FSK increased PAPP-A expression in a dose and time-dependent manner (FIG. 3C). The PAPP-A protein levels were assessed by ELISA in cell-free conditioned media of RCTE and 9-12 cells with and without FSK stimulation, and a significant increase was observed only in 9-12 cells stimulated with FSK (FIG. 3D). Further analysis of the cell-free conditioned media by measurement of PAPP-A-mediated IGFBP-4 proteolysis demonstrated cleavage of IGFBP-4 only in supernatant from FSK-stimulated 9-12 cells, indicating that PAPP-A is proteolytically active in 9-12 cells only. (FIG. 4B). Addition of an inhibitory PAPP-A monoclonal antibody (Mikkelsen, et al., *Oncotarget* 5, 1014-1025 (2014)) blocked proteolytic cleavage of IGFBP4 (FIG. 4).

cAMP acts by activating at least two distinct cAMP-sensitive pathways: protein kinase A (PKA) and the exchange protein directly activated by cAMP (Epac) pathways. To determine whether PAPP-A expression in 9-12 cells is activated by the cAMP-PKA and/or cAMP-Epac pathway, the effect of a selective PKA activator 6 MB-cAMP (Vuchak, Molecular Pharmacology 76, 1123-1129 (2009)) and a selective Epac activator 8-CPT-2Me-cAMP (8CPT) (Misra and Pizzo, *J. Cell. Biochem.* 113, 1488-1500 (2012)) were compared with that of the non-specific cAMP agonist FSK. After 16 hours of treatment, 6 MB-cAMP caused the greatest increase in PAPP-A expression in PKD cells, somewhat higher than that of the cells treated with FSK (FIG. 3E). In contrast, only a small increase in PAPP-A expression was observed in 8CPT-treated PKD cells (FIG. 3E). The role of the PKA pathway in induction of PAPP-A was further assessed in 9-12 cells using the PKA inhibitor Rp-cAMPS (Gjertsen, et al., *J. Biol. Chem.* 270, 20599-20607 (1995)). It was found that inhibition of PKA significantly decreased FSK-induced PAPP-A expression in the PKD cells (FIG. 3F), suggesting that cAMP might induce PAPP-A expression through activation of PKA.

Given that the in vivo and in vitro data suggested a role for the PKA pathway in the regulation of PAPP-A in ADPKD, this possibility was further examined in vivo using the Pkd1$^{RC/RC}$ mouse model with kidney-specific overactivation of PKA (Ye, et al., *American Journal of Physiology—Renal Physiology* 313, F677-F686 (2017)). These mice have a collecting duct-specific (Pkhd1-Cre) deletion (Williams, et al., *American journal of physiology. Renal physiology* 307, F356-F368 (2014)) of the PKA regulatory subunit 1a (Prkar1a), whose function is to block PKA catalytic activity. At just 3 weeks, the burden of cystic disease in these mice was clearly increased compared to Pkd1$^{RC/RC}$ mice at 5 weeks with normal PKA activity (FIG. 4C), and an increase in the PAPP-A expression was observed (FIG. 4D), confirming in vivo a role for PKA in the regulation of PAPP-A expression in ADPKD.

The cAMP signaling pathway activates the transcription factor CREB (cAMP response element-binding protein) through PKA. To study the involvement of CREB in cAMP-dependent PAPP-A expression in ADPKD, PKD cells were treated with KG-501, which attenuates the cAMP-dependent gene induction by interacting with the CREB binding groove, which is necessary for CREB:CBP (CREB-binding protein) interaction (Best, et al., *Proc. Natl. Acad Sci. USA* 101, 17622-17627 (2004)). KG-501 decreased the cAMP-induced PAPP-A expression in a dose-dependent manner, which suggested that CREB is involved in PAPP-A regulation (FIG. 3G).

The CREB:CBP/p300 complex binds to the promoter of genes, inducing histone acetylation, which "relaxes" the chromatin and increases target gene expression (Vo and Goodman, *J. Biol. Chem.* 276, 13505-13508 (2001)). It was next investigated whether the interaction between CREB and CBP/p300 activates PAPP-A transcription in ADPKD. CBP30 that preferentially binds to the CBP/p300 bromodomain and blocks gene transcription (Hammitzsch, et al., *Proc. Natl. Acad Sci. USA* 112, 10768-10773 (2015)) was used for this study. The results showed that CBP30 abolished the FSK-induced PAPP-A expression in PKD cells (FIG. 3H) suggesting that the cAMP-PKA-CREB-CBP/p300 pathway mediates PAPP-A expression in ADPKD (FIG. 3I).

In addition to cAMP, several other agents have also been shown to induce PAPP-A expression in non-kidney cells. In 9-12 and RCTE cells, the effect on PAPP-A expression was tested for a battery of agents that have either been shown to induce PAPP-A in other cell types or are known to play a role in the pathogenesis of ADPKD. There was a strong induction of PAPP-A expression only in 9-12 cells, in response to FSK, other cAMP analogues, and TGFβ (FIG. 4E). Surprisingly, PAPP-A expression in 9-12 cells was not induced by any of the other agents tested including EGF, IL-1β, Il-2, vasopressin, and vasopressin analogue DD-AVD (FIG. 4E, F).

Figure 5:
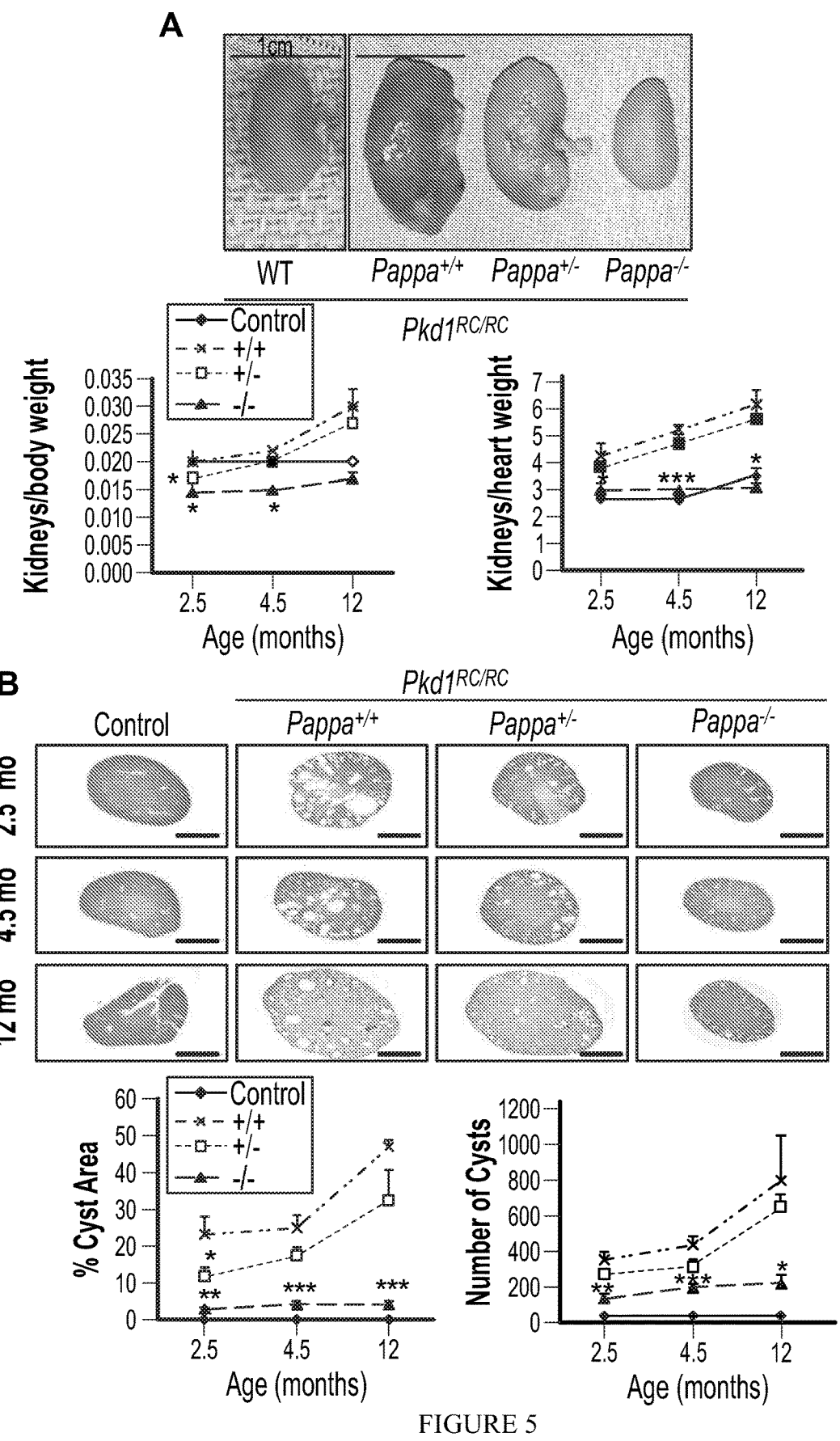
FIG. 5. Genetic deletion of Pappa ameliorates ADPKD. (A-B) Pkd1$^{RC/RC}$ mice that are Pappa$^{+/+}$, Pappa$^{+/+}$, or Pappa$^{-/-}$: (A) Representative gross kidney images at 12 month age and graphs of kidney weight/body weight (left), kidney/heart weight (right) at different ages; (B) H&E kidney section photomicrographs and graphs of cystic area (left), and cyst number (right) compared to WT mice at different ages. Data are mean±SEM of n=4-5 for WT and 5-12 for Pkd1$^{RC/RC}$ Pappa$^{++, +/-, -/-}$. *P<0.05, P<0.01, *P<0.001 compared to Pkd1$^{RC/RC}$-Pappa$^{+/+}$ group.

Genetic Deletion of Pappa in ADPKD Mice Remarkably Reduces the Renal Cystic Burden, Inflammation, Fibrosis and Injury To directly investigate the role of PAPP-A in the progression of cystic disease in ADPKD, an ADPKD mouse model deficient in PAPP-A was generated. These animals were generated by crossing the PAPP-A-deficient $Pappa^{tm1Cac}$ mice (Conover, et al., *Development* 131, 1187-1194 (2004)) with the $Pkd1^{RC/RC}$ mice (Hopp, et al., 2012, supra). $Pkd1^{RC/RC} Pappa^{-/-}$ (ADPKD-PAPP-A$^{-/-}$ knockout, KO) mice were overall healthy with normal behavior. The progression of cystic disease in these mice was characterized at 3 different ages: 2.5, 4.5 and 12 months old. At each age, the kidneys of the ADPKD-PAPP-A KO mice were smaller and healthier in gross appearance compared to ADPKD-PAPPA$^{+/+}$ mice (FIG. 5A, 6A). Remarkably, ADPKD-PAPP-A KO kidneys showed significantly reduced cyst area and, appeared like normal kidneys even at 12 months age as assessed by histological analysis (FIG. 5A, B). Interestingly, ADPKD/PAPP-A$^{+/-}$ kidneys were also partially protected against cystic disease (FIG. 5A, B). A significant decrease in kidney weight was observed as assessed by kidneys/body as well as kidneys/heart weight ratios in ADPKD-PAPP-A KO mice compared to ADPKD-PAPPA$^{+/+}$ (FIG. 5A, FIG. 6B). The cyst area and number of cysts were also significantly decreased in the PKD-PAPP-A KO mice compared to PKD-PAPPA$^{+/+}$ during the course of the disease (FIG. 5B).

Figure 7:
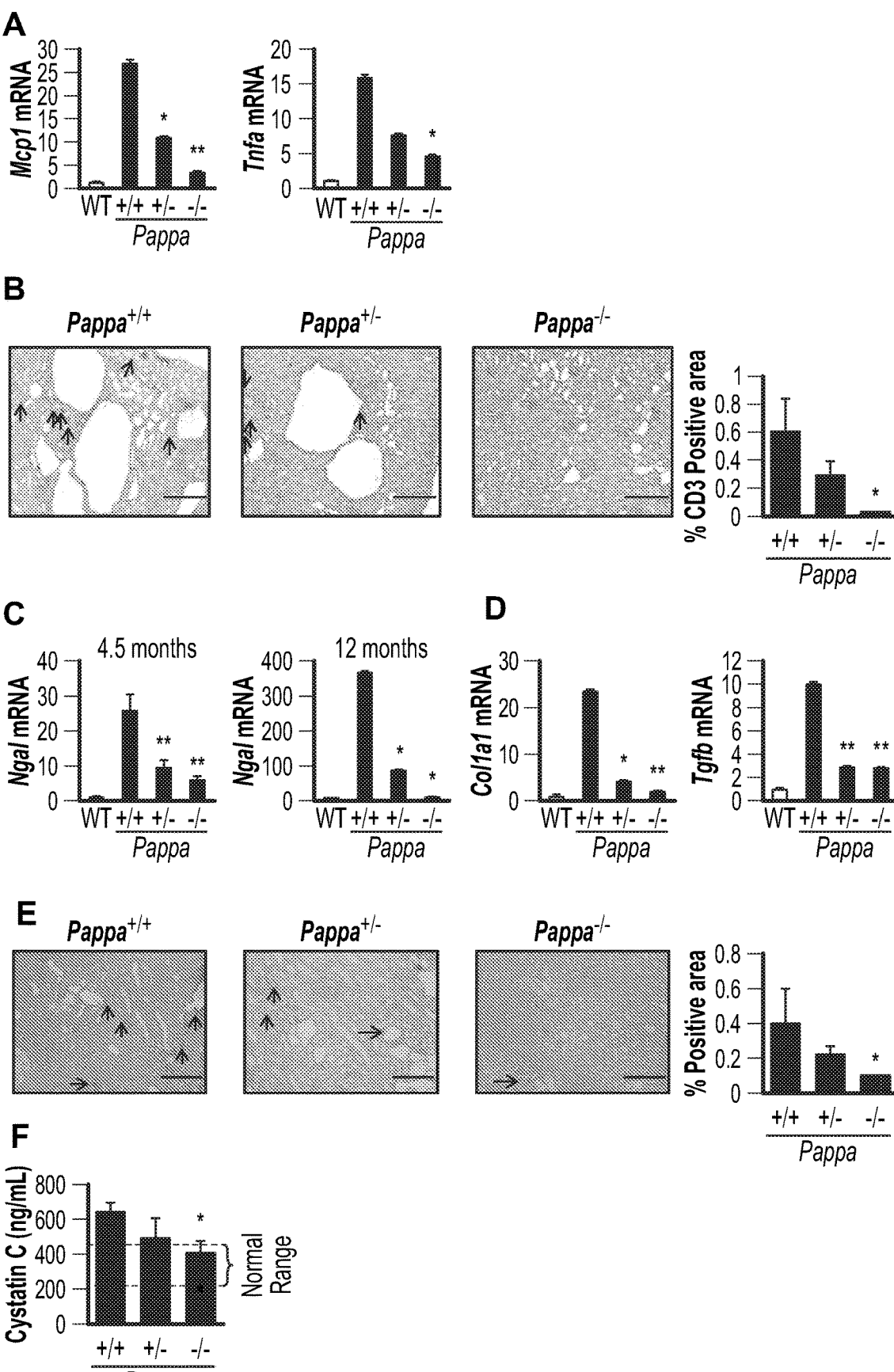
FIG. 7. Genetic deletion of Pappa reduces renal inflammation, injury, and fibrosis in ADPKD mice. (A) Renal Mcp1 and Tnfα mRNA expression in WT (n=4-5) and Pkd1$^{RC/RC}$-Pappa mutants (n=5-12/group) at 12 months of age. (B) Representative photomicrographs showing anti-CD3 immunostaining in kidney sections from 4.5 month old Pkd1$^{RC/RC}$-Pappa mutant mice, and graph showing quantification of positively stained area (n=6 per group). (C) Renal Ngal mRNA expression in WT (n=4-5) and Pkd1$^{RC/RC}$-Pappa mutants (n=5-12/group) at 4.5 months (left) and 12 months (right) of age. (D) Serum cystatin C levels in Pkd1$^{RC/RC}$-Pappa mutant mice at 12 months old age (n=4-8/group). (E) Col1a 1 and Tgfβ mRNA expression in WT (n=4-5) and Pkd1$^{RC/RC}$-Pappa mutants (n=5-12/group) at 12 months of age. (F) Representative photomicrographs of Sirius red staining in kidneys of 4.5 month old Pkd1$^{RC/RC}$; Pappa mutant mice, and graph showing quantification of positively stained area (n=6 per group). Data are mean±SEM. *P<0.05, **P<0.01 compared to Pkd1$^{RC/RC}$-Pappa$^{+/+}$ group.

The kidneys from ADPKD-PAPPA mutants were further assessed for markers of inflammation, fibrosis, and renal injury. ADPKD-PAPP-A$^{++}$ kidneys had significantly higher levels of inflammatory markers Mcp1 and Tnfα in comparison with age-matched WT control mice, whereas abrogation of PAPP-A significantly decreased the renal inflammation in both ADPKD-PAPP-A$^{-/-}$ and ADPKD-PAPP-A$^{+/-}$ mice (FIG. 7A). Kidney tissues stained with anti-CD3 antibody also confirmed that PAPP-A deficiency reduced inflammation (FIG. 7B).

Expression of neutrophil gelatinase-associated lipocalin (Ngal), a marker of both acute and chronic kidney injury was analyzed to assess the renal injury. It was observed that in parallel with the development of kidney injury in the ADPKD animal model, Ngal mRNA expression was several-fold increased in ADPKD-PAPP-A$^{+/+}$ mice at all ages (4.5 and 12 months) compared to WT controls (FIG. 7C). In contrast, decreased dosing of PAPP-A protected mice against kidney injury as determined by Ngal mRNA levels (FIG. 4C). Similarly, the fibrosis markers collagen 1α1 (Col1α1) and Tgfβ were also reduced in ADPKD-PAPP-A$^{-/-}$ and ADPKD-PAPP-A$^{+/-}$ mice kidneys (FIG. 7D). Fibrosis analysis by Sirius red staining further confirmed that PAPP-A deficiency was associated with reduced fibrosis (FIG. 7E). In conclusion, abrogation of PAPP-A reduces cyst development, renal inflammation, injury and fibrosis in a murine model of ADPKD.

The levels were assessed of cystatin C, creatinine and urea, the biomarkers for renal function in ADPKD-PAPP-A mutant mice. Cystatin C was significantly lower in the PAPP-A deficient mice (FIG. 7F). The other biomarkers creatinine or urea did not differ between wild type and ADPKD mice and were not used further as markers of kidney function in the this model.

Additionally, PAPP-A enzymatic activity in kidney in vivo was determined in ADPKD and KO mice. PAPP-A-mediated IGFBP-4 proteolysis using kidney membrane fractions was assessed in WT, $Pkd1^{RC/RC}$ and $Pkd1^{RC/RC} Pappa^{-/-}$ mice. Cleavage of IGFBP-4 was only observed in membrane fractions of WT and $Pkd1^{RC/RC}$ mice but negligible in Pappa deficient mice, indicating that PAPP-A activity was higher in PKD mice but absent in $Pkd1^{RC/RC} Pappa^{-/-}$ mice (FIG. 8A). Importantly, ablation of PAPP-A had no significant effects on the serum levels of total IGF-1 (FIG. 8B) or mRNA expression of Igfbp4 and Igfr1 (FIG. 8C) indicating that PAPP-A promotes ADPKD cystic growth via degradation of IGFBP4 and potentially increasing bio-availability of IGF to activate its receptor.

Ten $Pkd1^{RC/RC}$ wild type mice for PAPP-A (WT) and ten $Pkd1^{RC/RC}$ mice heterozygous for PAPP-A gene (HET) were followed for survival over time. As shown in FIG. 12, the PAPP-A heterozygous mice had a significant improvement in survival over the wild type PAPP-A mice.

Figure 9:
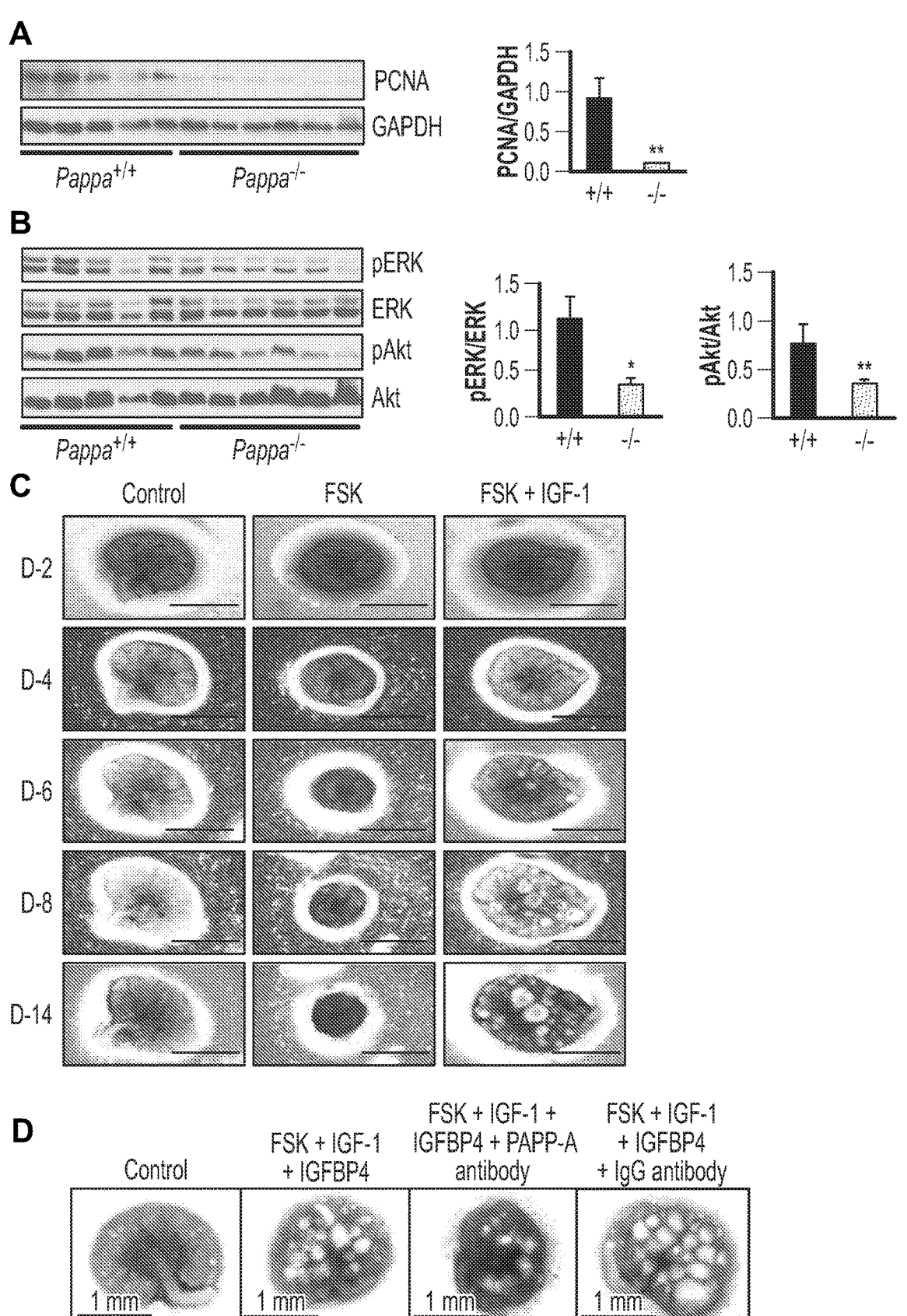
FIG. 9. The role of PAPP-A in the pathogenesis of ADPKD. Western blot analysis of (A) PCNA, (B) pERK/

The Role of PAPP-A in the Pathogenesis of ADPKD: Cellular Proliferation and the IGF Pathway As mentioned earlier, PAPP-A is a key regulator of the IGF-1 pathway. IGF-1 interacts with cell surface receptors leading to activation of proliferation pathways such as Akt and ERK. It has previously been shown that the IGF-1 pathway can induce cellular proliferation in ADPKD-derived renal epithelial cells in vitro (Nakamura, et al. *Journal of the American Society of Nephrology* 3, 1378-1386 (1993)). To determine whether PAPP-A plays a role in regulation of IGF-1 pathways and activation of cellular proliferation, the markers of proliferation in ADPKD-PAPP-A$^{+/+}$ and ADPKD-PAPP-A$^{-/-}$ mice were analyzed. Compatible with a role of PAPP-A as a regulator of the IGF-1 pathway and cellular proliferation in ADPKD, we observed that PCNA, a marker of cellular proliferation, was decreased in ADPKD-PAPP-A$^{-/-}$ mice (FIG. 9A). Interestingly, markers of neither autophagy (LC3 and p62) nor apoptosis (cleaved caspase 3) were different between ADPKD-PAPP-A$^{+/+}$ and ADPKD-PAPP-A$^{-/-}$ animals (FIG. 10A). These data indicate that PAPP-A's role in ADPKD is primarily mediated by the regulation of cellular proliferative pathways. Thus, next the role of PAPP-A in cellular signaling involved in the induction of cellular proliferation such as the ERK and the Akt pathways was determined. It was observed that KO of PAPP-A leads to a decrease in the phosphorylation of both ERK and Akt in animal models of ADPKD (FIG. 9B). To further validate the role of the IGF-1/IGFBP and PAPP-A pathway, RCTE cells (that express low levels of PAPP-A) were treated with IGF-1 alone, IGF-1 plus IGFBP4 or IGF-1 plus IGFBP4 and PAPP-A. It was observed that IGF-1 alone induced activation of both ERK and Akt in these cells (FIG. 10B). This effect was blocked by pre-incubation of IGF-1 with IGFBP4 (FIG. 10B). However, addition of catalytically active PAPP-A recovered the levels of ERK phosphorylation in these cells (FIG. 10B), indicating that secreted PAPP-A cleaves the IGF-1/IGFBP4, releasing free IGF-1 and allowing IGF-1 to activate the downstream proliferation molecules such as ERK and Akt in renal cells.

Although the role of the IGF-1 pathway has been speculated in ADPKD, no direct evidence exists. Therefore, to further investigate the role of IGF-IGFBP-PAPP-A pathway in the pathogenesis of ADPKD, the metanephric model of cyst induction (Barack and Boyle, 2011, supra) was used. Using this model, first it was explored whether IGF-1 has a permissive role in cyst formation in PKD. Embryonic kidneys were stimulated with forskolin (FSK) alone or FSK in the presence of IGF-1, and the results showed that IGF-1 is necessary for FSK-induced cystic formation in this model (FIG. 9C). Three dimensional Madin-Darby canine kidney (MDCK) cystogenic assay was also performed with FSK alone or in combination with IGF-1, and similarly indicated that IGF-1 in the presence of FSK significantly increases the number of cysts in these cells (FIG. 10C). Secondly, the effect of IGF-IGFBP complex and PAPP-A was assessed on cyst induction in metanephrons. Although, FSK alone was not sufficient to induce cysts in this model, the addition of IGF-1-IGFBP4 complex readily supported FSK-induced cystogenesis (FIG. 9D). Interestingly, addition of a PAPP-A blocking antibody completely abrogated cyst formation in the embryonic metanephric model (FIG. 9D). These data indicated that in the metanephric model endogenous PAPP-A can cleave IGFBP4 and increase the bioavailability of IGF-1 to activate its receptor and cystogenesis. To further explore this observation, the expression of PAPP-A was evaluated in the metaneprhic model. Indeed, it was observed that FSK treatment leads to a robust induction of PAPP-A expression in the methanephrons (FIG. 10D).

Next, the role of the IGF-1 pathway in ADPKD was determined in vivo using Pkd1$^{RC/RC}$ mice. Pkd1$^{RC/RC}$ mice were injected with either an anti-IGF-1 antibody (0.2 mg/kg body weight) or IgG (0.2 mg/kg body weight) once a week for 6 weeks. An improvement was observed in kidney weights, cystic burden, and molecular markers of inflammation, fibrosis and kidney injury (FIG. 10E, F). These results directly demonstrate for the first time a role for the IGF-1 pathway in the pathogenesis of ADPKD (FIGS. 10E,F).

Taken together, these data indicated that the IGF-IGFBP4-PAPP-A pathway plays an important role in the pathogenesis of ADPKD. In particular, PAPP-A via this pathway regulates the growth and expansion of cysts. Additionally, it indicates that targeting this pathway may have a therapeutic role in ADPKD patients. One of the advantages of targeting PAPP-A versus the IGF-1R is that it appears that PAPP-A over-expression might be kidney specific in ADPKD.

Interestingly, while PAPP-A expression was induced by FSK in experimental ADPKD, including cultured human ADPKD cells, mouse metanephros, and murine models of ADPKD, it was not induced by FSK in normal human kidney cells or wild type (WT) mice. Although this could be mediated by a higher increase in cAMP levels in ADPKD cells, it appears unlikely, since IGFBP4 expression is similarly stimulated by cAMP in control and ADPKD cells. Thus, it appears that there is a specific modification in the PAPP-A gene that makes it more responsive to cAMP-stimulation in ADPKD cells and tissues.

In Vivo Inhibition of PAPP-A Using mAb-PA Blocks the Progression of ADPKD

To investigate whether inhibition of PAPP-A ameliorates the cystic disease, a high-affinity IgG monoclonal antibody against a substrate-binding exosite of PAPP-A (mAb-PA), which blocks the proteolytic action of PAPP-A on IGF-1/

IGFBP4, was used (Mikkelsen, et al., 2014, supra; and Conover, et al., 2004, supra). Pkd1$^{RC/RC}$ mice were treated at 6 months of age with 30 mg/kg mAb-PA or IgG once a week intraperitoneally for six weeks. All the antibody-treated mice were healthy with normal behavior. The mAb-PA-treated mice showed a significant decrease in cystic burden, as assessed by reduced kidney size and cyst area compared to IgG-treated mice (FIG. 11A). The markers of renal inflammation, injury and fibrosis were also improved in mAb-PA-treated mice (FIG. 11B). These observations confirm that pharmacologic blockage of PAPP-A enzymatic activity ameliorates disease progression in the ADPKD mice.

Additional in vivo studies were performed using antibody mAb-CA (FIGS. 16A, 16B, and 21).

pKD1$^{RC/RC}$ mice with a C57BL/6J background were treated at 7.5 months of age with mAb-CA (10 mg/kg) or control (IgG) once a week intraperitoneally for 12 weeks. All the mAb-CA-treated mice were healthy and exhibited normal behavior. The mAb-CA-treated mice had a lower body weight (% of baseline) in comparison to control mice (FIG. 13A). The mAb-CA-treated mice showed a decrease in cystic burden, as assessed by reduced kidney weight, reduced ratio of kidney weight to heart weight, and a trend for reduced cyst area compared to IgG-treated mice (FIGS. 13B, 13C, and 13D).

PKD1$^{RC/RC}$ mice with a mixed background (C57BL6J and 129 S background) were treated at 7 weeks of age with mAb-CA (10 mg/kg) or control (IgG) once a week intraperitoneally for 12 weeks. All the mAb-CA-treated mice were healthy and exhibited normal behavior. The mAb-CA-treated mice had a lower body weight (% of baseline) in comparison to control mice. (FIG. 14A). The mAb-CA-treated mice had a reduced kidney weight and reduced ratio of kidney weight to heart weight as compared to IgG-treated mice (FIG. 14B, 14C).

Example 2—Generating Anti-PAPP-A Antibodies

Materials and Methods

Screening of Semi-Synthetic Phage Libraries

PAPP-A antibodies can be made using methods generally described in U.S. Pat. No. 8,653,020, hereby incorporated by reference in its entirety. Human PAPP-A (full length PAPP-A or a C-terminal fragment of PAPP-A amino acid residues 1133-1547) is immobilized (1 hour at 37° C.) to 3.5 mL Immunotubes (Nunc Maxisorp), which are coated overnight at 4° C. with polyclonal PAPP-A antibodies (5 μg/mL) in 100 mM sodium bicarbonate, pH 9.8. 3% skimmed milk powder in 20 mM Tris, 150 mM NaCl, pH 7.5 (TBS) is used as a blocking agent. Tomlinson I and J semi-synthetic phage libraries are used. Capture of phages from the libraries is carried out for 2 hours at RT while rotating gently. After capture, the tubes are rinsed 10 times in TBS containing 1 M NaCl and 0.1% Tween-20 (TBST), washed at 4° C. with 2 L TBST for five hours with a peristaltic pump, and rinsed five times with TBS. Elution of phages is carried out for 10 min at RT using 0.5 mL DPPC-treated trypsin (1 mg/mL) (Sigma) diluted in TBS or EDTA in TBS. Alternatively, other libraries than phage libraries can be used.

E. coli (TG1) are infected with the eluted phages for 30 min at 37° C. and plated on TYE plates supplemented with 1% glucose and ampicillin (100 μg/mL). Colonies are transferred to 96-well culture plates with 2×TY medium containing 1% glucose and ampicillin (100 μg/mL), and incubated overnight at 37° C. A replicate of each plate is incubated for 3 hours, and KM13 helper phages are added (109 to each well). The cells are incubated with the phage for 1 hour, and the medium is changed to 2×TY containing ampicillin (100 μg/mL) and kanamycin (50 μg/mL). The plates are incubated for 20 hours at 30° C., and phage-containing supernatants are analyzed by ELISA for binding to human PAPP-A (E483Q), which is immobilized in 96-well plates with polyclonal PAPP-A antibodies. The plates are blocked with 2% bovine serum albumin (Sigma) and washed with TBS containing 0.1% Tween-20, and detection is performed using HRP-conjugated anti-M13 (GE Healthcare). Phagemid DNA (pIT2) from selected clones is prepared and sequenced.

Animal Immunization and Hybridoma Production

PAPP-A antibodies can be made using methods generally described in Mikkelsen et al. (*Oncotarget*, 5:1014-1025 (2014)), hereby incorporated by reference in its entirety. PAPP-A knockout mice (Conover et al., *Development*, 131 (5):1187-1194 (2004)) are immunized with human PAPP-A complex purified from human pregnancy serum. 50 μg injections of PAPP-A are given subcutaneously in Freund's Complete Adjuvant (MP Biomedical, 0855828). Booster injection in Freund's Incomplete Adjuvant (MP Biomedical, 0855829) are given one month later. Responders are selected for final boosting following one additional month; approximately 160 μg of the antigen is injected intraperitoneally for four consecutive days. Mice are sacrificed on the fifth day, and the spleens are removed aseptically. Spleen cells are centrifuged, aliquoted and stored in liquid nitrogen. Spleen cells are fused with SP2/0 cells using one aliquot of the spleen cells. The culture supernatants of picked clones are screened on antigen coated plates, and positive clones are re-cloned. The clones are screened for recognition of purified human full length PAPP-A or a C-terminal PAPP-A fragment, PAPP-A (1133-1547). Selected clones are cultured for antibody production and purification on protein A Sepharose (GE Healthcare). Selected clones are screened for inhibitory activity of PAPP-A (human and murine) cleavage of IGFBP-4 and isotyped.

Yeast Display Production

PAPP-A antibodies also can be generated using yeast display methods such as those generally described in Feldhaus et al. (*Journal of Immunological Methods*, 290:69-80 (2004)). In yeast display methods, genetic methods are used to tether antibody domains to the yeast cell wall and display them on the surface of yeast. In particular, such yeast can be utilized to display antigen-binding domains expressed from a repertoire or combinatorial antibody library (e.g., human or murine). Examples of yeast display methods that can be used to make PAPP-A antibodies include those disclosed in U.S. Pat. No. 9,458,244 (Benatuil et al.), U.S. Pat. No. 9,469,688 (Benatuil et al.), U.S. Pat. No. 9,200,270 (Hsieh et at.), and U.S. Pat. No. 6,699,658 (Wittrup et al.), each of which are hereby incorporated by reference in their entirety.

Proteolytic Activity Assay

Proteolytic activity of PAPP-A against IGFBP-4 and -5 is analyzed. Purified substrates, quantified by amino acid analysis, are labelled with 125I (Amersham Biosciences). Cleavage reactions are carried out in 50 mM Tris-HCl, 100 mM NaCl, 1 mM CaCl$_2$), pH 7.5 in the absence (IGFBP-5) or presence (IGFBP-4) of a 10 fold molar excess of IGF-II (Diagnostic Systems Laboratories). Following incubation at 37° C., reactions are quenched by the addition of EDTA (10 mM) and are stored at −20° C. Cleavage products are separated by 10-20% SDS-PAGE and autoradiography is used to visualize the gels. The degree of cleavage is determined by quantification of band intensities using a Typhoon imaging system (GE Healthcare), and background levels (mock signals) are subtracted. Proteolytic activity of PAPP-A2 against IGFBP-5 in the absence of IGF is analyzed similarly. Analysis of peptidolytic activity against a full length IGFBP-4 or a 26-residue synthetic peptide derived from IGFBP-4 is also carried out. Residues on the N-terminal and C-terminal side of the cleavage site are modified with o-aminobenzoic acid and substituted with 3-nitrotyrosine, respectively. The reaction buffer is 50 mM Tris, pH 8.0, 0.01% Tween-20. For the Typhoon, 310 nm is used for excitation, and emission is detected at 420 nm.

Results

To obtain monoclonal antibodies with selective inhibitory activity against PAPP-A cleavage of IGFBP-4, a phage antibody library is screened for binding to the full length PAPP-A protein or a 60 kDa C-terminal fragment of human PAPP-A (residues 1133-1547). Bound phages are cloned, their binding to full-length PAPP-A is evaluated by ELISA, and scFv antibodies from selected phages are produced in *E. coli*. The scFv antibodies are assessed for inhibitory activity using the proteolytic assay. PAPP-A inhibitory scFv antibodies are obtained.

To obtain monoclonal antibodies with selective inhibitory activity against PAPP-A cleavage of IGFBP-4, a yeast display library is screened for binding to the full length PAPP-A protein or a 60 kDa C-terminal fragment of human PAPP-A (residues 1133-1547). Selected yeast are cloned, their binding to full-length PAPP-A is evaluated by ELISA, and antibodies from selected yeast are produced in HEK293 cells. The antibodies are assessed for inhibitory activity using the proteolytic assay. PAPP-A inhibitory antibodies are obtained.

Example 3—Characterization of Anti-PAPP-A Antibody mAb-CA

Materials and Methods

Antibody Production

An anti-PAPP-A antibody, mAb-CA, with mouse IgG1 isotype was produced using the general methodology described in Example 2. mAb-CA was produced in cells by transient transfection of HEK293 cells and purified by Protein A chromatography. The protein was estimated to be 98.9% monomer by SEC chromatography and had Endotoxin of less than 0.27 EU/mg. Binding kinetics of mAb-CA antibody to both human and mouse PAPP-A was evaluated by SPR with antibody capture on chip CM5 and PAPP-A concentrations ranging from 0.78 to 100 nM.

In Vitro PAPP-A Enzymatic Cleavage of IGF Binding Proteins

Human and murine PAPP-A proteins with C-terminal C-myc and Flag tags were expressed by stably transduced HEK293 cell line and purified by heparin column chromatography. Human and murine IGFBP-2, IGFBP-4 and IGFBP-5 proteins were produced recombinantly by transient expression in HEK293 cells with either N-terminal (for human proteins) or C-terminal (for murine proteins) 6His tag (SEQ ID NO: 32) and purified by Ni-Sepharose column chromatography. For enzymatic cleavage reaction, IGFBP-2 and IGFBP-4 proteins were pre-incubated with IGF1 of appropriate species (R&D Systems, 291-G1-200 for human and 791-MG-050 for mouse) for 30 minutes at 37° C. IGFBP-2/IGF1, IGFBP-4/IGF1 or IGFBP-5 proteins were then mixed with various concentrations of PAPP-A and incubated for 2-4 hours at 37° C. Final concentration in cleavage reactions were 90 nM for IGFBPs ad 850 nM for IGF1. Proteins were then resolved by capillary electrophoresis on Wes instrument (ProteinSimple) using capillary cartridge kit (ProteinSimple, cat. #SM-W002-1), probed with HisTag antibody (GeneScript, cat. #A00186) and visualized with anti-mouse detection module (ProteinSimple, cat. #DM-002). To evaluate neutralizing potency of mAb-CA antibody, PAPP-A protein was pre-incubated with various concentrations of mAb-CA antibody prior to adding to IGF1/IGFBP-4 mix. PAPP-A concentration is these assays was fixed to 0.4 nM for IGFBP-4, 3.5 nM for IGFBP-2 and 0.08 nM for IGFBP-5 cleavage.

Cellular pAKT Assay

IGFBP-4 protein was mixed with IGF1 and incubated for 30 minutes at 37° C. PAPP-A protein was added to IGFBP-4/IGF1 mix and incubated for 4-5 hours at 37° C. Final concentrations in the reaction were 90 nM for IGFBP-4, 15 nM for IGF1 and 0.6 nM for PAPP-A. HEK293 cells were plated in EMEM media without serum and allowed to adhere overnight. IGF1/IGFBP-4/PAPP-A mix was added to cells at 1:30 final dilution and incubated for 20 minutes at 37° C. Cells were lysed in MSD Tris Lysis buffer and analyzed by Phospho(Ser473)/Total Akt Whole Cell Lysate kit (MSD, K15100D) according to manufacturer's protocol. To evaluate neutralizing potency of mAb-CA antibody, PAPP-A protein was pre-incubated with various concentrations of mAb-CA antibody prior to adding to IGF1/IGFBP-4 mix.

Pharmacokinetics

Pharmacokinetic profile of mAb-CA antibody was evaluated by single dose IV injection of 5 mg/kg in C57BL/6 male mice. Antibody blood concentration was measured by direct ELISA with PAPP-A protein.

Results mAb-CA effectively blocked cleavage of both human and murine IGFBP-4 and IGFBP-2 by PAPP-A, but did not greatly affect PAPP-A's ability to cleave IGFBP-5 (FIG. 22). mAb-CA had sub-nanomolar affinity to murine PAPP-A, with a dissociation constant (KD) of 61 µM (FIG. 23) and a half maximum inhibitory concentration ($IC_{50}$) of 1.7 nM for mIGFBP-4 and 0.85 nM for mIGFBP-2 (FIG. 24, panels A and B). No IC50 could be calculated for mIGFBP-5 as the inhibition did not reach 50% (FIG. 24, panel C). In contrast, the antibody showed no binding activity to PAPP-A2, the closest homolog to PAPP-A (FIG. 23).

To assess whether this antibody could block IGF signaling stimulated by the combination of IGF-1, IGFBP-4, and PAPP-A, phosphorylation of AKT in HEK293T cells upon stimulation with IGF-1 was measured in the presence of IGFBP-4 and PAPP-A. mAb-CA blocked the downstream signaling of IGF-1 in HEK293 cells in a dose-dependent fashion, as measured by phosphorylation of AKT (FIGS. 25 and 26).

In vivo pharmacokinetic studies indicated that the antibody, formatted as an IgG1 isotype, has a half-life of 6.42 days in C57BL/6 mice, allowing for weekly dosing (FIG. 27).

Example 4—Characterization of Additional Anti-PAPP-A Antibodies

Materials and Methods

Antibody Production

Additional anti-PAPP-A antibodies human IgG1 isotype were generated using the general yeast display methodology described in Example 2. Antibodies were produced by transient transfection of HEK293 cells and purified by Protein A chromatography. Binding kinetics of anti-PAPP-A antibodies to both human and mouse PAPP-A were evaluated by SPR with antibody capture on chip CM5 and PAPP-A concentrations ranging from 0.78 to 100 nM.

Proteolytic Activity Assay

Proteolytic activity of PAPP-A against IGFBP-4 was analyzed as described in Example 3 with the exception that only one antibody concentration (50 nM) was tested.

Cellular pAKT Assay

Cellular pAKT assay was with mouse IGF1, mouse IGFBP4, and mouse PAPP-A was performed as described in Example 3.

Results

Multiple antibodies binding to human and murine PAPP-A were generated from yeast display libraries. FIG. 28 shows binding affinities of five representative antibodies with a dissociation constant (KD) ranging from triple digit pM to double digit nM.

Approximately 90 percent of antibodies generated from yeast libraries were able to fully or partially block PAPP-A cleavage of IGFBP4 at concentration 50 nM. FIG. 29 shows that the five representative antibodies effectively blocking cleavage of human IGFBP4.

These antibodies could also block IGF signaling in pAKT assay with mouse IGFBP4, IGF1, and PAPP-A, with potencies ranging from triple digit pM to single digit nM (FIG. 30). Also shown are the $IC_{50}$ values for each antibody.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of treating polycystic kidney disease in a mammal, wherein said method comprises administering an anti-PAPP-A antibody to a mammal identified as having polycystic kidney disease, wherein a symptom of said polycystic kidney disease is reduced in said mammal, wherein the anti-PAPP-A antibody comprises a. a heavy chain variable (VH) domain comprising a CDR1 comprising a sequence as set forth in SEQ ID NO: 1, a CDR2 comprising a sequence as set forth in SEQ ID NO: 2 and a CDR3 comprising a sequence as set forth in SEQ ID NO: 3, and a light chain variable (VL) domain comprising a CDR1 comprising a sequence as set forth in SEQ ID NO: 9, a CDR2 comprising a sequence as set forth in SEQ ID NO: 10 and a CDR3 comprising a sequence as set forth in SEQ ID NO: 11;

b. a heavy chain variable (VH) domain comprising a sequence as set forth in SEQ ID NO: 19 and a light chain variable (VL) domain comprising a sequence as set forth in SEQ ID NO: 20;

c. a heavy chain variable (VH) domain comprising a sequence as set forth in SEQ ID NO: 22 and a light chain variable (VL) domain comprising a sequence as set forth in SEQ ID NO: 23;

d. a heavy chain variable (VH) domain comprising a sequence as set forth in SEQ ID NO: 24 and a light chain variable (VL) domain comprising a sequence as set forth in SEQ ID NO: 25; or e. a heavy chain variable (VH) domain comprising a sequence as set forth in SEQ ID NO: 26 and a light chain variable (VL) domain comprising a sequence as set forth in SEQ ID NO: 27.

2. The method of claim 1, wherein said mammal is a human.

3. The method of claim 1, wherein said polycystic kidney disease is autosomal dominant polycystic kidney disease (ADPKD).

4. The method of claim 1, wherein said antibody is a neutralizing antibody that blocks the proteolytic activity of PAPP-A.

5. The method of claim 4, wherein said antibody is a monoclonal antibody.

6. The method of claim 4, wherein said antibody is a single-chain variable fragment.

7. The method of claim 1, wherein said symptom of said polycystic kidney disease is cystic burden.

8. The method of claim 1, wherein said symptom of said polycystic kidney disease is kidney size.

9. The method of claim 1, wherein said antibody comprises a VH domain comprising a sequence as set forth in SEQ ID NO: 8 or 17.

10. The method of claim 1, wherein said antibody comprises a VL domain comprising a sequence as set forth in SEQ ID NO: 16 or 18.

11. The method of claim 1, wherein said antibody comprises a VH domain comprising a sequence as set forth in SEQ ID NO: 8 and a VL domain comprising a sequence as set forth in SEQ ID NO: 16.

12. The method of claim 1, wherein said antibody comprises a VH domain comprising a sequence as set forth in SEQ ID NO: 19.

13. The method of claim 1, wherein said antibody comprises a VL domain comprising a sequence as set forth in SEQ ID NO: 20.

14. The method of claim 1, wherein said antibody comprises a VH domain comprising a sequence as set forth in SEQ ID NO: 19 and a VL domain comprising a sequence as set forth in SEQ ID NO: 20.

\* \* \* \* \*